US012742779B1

(12) United States Patent
Mendivil Medina

(10) Patent No.: US 12,742,779 B1
(45) Date of Patent: Sep. 22, 2026

(54) KITS

(71) Applicant: Takeda Pharmaceutical Company Limited, Osaka (JP)

(72) Inventor: Joan Yesid Mendivil Medina, Cham (CH)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 19/196,916

(22) Filed: May 2, 2025

Related U.S. Application Data

(63) Continuation of application No. 16/817,671, filed on Mar. 13, 2020.

(60) Provisional application No. 62/818,189, filed on Mar. 14, 2019.

(51) Int. Cl.
*G01N 33/53* (2006.01)
*G01N 33/573* (2006.01)

(52) U.S. Cl.
CPC . *G01N 33/573* (2013.01); *G01N 2333/96455* (2013.01); *G01N 2800/52* (2013.01)

(58) Field of Classification Search
None
See application file for complete search history.

(56) References Cited

U.S. PATENT DOCUMENTS 3,682,776 A 8/1972 Grundmann et al.
3,691,016 A 9/1972 Patel
3,969,287 A 7/1976 Jaworek et al.
4,118,481 A 10/1978 Schnabel et al.
4,153,687 A 5/1979 Schnabel et al.
4,179,337 A 12/1979 Davis et al.
4,195,128 A 3/1980 Hildebrand et al.
4,229,537 A 10/1980 Hodgins et al.
4,247,642 A 1/1981 Hirohara et al.
4,330,440 A 5/1982 Ayers et al.
4,377,572 A 3/1983 Schwarz et al.
4,399,216 A 8/1983 Axel et al.
4,595,674 A 6/1986 Tschesche et al.
4,609,725 A 9/1986 Brady et al.
4,634,665 A 1/1987 Axel et al.
4,657,893 A 4/1987 Krantz et al.
4,845,242 A 7/1989 Powers et al.
4,881,175 A 11/1989 Ladner
4,946,778 A 8/1990 Ladner et al.
4,966,852 A 10/1990 Wun et al.
5,045,452 A 9/1991 Spragg et al.
5,106,833 A 4/1992 Broze, Jr. et al.
5,118,668 A 6/1992 Auerswald et al.
5,166,133 A 11/1992 Houston et al.
5,179,017 A 1/1993 Axel et al.
5,212,091 A 5/1993 Diaz-Collier et al.
5,223,409 A 6/1993 Ladner et al.
5,260,203 A 11/1993 Ladner et al.
5,278,144 A 1/1994 Wolf
5,278,285 A 1/1994 Ebbers et al.
5,312,736 A 5/1994 Rasmussen et al.
5,372,933 A 12/1994 Zamarron et al.
5,373,090 A 12/1994 Norris et al.
5,378,614 A 1/1995 Petersen et al.
5,407,915 A 4/1995 Fritz et al.
5,409,895 A 4/1995 Morishita et al.
5,426,224 A 6/1995 Lee et al.
5,441,931 A 8/1995 Sprecher et al.
5,444,156 A 8/1995 Veloso et al.
5,446,090 A 8/1995 Harris
5,455,338 A 10/1995 Sprecher et al.
5,466,783 A 11/1995 Wun et al.
5,563,123 A 10/1996 Innis et al.
5,576,294 A 11/1996 Norris et al.
5,583,107 A 12/1996 Wolf et al.
5,585,089 A 12/1996 Queen et al.
5,589,359 A 12/1996 Innis et al.
5,618,696 A 4/1997 Norris et al.
5,629,176 A 5/1997 Bjørn et al.
5,635,187 A 6/1997 Bathurst et al.
5,648,331 A 7/1997 Koudsi et al.
5,663,143 A 9/1997 Ley et al.
5,672,662 A 9/1997 Harris et al.
5,677,146 A 10/1997 Sprecher et al.
5,693,761 A 12/1997 Queen et al.
5,693,762 A 12/1997 Queen et al.
(Continued)

FOREIGN PATENT DOCUMENTS

AT 275583 T 9/2004
BR 112015017195 A2 7/2017
(Continued)

OTHER PUBLICATIONS

Torzewski et al., Animal Models of C-Reactive Protein, Hindawl Publishing Corporation, Mediators of Inflammation, vol. 2014, Article ID 683598, 2014, pp. 1-7. (Year: 2014).*
(Continued)

*Primary Examiner* — Gary Counts
(74) *Attorney, Agent, or Firm* — Wolf, Greenfield & Sacks, P.C.

(57) ABSTRACT

Provided herein are methods of assessing the efficacy of a treatment regimen in a subject by measuring the concentration of one or more biomarkers associated with plasma kallikrein prior to the first dose of a polypeptide that binds plasma kallikrein. A treatment regimen is considered effective if the concentration of one or more biomarkers decreases after administration of the polypeptide.

4 Claims, 14 Drawing Sheets

Specification includes a Sequence Listing.

(56) References Cited

U.S. PATENT DOCUMENTS 5,695,760 A 12/1997 Faanes et al.
5,696,088 A 12/1997 Innis et al.
5,719,041 A 2/1998 Lazarus et al.
5,736,364 A 4/1998 Kelley et al.
5,739,208 A 4/1998 Harris
5,747,449 A 5/1998 Lasters et al.
5,770,568 A 6/1998 Auerswald et al.
5,780,265 A 7/1998 Dennis et al.
5,786,328 A 7/1998 Dennis et al.
5,795,865 A 8/1998 Markland et al.
5,795,954 A 8/1998 Lazarus et al.
5,800,385 A 9/1998 Demopulos et al.
5,804,376 A 9/1998 Braxton et al.
5,834,244 A 11/1998 Dennis et al.
5,843,895 A 12/1998 Lazarus et al.
5,849,992 A 12/1998 Meade et al.
5,853,723 A 12/1998 Jacobs et al.
5,863,893 A 1/1999 Dennis et al.
5,869,637 A 2/1999 Au-Young et al.
5,874,407 A 2/1999 Kelley et al.
5,880,256 A 3/1999 Dennis et al.
5,900,461 A 5/1999 Harris
5,914,316 A 6/1999 Brown et al.
5,932,462 A 8/1999 Harris et al.
5,951,974 A 9/1999 Gilbert et al.
5,962,266 A 10/1999 White et al.
5,990,237 A 11/1999 Bentley et al.
5,994,125 A 11/1999 Markland et al.
6,001,596 A 12/1999 Hillman et al.
6,004,579 A 12/1999 Bathurst et al.
6,008,196 A 12/1999 Curran et al.
6,010,880 A 1/2000 Markland et al.
6,013,448 A 1/2000 Braxton et al.
6,013,763 A 1/2000 Braisted et al.
6,017,723 A 1/2000 Rao et al.
6,057,287 A 5/2000 Markland et al.
6,063,764 A 5/2000 Creasey et al.
6,071,723 A 6/2000 Markland et al.
6,087,473 A 7/2000 Conklin et al.
6,090,916 A 7/2000 Vlasuk et al.
6,103,499 A 8/2000 Markland et al.
6,103,500 A 8/2000 Innis et al.
6,113,896 A 9/2000 Lazarus et al.
6,126,933 A 10/2000 Warne et al.
6,159,938 A 12/2000 Gyorkos et al.
6,171,587 B1 1/2001 Wun et al.
6,174,721 B1 1/2001 Innis et al.
6,180,607 B1 1/2001 Davies et al.
6,214,966 B1 4/2001 Harris
6,242,414 B1 6/2001 Johnson et al.
6,258,351 B1 7/2001 Harris
6,261,279 B1 7/2001 Demopulos et al.
6,306,884 B1 10/2001 Buckman et al.
6,333,402 B1 12/2001 Markland et al.
6,348,558 B1 2/2002 Harris et al.
6,362,254 B2 3/2002 Harris et al.
6,362,276 B1 3/2002 Harris et al.
6,376,604 B2 4/2002 Kozlowski
6,407,213 B1 6/2002 Carter et al.
6,413,507 B1 7/2002 Bentley et al.
6,423,498 B1 7/2002 Markland et al.
6,432,397 B1 8/2002 Harris
6,455,639 B1 9/2002 Yasukohchi et al.
6,472,195 B2 10/2002 Hillman et al.
6,515,100 B2 2/2003 Harris
6,534,276 B1 3/2003 Wun et al.
6,548,262 B2 4/2003 Gentz et al.
6,576,235 B1 6/2003 Williams et al.
6,583,108 B1 6/2003 Tamburini et al.
6,610,281 B2 8/2003 Harris
6,624,246 B2 9/2003 Kozlowski
6,664,331 B2 12/2003 Harris et al.
6,689,582 B1 2/2004 Davies et al.
6,710,125 B2 3/2004 Kozlowski
6,774,180 B2 8/2004 Kozlowski et al.
6,783,960 B2 8/2004 Innis et al.
6,783,965 B1 8/2004 Sherman et al.
6,806,360 B2 10/2004 Wun et al.
6,814,982 B2 11/2004 Poncin et al.
6,914,135 B2 7/2005 Sheppard et al.
6,953,674 B2 10/2005 Markland et al.
6,989,369 B2 1/2006 Ladner et al.
7,064,107 B2 6/2006 Ladner et al.
7,067,144 B2 6/2006 Demopulos et al.
7,078,383 B2 7/2006 Ley et al.
7,153,829 B2 12/2006 Ladner et al.
7,166,576 B2 1/2007 Cicardi et al.
7,235,530 B2 6/2007 Blair et al.
7,276,480 B1 10/2007 Ladner et al.
7,550,427 B2 6/2009 Ley et al.
7,628,983 B2 12/2009 Markland et al.
7,704,949 B2 4/2010 Ladner et al.
7,718,617 B2 5/2010 Cicardi et al.
7,811,991 B2 10/2010 Ladner et al.
7,851,442 B2 12/2010 Ladner et al.
7,919,462 B2 4/2011 Markland et al.
8,034,775 B2 10/2011 Ladner et al.
8,124,586 B2 2/2012 Ladner et al.
8,188,045 B2 5/2012 Blair et al.
8,283,321 B2 10/2012 Markland et al.
8,816,055 B2 8/2014 Sexton et al.
8,822,653 B2 9/2014 Sexton et al.
9,266,964 B2 2/2016 Sexton et al.
10,316,095 B2 6/2019 Fowler et al.
10,336,832 B2 7/2019 Sexton et al.
10,370,453 B2 8/2019 Sexton et al.
10,428,158 B2 10/2019 Conley et al.
10,648,990 B2 5/2020 Sexton et al.
11,046,785 B2 6/2021 Conley et al.
11,084,884 B2 8/2021 Sexton et al.
11,156,612 B2 10/2021 Sexton et al.
11,286,307 B2 3/2022 Adelman et al.
11,299,553 B2 4/2022 Nixon et al.
11,340,237 B2 5/2022 Sexton et al.
11,372,002 B2 6/2022 Sexton et al.
11,401,346 B2 8/2022 Sexton et al.
11,505,620 B2 11/2022 Sexton et al.
11,892,450 B2 2/2024 Kusumam et al.
12,084,515 B2 9/2024 Conley et al.
12,110,343 B2 10/2024 Nixon et al.
12,384,854 B2 8/2025 Sexton et al.
12,460,016 B2 11/2025 Sexton et al.
12,528,880 B2 1/2026 Nurse et al.
2001/0027180 A1 10/2001 Isaacs
2002/0102703 A1 8/2002 Sheppard et al.
2002/0111460 A1 8/2002 Holloway
2003/0012969 A1 1/2003 Clark
2003/0096733 A1 5/2003 Ny et al.
2003/0100070 A1 5/2003 Holloway
2003/0113726 A1 6/2003 Tsuchihashi et al.
2003/0114372 A1 6/2003 White et al.
2003/0138417 A1 7/2003 Kaisheva et al.
2003/0148271 A1 8/2003 Hillman et al.
2003/0153046 A1 8/2003 Jensen et al.
2003/0175919 A1 9/2003 Ley et al.
2003/0223977 A1 12/2003 Ley et al.
2004/0038893 A1 2/2004 Ladner et al.
2004/0049018 A1 3/2004 Bailon et al.
2004/0053206 A1 3/2004 Cicardi et al.
2004/0062746 A1 4/2004 Martinez et al.
2004/0062748 A1 4/2004 Martinez et al.
2004/0106747 A1 6/2004 Bailon et al.
2004/0126361 A1 7/2004 Saifer et al.
2004/0152633 A1 8/2004 Jorgensen et al.
2004/0171794 A1 9/2004 Ladner et al.
2004/0180827 A1 9/2004 Chen et al.
2004/0209243 A1 10/2004 Nixon et al.
2005/0004021 A1 1/2005 Sprecher et al.
2005/0075665 A1 4/2005 Brenzel et al.
2005/0089515 A1 4/2005 Ley et al.
2005/0164928 A1 7/2005 Ladner et al.
2005/0164945 A1 7/2005 Nixon et al.
2005/0180977 A1 8/2005 Nixon et al.
2006/0069020 A1 3/2006 Blair et al.

(56) References Cited

U.S. PATENT DOCUMENTS

| | | | |
|---|---|---|---|
| 2006/0194727 | A1 | 8/2006 | Ladner et al. |
| 2006/0228331 | A1 | 10/2006 | Peschke et al. |
| 2006/0264603 | A1 | 11/2006 | Markland et al. |
| 2007/0004910 | A1 | 1/2007 | Sexton et al. |
| 2007/0020252 | A1 | 1/2007 | Ladner et al. |
| 2007/0041959 | A1 | 2/2007 | Ley et al. |
| 2007/0049522 | A1 | 3/2007 | Ladner et al. |
| 2007/0065407 | A1 | 3/2007 | Patten et al. |
| 2007/0079096 | A1 | 4/2007 | Chen |
| 2007/0100133 | A1 | 5/2007 | Beals et al. |
| 2007/0117752 | A1 | 5/2007 | Larsen et al. |
| 2007/0213275 | A1 | 9/2007 | Clark et al. |
| 2007/0249807 | A1 | 10/2007 | Ladner et al. |
| 2007/0253949 | A1 | 11/2007 | Golz et al. |
| 2008/0038276 | A1 | 2/2008 | Sinha et al. |
| 2008/0038748 | A1 | 2/2008 | Kojima et al. |
| 2008/0050716 | A1 | 2/2008 | Cicardi et al. |
| 2008/0064637 | A1 | 3/2008 | Ladner et al. |
| 2008/0076712 | A1 | 3/2008 | Ladner et al. |
| 2008/0131426 | A1 | 6/2008 | Ladner et al. |
| 2008/0139473 | A1 | 6/2008 | Ladner et al. |
| 2008/0152656 | A1 | 6/2008 | Ladner et al. |
| 2008/0182283 | A1 | 7/2008 | Markland et al. |
| 2008/0188409 | A1 | 8/2008 | Blair et al. |
| 2008/0200646 | A1 | 8/2008 | Ladner et al. |
| 2008/0221031 | A1 | 9/2008 | Blair et al. |
| 2008/0226655 | A1 | 9/2008 | Ladner et al. |
| 2008/0255025 | A1 | 10/2008 | Ladner |
| 2008/0260752 | A1 | 10/2008 | Ladner et al. |
| 2008/0299050 | A1 | 12/2008 | Bortz et al. |
| 2009/0023651 | A1 | 1/2009 | Markland et al. |
| 2009/0062195 | A1 | 3/2009 | Ladner et al. |
| 2009/0075887 | A1 | 3/2009 | McPherson |
| 2009/0082267 | A1 | 3/2009 | Ladner et al. |
| 2009/0105142 | A1 | 4/2009 | Moscicki |
| 2009/0117130 | A1 | 5/2009 | Ladner et al. |
| 2009/0123475 | A9 | 5/2009 | Siegel |
| 2009/0215119 | A1 | 8/2009 | Ladner |
| 2009/0221480 | A1 | 9/2009 | Blair et al. |
| 2009/0227494 | A1 | 9/2009 | Blair et al. |
| 2009/0227495 | A1 | 9/2009 | Blair et al. |
| 2009/0233852 | A1 | 9/2009 | Blair et al. |
| 2009/0234009 | A1 | 9/2009 | Blair et al. |
| 2009/0247452 | A1 | 10/2009 | Ellis et al. |
| 2009/0247453 | A1 | 10/2009 | Blair et al. |
| 2009/0264350 | A1 | 10/2009 | Blair et al. |
| 2010/0034805 | A1 | 2/2010 | Ladner et al. |
| 2010/0183625 | A1 | 7/2010 | Sternlicht |
| 2010/0273721 | A1 | 10/2010 | Belichard |
| 2010/0285507 | A1 | 11/2010 | Cho et al. |
| 2010/0286061 | A1 | 11/2010 | Devy et al. |
| 2011/0008762 | A1 | 1/2011 | Cicardi et al. |
| 2011/0086801 | A1 | 4/2011 | Ladner et al. |
| 2011/0136746 | A1 | 6/2011 | Markland et al. |
| 2011/0142851 | A1 | 6/2011 | Misher et al. |
| 2011/0200611 | A1 | 8/2011 | Sexton |
| 2012/0201756 | A1 | 8/2012 | Sexton |
| 2012/0264798 | A1 | 10/2012 | Sinha et al. |
| 2012/0328517 | A1 | 12/2012 | Markland et al. |
| 2013/0012438 | A1 | 1/2013 | Blair et al. |
| 2013/0216556 | A1 | 8/2013 | Fowler et al. |
| 2014/0302048 | A1 | 10/2014 | Sexton et al. |
| 2014/0303357 | A1 | 10/2014 | Lim et al. |
| 2014/0335023 | A1 | 11/2014 | Sexton et al. |
| 2015/0274841 | A1 | 10/2015 | Conley et al. |
| 2015/0362492 | A1 | 12/2015 | Joseph et al. |
| 2015/0362493 | A1 | 12/2015 | Sexton et al. |
| 2016/0017055 | A1 | 1/2016 | Nixon et al. |
| 2016/0102150 | A1 | 4/2016 | Sexton et al. |
| 2017/0002094 | A1 | 1/2017 | Sexton et al. |
| 2018/0002447 | A1 | 1/2018 | Sexton et al. |
| 2018/0002448 | A1 | 1/2018 | Sexton et al. |
| 2018/0002449 | A1 | 1/2018 | Sexton et al. |
| 2018/0037664 | A1 | 2/2018 | Sexton et al. |
| 2018/0037665 | A1 | 2/2018 | Sexton et al. |
| 2018/0037666 | A1 | 2/2018 | Sexton et al. |
| 2018/0298110 | A1 | 10/2018 | Chyung et al. |
| 2019/0185580 | A1 | 6/2019 | Nixon et al. |
| 2020/0017602 | A1 | 1/2020 | Sexton et al. |
| 2020/0109213 | A1 | 4/2020 | Sexton et al. |
| 2020/0109214 | A1 | 4/2020 | Peng et al. |
| 2020/0115469 | A1 | 4/2020 | Conley et al. |
| 2020/0317815 | A1 | 10/2020 | Mendivil Medina |
| 2021/0087293 | A1 | 3/2021 | Sexton et al. |
| 2022/0033521 | A1 | 2/2022 | Conley et al. |
| 2022/0169749 | A1 | 6/2022 | Chyung et al. |
| 2022/0315668 | A1 | 10/2022 | Adelman et al. |
| 2023/0002509 | A1 | 1/2023 | Nixon et al. |
| 2023/0104754 | A1 | 4/2023 | Lu et al. |
| 2023/0112931 | A1 | 4/2023 | Sexton et al. |
| 2023/0192889 | A1 | 6/2023 | Nurse et al. |
| 2023/0340150 | A1 | 10/2023 | Sexton et al. |
| 2025/0129182 | A1 | 4/2025 | Nixon et al. |
| 2026/0035482 | A1 | 2/2026 | Chyung et al. |

FOREIGN PATENT DOCUMENTS

| | | | |
|---|---|---|---|
| BR | 112017020864 | A2 | 7/2018 |
| BR | 112013017080 | B1 | 4/2025 |
| CA | 2180950 | A1 | 8/1995 |
| CN | 1233256 | A | 10/1999 |
| CN | 101928346 | A | 12/2010 |
| CN | 103635489 | A | 3/2014 |
| CN | 105051068 | A | 11/2015 |
| CN | 105073778 | A | 11/2015 |
| CN | 106459210 | A | 2/2017 |
| CN | 108602893 | A | 9/2018 |
| CN | 109716129 | A | 5/2019 |
| DE | 69533472 | T2 | 1/2006 |
| EA | 2016/91470 | A1 | 12/2016 |
| EA | 2017/92161 | A1 | 4/2018 |
| EP | 0 132 732 | A2 | 2/1985 |
| EP | 0 210 029 | A2 | 1/1987 |
| EP | 0 255 011 | A2 | 2/1988 |
| EP | 0 274 826 | A1 | 7/1988 |
| EP | 0 285 123 | A2 | 10/1988 |
| EP | 0 301 122 | A1 | 2/1989 |
| EP | 0 307 592 | A2 | 3/1989 |
| EP | 0 318 451 | A2 | 5/1989 |
| EP | 0 401 508 | A2 | 12/1990 |
| EP | 0 486 001 | A1 | 5/1992 |
| EP | 0 621 870 | B1 | 11/1994 |
| EP | 0 621 871 | B1 | 11/1994 |
| EP | 0 739 355 | B1 | 10/1996 |
| EP | 1 288 305 | A2 | 3/2003 |
| EP | 1 484 339 | A2 | 12/2004 |
| JP | H07504891 | A | 6/1995 |
| JP | H09509838 | A | 10/1997 |
| JP | H09511131 | A | 11/1997 |
| JP | H10503375 | A | 3/1998 |
| JP | 2002-524076 | A | 8/2002 |
| JP | 2006-501168 | A | 1/2006 |
| JP | 2008-514624 | A | 5/2008 |
| JP | 2009-529553 | A | 8/2009 |
| JP | 2013-516478 | A | 5/2013 |
| JP | 2014-506257 | A | 3/2014 |
| JP | 2014-515763 | A | 7/2014 |
| JP | 2016-536012 | A | 11/2016 |
| JP | 2017-503820 | A | 2/2017 |
| JP | 2019-501886 | A | 1/2019 |
| JP | 6845012 | B2 | 3/2021 |
| JP | 7585193 | B2 | 11/2024 |
| KR | 10-2016-0122169 | A | 10/2016 |
| KR | 10-2799778 | B1 | 4/2025 |
| MX | 2017/012423 | A | 1/2018 |
| WO | WO 1987/05396 | A1 | 9/1987 |
| WO | WO 1989/010374 | A1 | 11/1989 |
| WO | WO 1990/002809 | | 3/1990 |
| WO | WO 1992/006111 | A1 | 4/1992 |
| WO | WO 1993/009233 | A2 | 5/1993 |
| WO | WO 1993/014120 | A1 | 7/1993 |
| WO | WO 1993/014121 | A1 | 7/1993 |
| WO | WO 1993/014122 | A1 | 7/1993 |
| WO | WO 1995/018830 | A2 | 7/1995 |

(56) References Cited

FOREIGN PATENT DOCUMENTS

| | | | | |
|---|---|---|---|---|
| WO | WO 1995/021601 | A2 | 8/1995 | |
| WO | WO 1995/023860 | A2 | 9/1995 | |
| WO | WO 1996/004378 | A2 | 2/1996 | |
| WO | WO 1996/020278 | A2 | 7/1996 | |
| WO | WO 1996/035788 | A2 | 11/1996 | |
| WO | WO 1997/033996 | A2 | 9/1997 | |
| WO | WO 1998/052976 | A1 | 11/1998 | |
| WO | WO 1999/063090 | A2 | 12/1999 | |
| WO | WO 2000/014235 | A1 | 3/2000 | |
| WO | WO 2000/034317 | A2 | 6/2000 | |
| WO | WO 2001/009968 | A1 | 2/2001 | |
| WO | WO 2001/014424 | A2 | 3/2001 | |
| WO | WO 2001/068707 | A1 | 9/2001 | |
| WO | WO 2001/079480 | A1 | 10/2001 | |
| WO | WO 2002/006334 | A1 | 1/2002 | |
| WO | WO 2002/006539 | A1 | 1/2002 | |
| WO | WO 2002/092147 | A2 | 11/2002 | |
| WO | WO 2002/094200 | A2 | 11/2002 | |
| WO | WO 2003/066824 | A2 | 8/2003 | |
| WO | WO 2003/103475 | A2 | 12/2003 | |
| WO | WO 2004/019968 | A1 | 3/2004 | |
| WO | WO 2004/062646 | A1 | 7/2004 | |
| WO | WO 2004/062689 | A1 | 7/2004 | |
| WO | WO 2005/021556 | A2 | 3/2005 | |
| WO | WO 2005/021557 | A2 | 3/2005 | |
| WO | WO 2005/075665 | A2 | 8/2005 | |
| WO | WO 2006/017538 | A2 | 2/2006 | |
| WO | WO 2006/036860 | A2 | 4/2006 | |
| WO | WO 2006/066878 | A1 | 6/2006 | |
| WO | WO 2006/089005 | A2 | 8/2006 | |
| WO | WO 2007/079096 | A2 | 7/2007 | |
| WO | WO 2007/104541 | A2 | 9/2007 | |
| WO | WO 2007/106746 | A2 | 9/2007 | |
| WO | WO 2008/000833 | A2 | 1/2008 | |
| WO | WO 2009/026334 | A2 | 2/2009 | |
| WO | WO 2009/026539 | A1 | 2/2009 | |
| WO | WO 2009/102927 | A1 | 8/2009 | |
| WO | WO 2010/003475 | A2 | 1/2010 | |
| WO | WO 2010/006746 | A2 | 1/2010 | |
| WO | WO 2010/080833 | A1 | 7/2010 | |
| WO | WO 2011/085103 | A2 | 7/2011 | |
| WO | WO 2012/094587 | A1 | 7/2012 | |
| WO | WO 2013/186700 | A1 | 12/2013 | |
| WO | WO 2014/113701 | A1 | 7/2014 | |
| WO | WO 2014/113712 | A1 | 7/2014 | |
| WO | WO 2014/152232 | A2 | 9/2014 | |
| WO | WO 2015/112578 | A1 | 7/2015 | |
| WO | WO 2016/160926 | A1 | 10/2016 | |
| WO | WO2017070170 | A1 * | 4/2017 | ............ G01N 33/68 |
| WO | WO 2019/028362 | A1 | 2/2019 | |
| WO | WO 2019/048961 | A1 | 3/2019 | |
| WO | WO 2020/047352 | A1 | 3/2020 | |
| WO | WO 2020/186132 | A1 | 9/2020 | |

OTHER PUBLICATIONS

Van Der Vekiens et al., Human and equine cardiovascular endocrinology: beware to compare, Cardiovascular Endocrinology 2013, vol. 2, No. 4, pp. 67-76. (Year: 2013).*

[No Author Listed], Prescribing Information for Takhzyro(®). FDA. Feb. 3, 2023. Reference ID: 5120543. pp. 1-21 https://www.accessdata.fda.gov/drugsatfda_docs/label/2023/761090s010lbl.pdf [last accessed Aug. 18, 2025]. 21 pages.

Kokoye et al., A Comparison of the Effects of Factor XII Deficiency and Prekallikrein Deficiency on Thrombus Formation. Thromb Res. Apr. 2016;140:118-124. doi: 10.1016/j.thromres.2016.02.020. Epub Feb. 18, 2016. Author Manuscript, 19 pages.

Maurer et al. Lanadelumab in Patients 2 to Less Than 12 Years Old With Hereditary Angioedema: Results From the Phase 3 Spring Study. J Allergy Clin Immunol Pract. Jan. 2024;12(1):201-11.e6. doi: 10.1016/j.jaip.2023.09.009. Epub Sep. 18, 2023.

International Preliminary Report on Patentability mailed Sep. 23, 2021 for Application No. PCT/US2020/022535.

International Search Report and Written Opinion mailed Jul. 2, 2020 for Application No. PCT/US2020/022535.

[No Author Listed] Dyax's DX-2930 granted Orphan Drug designation in hereditary angioedema. Dec. 6, 2013.

[No Author Listed] Fair Disclosure Wire, "Dyax Corp. announces positive results from phase 1a clinical trial of DX2930" dated Feb. 25, 2014. Last accessed from http://dialog.proquest.com/professional/printviewfile?accountid=157282 on May 20, 2016. p. 1-15.

[No Author Listed], Creatine Kinase (CK). Cleveland Clinic. Last accessed from: https://my.clevelandclinic.org/health/diagnostics/22692-creatine-kinase-ck on Sep. 17, 2024. 13 pages.

[No Author Listed], Creatine Phosphokinase (CPK). Johns Hopkins Lupus Center. Last accessed from: https://www.hopkinslupus.org/lupus-tests/clinical-tests/creatine-phosphokinase-cpk/ on Jul. 25, 2025. 1 page.

[No Author Listed], DX-2930, A New Drug for Hereditary Angioedema, Received Breakthrough Pharmaceutical Qualification From FDA. Journal of Guangdong Pharmaceutical University. Aug. 25, 2015;31:534. Source: Bio Valley Jul. 8, 2015.

[No Author Listed], Efficacy and Safety Study of DX-2930 to prevent acute angioedema attacks in patients with Type I and Type II HAE. Study NCT02586805. ClinicalTrials.gov Oct. 26, 2015. 7 pages.

[No Author Listed], HAE International, "Dyax presents Phase 1b data for DX-2930" dated Jun. 8, 2015. Last accessed from: https://haei.org/fa/dyax-presents/ on Jun. 27, 2025. 3 pages.

[No Author Listed], Health Canada has authorized Takhzyro(TM) (lanadelumab injection), a first-of-its-kind monoclonal antibody treatment for the prevention of hereditary angioedema (HAE) attacks. Takeda. Sep. 20, 2018. https://www.takeda.com/newsroom/shire-news-releases/2018/fv8oa5/ [last accessed Oct. 16, 2023]. 10 pages.

[No Author Listed], Long-term Safety and Efficacy Study of DX-2930 (SHP643) to Prevent Acute Angioedema Attacks in Patients With Type I and Type II HAE. NCT02741596. U.S. National Library of Medicine, ClinicalTrials.gov. Version 12: May 25, 2018. (Version 1 posted Apr. 15, 2016). https://clinicaltrials.gov/study/NCT02741596#more-information. 15 pages.

[No Author Listed], Prescribing Information for Takhzyro(TM). FDA. Aug. 24, 2018. https://www.accessdata.fda.gov/drugsatfda_docs/label/2018/761090s000lbl.pdf [last accessed Oct. 16, 2023]. 20 pages.

[No Author Listed], What is Hereditary Angioedema (HAE) ?. The US Hereditary Angioedema Association (HAEA). Last accessed from: https://www.haea.org/pages/p/what_is_hae on Jul. 25, 2025. 4 pages.

Abdel-Magid A.F., Plasma Kallikrein Inhibitors as Potential Treatment for Diabetic Macular Edema, Retinal Vein Occlusion, Hereditary Angioedema and Other Related Diseases. ACS Med Chem Lett. Jan. 17, 2023;14(2):129-130. doi: 10.1021/acsmedchemlett.2c00526.

Abdel-Salam et al., "Expression of mouse anticreatine kinase (MAK33) monoclonal antibody in the yeast *Hansenula polymorpha*", Appl. Microbiol. Biotechnol, vol. 56, p. 157-164 (2001).

Abuchowski et al., "Alteration of immunological properties of bovine serum albumin by covalent attachment of polyethylene glycol," J. Bio. Chem., 1977, vol. 252, pp. 3578-3581.

Abuchowski et al., "Cancer therapy with chemically modified enzymes, I., Antitumor properties of polyethylene glycol-asparaginase conjugates," Cancer Biochem. Biophys., 1984, vol. 7, pp. 175-186.

Abuchowski et al., "Effect of covalent attachment of polyethylene glycol on immunogenicity and circulating life of bovine," J. Biol. Chem., 1977, vol. 252, pp. 3582-3586.

Adams et al: "The role of viscosupplementation with hylan G-F 20 (Synvisc(R)) in the treatment of osteoarthritis of the knee: a Canadian multicenter trial comparing hylan G-F 20 alone, hylan G-F 20 with non-steroidal anti-inflammatory drugs (NSAIDs)and NSAIDs alone", Osteoarthritis and Cartilage, Bailliere Tindall, London, GB, vol. 3, No. 4, pp. 213-225, (Dec. 1, 1995).

Adelman et al., Proteolysis of Platelet Glycoprotein 1b by Plasmin Is Facilitated by Plasmin Lysine-Binding Regions, Blood, vol. 68 (6): 1280-1284, (Dec. 1986).

(56) References Cited

OTHER PUBLICATIONS

Albrecht et al., Elastase inhibition by the inter-alpha-trypsin inhibitor and derived inhibitors of man and cattle. Hoppe Seylers Z Physiol Chem. Dec. 1983;364(12):1703-8.
Albrecht et al., Kunitz-type proteinase inhibitors derived by limited proteolysis of the inter-alpha-trypsin inhibitor, IX. Isolation and characterization of the inhibitory parts of inter-alpha-trypsin inhibitors from several mammalian sera. Hoppe Seylers Z Physiol Chem. Dec. 1983;364(12):1697-702.
Almagro et al., Humanization of antibodies. Front Biosci. Jan. 1, 2008;13:1619-33. doi: 10.2741/2786.
Altschul et al. "Gapped BLAST and PSI-BLAST: a new generation of protein database search programs." (1997) Nucleic Acids Res. 25:3389-3402.
Anba et al., Improving the Stability of a Foreign Protein in the Periplasmic Space of *Escherichia coli*, Biochimie, vol. 70(6): 727-733, (1988).
Angliker et al., The Synthesis of Lysylflouromethanes and their Properties as Inhibitors of Trypsin, Plasmin and Cathepsin B, Biochemistry, 241:871-875, (1987).
Asano et al., "Effects of a nonpeptide bradykinin B2 receptor antagonist, FR167344, on different in vivo animal models of inflammation", Br J Pharmacol, vol. 122, p. 1436-1440 (1997).
Asano M. et al., Br J Pharmacol, vol. 122, p. 1436-1440 (1997).
Atherton et al., Peptide Synthesis. Part 2. Procedures for Solid Phase Synthesis using Nα-Fluorenylmethycarbonylamino-acids on Polyamide Supports. Synthesis of Substance P and of Acyl Carrier Protein 65-74 Decapeptide, J. Chem. Soc. Perkins Trans, 1:538-546, (1981).
Attwood, The Babel of Bioinformatics; Science, vol. 290, pp. 471-473 (2000).
Auerswald et al., Expression, Isolation and Characterization of Recombinant [Arg15, Glu52] Aprotinin, Bio. Chem. Hoppe-Seyler, 369:(Suppl)27-35 (1988).
Baba et al., States of Tyrosyl Residues and Circular Dichroism of Kunitz Trypsin Inhibitor, J. Biochem 65 (1):113-121 (1969).
Bagdasarian et al., Immunochemical studies of plasma kallikrein. J Clin Invest. Dec. 1974;54(6):1444-54.
Balduyck et al., Human Urinary Proteinase Inhibitor: Inhibitory Properties and Interaction with Bovine Trypsin, Bio. Chem. Hoppe-Seyler, vol. 366: 9-14, (1985).
Banerji et al., Effect of Lanadelumab Compared With Placebo on Prevention of Hereditary Angioedema Attacks: A Randomized Clinical Trial. JAMA. Nov. 27, 2018;320(20):2108-2121. doi: 10.1001/jama.2018.16773.
Banerji et al., Inhibiting Plasma Kallikrein for Hereditary Angioedema Prophylaxis. N Engl J Med. Feb. 23, 2017;376(8):717-728. doi: 10.1056/NEJMoa1605767.
Banerji et al., Lanadelumab 300mg every 2 weeks effectively prevented hereditary angioedema attacks in the help study. Ann Allerg Asthma Im. Nov. 1, 2018;121(5):S5.
Baneyx et al., "In Vivo Degradation of Secreted Fusion Proteins by the *Escherichia coli* Outer Membrane Protease OmpT", J. Bacteriol., 172:491-494, (1990).
Baneyx et al., Construction and Characterization of *Escherichia coli* Strains Deficient in Multiple Secreted Proteases: Protease III Degrades High-Molecular-Weight Substrates In Vivo, J Bacteriol., 173:2696-2703 (1991).
Basu et al., "Structure-function engineering of interferon-b-1b for improving stability, solubility, potency, immunogenicity, and pharmacokinetic properties by site-selective mono-PEGylation," Bioconjugate Chemistry, 2006, vol. 17, pp. 618-630.
Baumann, "A multi-level study of recombinant Pichia pastoris in different oxygen conditions", BMC Syst Biol. 4:141 (Oct. 22, 2010).
Bayes et al., "Gateways to Clinical Trials" Methods Find Exp. Clin. Pharmacol., vol. 28(3): pp. 185-206 (2006).
Beckmann et al., "Preparation of chemically 'mutated' aprotinin homologues by semisynthesis-P1 substitutions change inhibitory specificity," Eur. J. Biochem., vol. 176, pp. 675-682 (1988).
Beech et al., "Further characterisation of a thromboembolic model of stroke in the rat" Brain Res, vol. 895, p. 18-24 (2001).
Bendig, Humanization of Rodent Monoclonal Antibodies by CDR Grafting. Companion to Methods in Enzymology. 1995; 8:83-93.
Berge et al., "Pharmaceutical salts", J. Pharm. Sci. 66:1-19 (1977).
Bergthorsdottir et al., "Signals that initiate somatic hypermutation of B cell in vitro", J. Immunol., p. 166:2228 (2001).
Berndt et al., "Designed Replacement of an Internal Hydration Water Molecule in BPTI: Structural and Functional Implications of a Glycine-to-Serine Mutation," Biochemistry, 32: 4564-4570 (1993).
Bhoola et al., "Bioregulation of Kinins: Kallikreins, Kininogens and Kininases," Pharmacological Reviews, 44 :1-80 (1992).
Bird et al. "Single chain antigen binding proteins", Science 242:423-426 (1988).
Blaber et al., "Targeting kallikrein 6-proteolysis attenuates CNS inflammatory disease," FASEB J. May 2004;18(7):920-2. Epub Mar. 19, 2004.
Blijlevens et al., Palifermin (recombinant keratinocyte growth factor-1): a pleiotropic growth factor with multiple biological activities in preventing chemotherapy- and radiotherapy-induced mucositis. Ann Oncol. May 2007;18(5):817-26. Epub Oct. 9, 2006.
Bodanszky et al., The Practice of Peptide Synthesis (Springer-Verlag, New York, 1984).
Bork, "Powers and pitfalls in sequence analysis: the 70% hurdle," Genome Research, vol. 10, pp. 398-400 (2000).
Borregaard et al., "Granules of the human neutrophilic polymorphonuclear leukocyte," Blood, 1997, vol. 89, No. 10, pp. 3503-3521.
Bova et al., Lanadelumab Injection Treatment for The Prevention of Hereditary Angioedema (HAE): Design, Development and Place In Therapy. Drug Des Devel Ther. Oct. 22, 2019;13: 3635-3646. doi: 10.2147/DDDT.S192475.
Bowdish et al., "Yeast expression of a catalytic antibody with chorismate mutase activity.", J Biol Chem.; 266 (18):11901-8 (Jun. 25, 1991).
Bowen et al., 2010 International consensus algorithm for the diagnosis, therapy and management of hereditary angioedema. Allergy Asthma Clin Immunol. Jul. 28, 2010;6(1):24(1-13). doi: 10.1186/1710-1492-6-24.
Bowie et al. "Deciphering the message in protein sequences: tolerance to amino acid substitutions." Science 247:1306-1310 (1990).
Boyles, Novel Kallikrein Inhibitor Promising for HAE Prophylaxis, MedPage Today. Feb. 22, 2017 https://www.medpagetoday.com/pulmonology/generalpulmonary/63342.
Branden et al., "Prediction, Engineering, and Design of Protein," Introduction to Protein Structure, 1991, p. 247, Garland Publishing Inc., New York.
Breedveld, Therapeutic monoclonal antibodies. Lancet. Feb. 26, 2000;355(9205):735-40. Review.
Brenner, "Errors in genome annotation," Trends in Genetics, vol. 15, No. 4, pp. 132-133 (1999).
Brinkmann et al., "Design of an aprotinin variant with inhibitory activity against chymotrypsin and cathepsin G by recombinant DNA technology," Biol. Chem. Hoppe-Seyler, vol. 371, pp. 43-52 (1990).
Browne et al., "Expression of Recombinant Human Plasminogen and Aglycoplasminogen in HeLa Cells," GenBank, Accession No. M74220 (1991).
Broze et al., "Regulation of Coagulation by a Multivalent Kunitz-Type Inhibitor," Biochemistry, 29:7539-7546, (1990).
Brus et al., "Disease Severity Is Correlated with Plasma Clotting and Fibrinolytic and Kinin-Kallikrein Activity in Neonatal Respiratory Distress Syndrome," Pediatric Research, 41:120-127, (1997).
Buchan et al., "A new model of temporary focal neocortical ischemia in the rat", Stroke 23 (2): 273-9 (1992).
Budavari, ed., Merck index, 11th ed., ISBN 911910-28-X, entries 923, 1745, 2740, 7425, (1989).
Buras et al., "Animal models of sepsis: setting the stage", Nat Rev Drug Discov. 4(10):854-65 (2005).
Burrage et al., "Matrix metalloproteinases: role in arthritis," Frontiers in Bioscience, 2006, vol. 11, pp. 529-543.

(56) References Cited

OTHER PUBLICATIONS

Burton et al. "Human Antibody Effector Function", Adv. Immunol. 51:1-84 (1992).
Busse et al., Efficacy and safety of lanadelumab for prophylactic treatment in adolescents with hereditary angioedema (HAE). Feb. 2019;143(2): AB43.
Bygum et al., Disease Severity, Activity, Impact, and Control and How to Assess Them in Patients with Hereditary Angioedema. Front Med (Lausanne). Dec. 4, 2017;4:212. doi: 10.3389/fmed.2017.00212.
Cantor et al., "Elastin and Elastases in Lung Disease", Elastin and Elastases, Chapter 16, vol. II, pp. 159-168 (1989).
Carey et al., Advanced Organic Chemistry, 3rd Edition, Part B: Reactions and Synthesis, Plenum Press, New York: 678-686 (1990).
Carmichael, "Rodent models of focal stroke: size, mechanism, and purpose", NeuroRx 2: 396-409 (2005).
Carpenter et al., "Rational design of stable lyophilized protein formulations: theory and practice," Pharmaceutical Biotechnology, vol. 13, pp. 109-133 (2002).
Casati et al., Tranexamic acid compared with high-dose aprotinin in primary elective heart operations: effects on perioperative bleeding and allogeneic transfusions. J Thorac Cardiovasc Surg. Sep. 2000;120(3):520-7.
Casset et al., A peptide mimetic of an anti-CD4 monoclonal antibody by rational design. Biochem Biophys Res Commun. Jul. 18, 2003;307(1):198-205.
Cassim et al., "Kallikrein cascade and cytokines in inflamed joints," Pharmacology and Therapeutics, 2002, vol. 94, pp. 1-34.
Cernak, "Animal models of head trauma", NeuroRx. 2(3): 410-422 (2005).
Chen et al., "A model of focal ischemic stroke in the rat: reproducible extensive cortical infarction", Stroke 17 (4): 738-43 (1986).
Chen et al., "Establishment of an animal model of oral mucositis induced by conditioning regimen of haematopoietic stem cell transplantation" Zhonghua Kou Qiang Yi Xue Za Zhi. 42(11):672-6 (2007). (Abstract only).
Chen et al., "Refined 2-5 A X-ray Crystal Structure of the Complex Formed by Porcine Kallikrein A and the Bovine Pancreatic Trypsin Inhibitor—Crystallization, Patterson Search, Structure Determination, Refinement, Structure and Comparison with its Components and with the Bovine Trypsin-Pancreatic Trypsin Inhibitor Complex" J. Mol. Biol., 164:283-311 (1983).
Chen et al., Selection and analysis of an optimized anti-VEGF antibody: crystal structure of an affinity-matured Fab in complex with antigen. J Mol Biol. Nov. 5, 1999;293(4):865-81.
Chen et al., Solution Structure of a Kunitz-type Chymotrypsin Inhibitor Isolated from the Elapid Snake Bungarus Fasciatus, J. Biological Chemistry 276:45079-45087 (2001).
Chothia et al. "Canonical structures for the hypervariable regions of immunoglobulins." (1987) J. Mol. Biol. 196:901-917 (1987).
Chothia et al. "Structural Repertoire of the Human VH Segments", J. Mol. Biol. 227:799-817 (1992).
Chung et al., "Human plasma prekallikrein, a zymogen to a serine protease that contains four tandem repeats," GenBank, Accession #P03952 (1986).
Churg et al., "Proteases and emphysema," Curr. Opin. Pulm. Med., 2005, vol. 11, pp. 153-159.
Chyung et al., A phase 1 study investigating DX-2930 in healthy subjects. Ann Allergy Asthma Immunol. Oct. 2014;113(4):460-6.e2. doi: 10.1016/j.anai.2014.05.028. Epub Jun. 26, 2014.
Chyung et al., P289: Pharmacologic Modeling to Guide the DX-2930 Dosing Regimen in Investigating Long-Term Prophylaxis of Hereditary Angioedema. Ann Allergy Asthma Immunol. Nov. 2014;113(5): A106.
Colman et al., "Contact System: A Vascular Biology Modulator With Anticoagulant, Profibrinolytic, Antiadhesive, and Proinflammatory Attributes" Blood, 90, 3819-3843 (1997).
Colman et al., "The Plasma Kallikrein-Kinin System in Sepsis, Inflammatory Arthritis, and Enterocolitis" Clinical Reviews in Allergy and Immunology, vol. 16, pp. 365-384 (1998).
Colman et al., Hemostasis and Thrombosis Basic Principles and Clinical Practice, Chapter 1, 2nd Edition, 3-17 (1987).
Colman R. W., "Plasma and tissue Kallikrein in Arthritis and Inflammatory Bowel Disease", Immunopharmacology, Jan. 1, 1999, pp. 103-108, vol. 43, No. 2/03, Elsevier Science Publishers, BV.
Colman RW et al., "Activation of the kallikrein-kinin system in arthritis and enterocolitis in genetically susceptible rats: modulation by a selective plasma kallikrein inhibitor", Proceedings of the Association of American Physicians, Jan. 1, 1997, pp. 10-22, vol. 109, No. 1, Cambridge, MA US.
Cook et al., The human immunoglobulin VH repertoire. Immunol Today. May 1995;16(5):237-42.
Corpet, et al. "Recent improvements of the ProDom database of protein domain families" Nucl. Acids Res. 27:263-267 (1999).
Cumming et al., "Hemodynamic, Renal, and Hormonal Aprotinin in an Ovine Model of Septic Shock," Critical Care Medicine, 20:1134-1139 (1992).
Cunningham et al., "Structural and functional characterization of tissue factor pathway inhibitor following degradation by matrix metalloproteinase-8," Biochem. J., 2002, vol. 367, pp. 451-458.
Current Protocols in Molecular Biology, John Wiley & Sons, N.Y. (1989) 6.3.1-6.3.6.
Currie et al., "Design and Synthesis of a Bicyclic Non-Peptide β-Bend Mimetic of Enkephalin," Tetrahedron, 49:3489-3500 (1993).
Dai et al., Role of Bradykinin in the Pathogenesis of Allergic Diseases. Chin J Allergy Clin Immunol. Dec. 30, 2014;8(4):306-11.
De Agostini et al., Human plasma kallikrein and C1 inhibitor form a complex possessing an epitope that is not detectable on the parent molecules: demonstration using a monoclonal antibody. Proc Natl Acad Sci U S A. Aug. 1985;82(15):5190-3.
De Campos et al., "Antioedematogenic and antinociceptive actions of NPC 18521, a novel bradykinin B2 receptor antagonist", Eur J Pharmacol. 316, 277-286 (1996).
De Haard et al. "A large non-immunized human Fab fragment phage library that permits rapid isolation and kinetic analysis of high affinity antibodies". J. Biol. Chem 274:18218-30, (1999).
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
De Wildt et al. "Antibody arrays for high-throughput screening of antibody-antigen interactions", Nat. Biotechnol. 18:989-994 (2000).
De Wildt et al., "Characterization of human variable domain antibody fragments against the U1 RNA-associated A protein, selected from a synthetic and patient-derived combinatorial V gene library" Eur J Immunol. 26(3):629-39 (1996).
Debiopharm brochure, "Engineering protein inhibitor of human neutrophil elastase EPIO-hNE4 (DX-890)," Dated Oct. 2004, printed from www.debio.com/e/pdf/fiche.sub.--epi.sub.--hne4.sub.--e.pdf.
Dela Cadena et al., "Role of Kallikrein-Kinin System in the Pathogenesis of Bacterial Cell Wall-Induced Inflammation and Enterocolitis," Transact. Assoc. Am. Physicians, 105:229-237 (1992).
Dela Cadena, et al., "Inhibition of Plasma Kallikrein Prevents Peptidoglycan-Induced Arthritis in the Lewis Rat," FASEB Journal, 9:446-452 (1995).
Delacourt et al., "Protection against acute lung injury by intravenous or intratracheal pretreatment with EPI-HNE-4, a new potent neutrophil elastase inhibitor," Am. J. Respir. Cell Mol. Biol., Mar. 26, 2002, vol. 26, No. 3, pp. 290-297.
Delaria et al., "Characterization of placental bikunin, a novel human serine protease inhibitor," J. Biological Chemistry, May 2, 1997, vol. 272, No. 18, pp. 12209-12214.
Delgado et al., "The uses and properties of PEG-linked proteins," Critical Review in Therapeutic Drug Carrier Systems, 1992, vol. 9, No. 3,4, pp. 249-304.
Deng et al., "Production of recombinant humanized anti-HBsAg Fab antibody by fermentation" Sheng Wu Gong Cheng Xue Bao, 20(5):800-4 (Sep. 2004) (Abstract Only).
Dennis et al., "Kunitz Domain Inhibitors of Tissue Factor-Factor VIIa (I. Potent Inhibitors Selected from Libraries by Phage Display)," Journal of Biological Chemistry 269:22129-22136 (1994).

(56) References Cited

OTHER PUBLICATIONS

Dennis et al., "Kunitz Domain Inhibitors of Tissue Factor-Factor Vila (II. Potent and Specific Inhibitors by Competitive Phage Selection)," Journal of Biological Chemistry, 269:22137-22144 (1994).
Dennis et al., "Potent and Selective Kunitz Domain Inhibitors of Plasma Kallikrein Designed by Phage Display," J. Biol. Chem., 270:25411-25417 (1995).
Devani et al., "Kallikrein-kinin system in inflammatory bowel disease: intestinal involvement and correlation with the degree of tissue inflammation," Digestive and Liver Disease, 2005, vol. 37, pp. 665-673.
Dhalluin et al., "Structural, kinetic, and thermodynamic analysis of the binding of the 40kDa PEG-interferon-a-2a and its individual positional isomers to the extracellular domain of the receptor IFNAR2," Bioconjugate Chemistry, 2005, vol. 16, pp. 518-527.
Diaz et al., "The Design of Water Soluble β-Sheet Structure Based on a Nucleation Strategy," Tetrahedron, 49:3533-3545 (1993).
Dimaio et al., "A New Class of Potent Thrombin Inhibitors That Incorporates a Scissile Pseudopeptide Bond," FEBS Lett, 282(1):47-52 (1991).
Dittmar et al., "External carotid artery territory ischemia impairs outcome in the endovascular filament model of middle cerebral artery occlusion in rats" Stroke 34: 2252-7 (2003).
Dittmar et al., "Fischer-344 rats are unsuitable for the MCAO filament model due to their cerebrovascular anatomy" J Neurosci Methods 156: 50 (2006).
Doerks et al., "Protein annotation: detective work for function prediction," Trends in Genetics, vol. 14, No. 6, pp. 248-250 (1998).
Donnelly et al., "Therapy for chronic obstructive pulmonary disease in the 21st century," Drugs, 2003, vol. 63, pp. 1973-1998.
Dragosits et al., "The effect of temperature on the proteome of recombinant *Pichia pastoris*", J Proteome Res. Mar. 2009;8(3):1380-92. 16 pages.
Dragosits et al., "The response to unfolded protein is involved in osmotolerance of *Pichia pastoris*" BMC Genomics. Mar. 26, 2010;11:207.
Druar et al., Analysis of the expressed heavy chain variable-region genes of Macaca fascicularis and isolation of monoclonal antibodies specific for the Ebola virus' soluble glycoprotein Immunogenetics, 57(10):730-8 (2005).
Dufton, "Protein inhibitors and dendrotoxins," Eur. J. Biochem., vol. 153, pp. 647-654. (1985).
Edqvist, et al., "Production of functional IgM Fab fragments by *Saccharomyces cerevisiae*", J Biotechnol 20 (3):291-300 (1991).
Eigenbrot et al., "Structural Effects Induced by Removal of a Disulfide-Bridge: The X-ray Structure of the C30A/C51A Mutant of Basic Pancreatic Trypsin Inhibitor at 1.6 A," Protein Engineering, 3:591-598 (1990).
Ellis et al., "The Urokinase Receptor: Involvement in Cell Surface Proteolysis and Cancer Invasion," Ann. NY. Acad. Sci., 667:13-31 (1992).
Enzon Pharmaceuticals, Macromolecular Engineering Technologies, 2004, pp. 1-14.
Falquet et al., "The Prosite database, its status in 2002." (2002) Nucleic Acids Res. 30:235-238.
Faucette et al., Biomarker Assay for the detection of contact system activation. Ameri Soc. Hemato. Nov. 15, 2013; 122(21):2347. 55th Annual Meeting of the American Society-of-Hematology. New Orleans, LA, USA. Dec. 7-10, 2013.
Feener, Plasma kallikrein and diabetic macular edema. Curr Diab Rep. Aug. 2010;10(4):270-5. doi: 10.1007/s11892-010-0127-1.
Ferrara et al., Recombinant renewable polyclonal antibodies. MAbs. 2015;7(1):32-41. doi: 10.4161/19420862.2015.989047.
Fidler et al., "The Implications of Angiogenesis for the Biology and Chemistry of Cancer Metastasis," Cell, 79:185-188 (1994).
Fields et al., "Solid Phase Peptide Synthesis Utilizing 9-fluorenylmethocarbonyl Amino Acids," Int. J. Peptide Protein Research, 35:161-214 (1990).
Fife et al., "Cartilage matrix glycoprotein is present in serum in experimental canine osteoarthritis" J Clin Invest. 84(5):1432-1439 (1989).
Fink et al., Cellular expression of plasma prekallikrein in human tissues. Biol Chem. Sep. 2007;388(9):957-63.
Fraedrich et al., "Reduction of Blood Transfusion requirement in Open Heart Surgery by Administration of High Doses of Aprotinin~Preliminary Results," Thorac Cardiovasc Surgeon, 37:89-91 (1989).
Frank, 8. Hereditary angioedema. J Allergy Clin Immunol. Feb. 2008;121(2 Suppl): S398-401; quiz S419. doi: 10.1016/j.jaci.2007.07.057.
Frank et al., Management of Children With Hereditary Angioedema Due to C1 Inhibitor Deficiency. Pediatrics. Nov. 2016;138(5):e20160575(1-11). doi: 10.1542/peds.2016-0575.
Fredrich et al., "A new animal model of venous thrombosis in rats with low flow conditions in the venous blood stream" Blood Coagul Fibrinolysis. 5(2):243-8 (1994).
Freidinger et al., "Protected Lactam-Bridged Dipeptides for Use as Conformational Constraints in Peptides," Journal of Organic Chemistry, 47:104-109 (1982).
Fries et al., "Inter-a-inhibitor, hyaluronan and inflammation," Acta Biochimica Polonica, 2003, vol. 50, No. 3, pp. 735-742.
Frisbie, "An animal model for venous thrombosis and spontaneous pulmonary embolism." Spinal Cord 43, 635-639 (2005).
Galeffi et al., "Functional expression of a single-chain antibody to ErbB-2 in plants and cell-free systems" J Transl Med. Sep. 29, 2006;4:39. 13 pages.
Gao et al., Extracellular carbonic anhydrase mediates hemorrhagic retinal and cerebral vascular permeability through prekallikrein activation. Nat Med. Feb. 2007;13(2):181-8. Epub Jan. 28, 2007.
Gardell et al., "The Search for the Ideal Thrombolytic Agent: Maximize the Benefit and Minimize the Risk," Toxicologic Pathology, 21(2):190-198 (1993).
Gasser et al., "Engineering of *Pichia pastoris* for improved production of antibody fragments" Biotechnol Bioeng. Jun. 5, 2006;94(2):353-61.
GenBank Submission; NIH/NCBI, Accession No. NM_008455.2 (GI: 236465804): "Plasma kallikrein precursor", GenBank Record created on Dec. 29, 2010.
GenBank Submission; NIH/NCBI, Accession No. NM_012725.2 (GI:162138904): "Plasma kallikrein precursor", GenBank Record created on Dec. 26, 2010.
GenBank Submission; NIH/NCBI, Accession No. NP_000418.2 (GI:109255251): "loricrin", GenBank Record created on Nov. 3, 2010.
GenBank Submission; NIH/NCBI, Accession No. NP_000883.2 (GI: 78191798): "Plasma kallikrein preproprotein", GenBank Record created on Nov. 21, 2010.
GenBank Submission; NIH/NCBI, Accession No. NP_000892 (GI: 158508572): "mineralocorticoid receptor isoform 1", GenBank Record created on Dec. 27, 2010.
GenBank Submission; NIH/NCBI, Accession No. NP_005850.1 (GI:5032007): "transcriptional activator protein Pur-alpha", GenBank Record created on Dec. 28, 2010.
GenBank Submission; NIH/NCBI, Accession No. NP_006228.3 (GI:110347449): "POU domain, class 4, transcription factor 1", GenBank Record created on Dec. 27, 2010.
GenBank Submission; NIH/NCBI, Accession No. NP_009060.2 (GI:22547197): "zinc finger protein ZIC 2", GenBank Record created on Dec. 24, 2010.
GenBank Submission; NIH/NCBI, Accession No. NP_031393.2 (GI:21396480): "RNA-binding protein Raly isoform 2", GenBank Record created on Dec. 25, 2010.
GenBank Submission; NIH/NCBI, Accession No. NP_032481.2 (GI: 236465805): "Plasma kallikrein precursor", GenBank Record created on Dec. 29, 2010.
GenBank Submission; NIH/NCBI, Accession No. NP_036857.2 (GI:162138905): "Plasma kallikrein precursor", GenBank Record created on Dec. 26, 2010.
GenBank Submission; NIH/NCBI, Accession No. NP_056932.2 (GI:153791670): "Plasma kallikrein preproprotein", GenBank Record created on Dec. 27, 2010.

(56) References Cited

OTHER PUBLICATIONS

GenBank Submission; NIH/NCBI, Accession No. NP_061856.1 (GI:9506713): "H/ACA ribonucleoprotein complex subunit 1", GenBank Record created on Dec. 24, 2010.
GenBank Submission; NIH/NCBI, Accession No. NP_065104.1 (GI:9966841): "cell death regulator Aven", GenBank Record created on Dec. 26, 2010.
GenBank Submission; NIH/NCBI, Accession No. NP_115818.2 (GI:53829370): "neuralized-like protein 4 isoform 1", GenBank Record created on Dec. 27, 2010.
GenBank Submission; NIH/NCBI, Accession No. NP_476429.2 (GI:109148552): "keratin, type II cytoskeletal 3 ", GenBank Record created on Dec. 24, 2010.
GenBank Submission; NIH/NCBI, Accession No. NP_631961.1 (GI:21327701): "TATA-binding protein-associated factor 2N isoform 1", GenBank Record created on Dec. 25, 2010.
GenBank Submission; NIH/NCBI, Accession No. NP_787059.2 (GI:40068462): "At-rich interactive domain-containing protein 1B isoform 3", GenBank Record created on Mar. 4, 2010.
GenBank Submission; NIH/NCBI, Accession No. XP_376532.2 (GI:51465288): "Predicted: KIAA0408", GenBank Record created on Aug. 19, 2004.
Gerriets et al., "Complications and pitfalls in rat stroke models for middle cerebral artery occlusion: a comparison between the suture and the macrosphere model using magnetic resonance angiography", Stroke 35: 2372-2377 (2004).
Gerriets et al., "The macrosphere model: evaluation of a new stroke model for permanent middle cerebral artery occlusion in rats" J Neurosci Methods 122: 201-11 (2003).
Girard et al., "Functional Significance of the Kunitz-type Inhibitory Domains of Lipoprotein-Associated Coagulation Inhibitor," Nature, 338:518-520 (1989).
Girard et al., "Structure of the Human Lipoprotein-associated Coagulation Inhibitor Gene," The Journal of Biological Chemistry, 266:5036-5041 (1991).
Goldenberg et al., "Circular and circularly permuted forms of bovine pancreatic trypsin inhibitor," J. Mol. Biol., vol. 165, pp. 407-413 (1983).
Gomez-Jorge et al., "The Double-Tuck Model: A New Animal Model of Arterial Thrombosis" J. Vasco Inter. Rad. 9 (4): 633-638 (1998).
Gonzalez-Quevedo et al., The Synthetic Kunitz Domain Protein DX88 to Treat Angioedema in Patients with Hereditary Angioedema, International Immunopharmacology 2(9):1318 Abstract 205 (2002).
Goodson et al., "Site-directed PEGylation of recombinant interleukin-2 at its glycosylation site," Bio Technology, 1990, vol. 8, pp. 343-346.
Gouzy et al. "Whole genome protein domain analysis using a new method for domain clustering" (1999) Computers and Chemistry 23:333-340.
Graham et al., "Animal models of ischemic stroke: balancing experimental aims and animal care", Comp Med 54: 486-496 (2004).
Green, Antibody engineering via genetic engineering of the mouse: XenoMouse strains are a vehicle for the facile generation of therapeutic human monoclonal antibodies. J Immunol Methods. Dec. 10, 1999;231(1-2):11-23.
Greilich et al., "Antifibrinolytic therapy during cardiopulmonary bypass reduces proinflammatory cytokine levels: a randomized, double-blind, placebo-controlled study of εaminocaproic acid and aprotinin," J. Thorac. Cardiovasc. Surg., 2003, vol. 126, pp. 1498-1503.
Gribskov et al. "Profile analysis." (1990) Meth. Enzymol. 183:146-159.
Gribskov et al. "Profile analysis: detection of distantly related proteins." (1987) Proc. Natl. Acad. Sci. USA 84:4355-4358.
Grimaldi et al., "Trasylol in the treatment of acute arthritis due to microcrystals," Reumatismo, vol. 23, No. 5, pp. 217-221, (1971) (Abstract only).
Gullberg et al., "Biosynthesis, processing and sorting of neutrophil proteins: insight into neutrophil granule development," Eur. Journal of Haematology, 1997, vol. 58, pp. 137-153.
Guzman et al. "Mono-iodoacetate-induced histologic changes in subchondral bone and articular cartilage of rat femorotibial joints: an animal model of osteoarthritis." Toxicol Pathol. 31(6):619-24 (2003).
Hagihara et al., "Screening for stable mutants with amino acid pairs substituted for the disulfide bond between residues 14 and 38 of bovine pancreatic trypsin inhibitor (BPTI)," The Journal of Biological Chemistry, 2002, vol. 277, No. 52, pp. 51043-51048.
Han et al., Increased Vascular Permeability in C1 Inhibitor-Deficient Mice Mediated by the Bradykinin Type 2 Receptor, J. Clinical Investigation 109(8):1057-1063 (2002).
Han, Reversal of the Increased Vascular Permeability in C1 Inhibitor Deficient Mice: Therapeutic Approaches, International Immunopharmacology 2(9):1315 Abstract 176 (2002).
Hanes et al., "Picomolar affinity antibodies from a fully synthetic naive library selected and evolved by ribosome display" Nat Biotechnol. 18:1287-92 (2000).
Hanes et al., "Selecting and evolving functional proteins in vitro by ribosome display" Methods Enzymol. 328:404-30 (2000).
Harvey et al., "Engineering of recombinant antibody fragments to methamphetamine by anchored periplasmic expression" J Immunol Methods. Jan. 20, 2006;308(1-2):43-52. Epub Nov. 22, 2005.
Herter et al., "Hepatocyte growth factor is a preferred in vitro substrate for the human hepsin, a membrane-anchored serine protease implicated in prostate and ovarian cancers," Biochem. J., 2005, vol. 390, pp. 125-136.
Hoet et al., "Generation of high-affinity human antibodies by combining donor-derived and synthetic complementarity-determining-region diversity" Nat Biotechnol. 23(3)344-8 (2005).
Holliger et al., Engineered antibody fragments and the rise of single domains. Nat Biotechnol. Sep. 2005;23(9):1126-36.
Hoogenboom et al., "Antibody phage display technology and its applications" Immunotechnology 4:1-20 (1998).
Hoogenboom et al., "Natural and designer binding sites made by phage display technology" Immunol Today 2:371-8 (2000).
Hoover et al., "Amino Acids of the Recombinant Kringle 1 Domain of Human Plasminogen that Stabilize Its Interaction w-Amino Acids," Biochemistry, 32:10936-10943 (1993).
Hortin et al., "Allosteric Changes in Thrombin's Activity Produced by peptides Corresponding to Segments of Natural Inhibitors and Substrates," The Journal of Biological Chemistry, 266:6866-6871 (1991).
Horwitz et al., "Secretion of functional antibody and Fab fragment from yeast cells," Proc Natl Acad Sci U S A. 85 (22):8678-82 (Nov. 1988).
Hostomsky et al., "Solid Phase Assembly of Cow Colostrum Trypsin Inhibitor Gene," Nucleic Acids Research, 15:4849-4856 (1987).
Huang et al., "Kinetics of factor Xa inhibition by tissue factor pathway inhibitor," The Journal of Biological Chemistry, 1993, vol. 268, No. 36, pp. 26950-26955.
Huang et al., "Novel peptide inhibitors of angiotensin-converting enzyme 2," The Journal of Biological Chemistry, 2003, vol. 278, No. 18, pp. 15532-15540.
Huge et al., "A model to investigate postoperative ileus with strain gauge transducers in awake rats" J Surg Res. 74 (2):112-8 (1998). Abstract Only.
Huston et al., "Protein engineering of antibody binding sites: Recovery of specific activity in anti-digoxin single-chain Fv analogue produced in *Escherichia coli*", Proc. Natl. Acad. Sci. USA 85:5879-5883 (1988).
Hynes et al., X-ray crystal structure of the protease inhibitor domain of Alzheimer's amyloid beta-protein precursor. Biochemistry, 29:10018-10022 (1990).
Iaboni et al., Impact of lanadelumab in hereditary angioedema: a case series of 12 patients in Canada. Allergy Asthma Clin Immunol. Jul. 23, 2021;17(1):78. doi: 10.1186/s13223-021-00579-6.

(56) References Cited

OTHER PUBLICATIONS

Janeway et al., The interaction of the antibody molecule with specific antigen. Immunobiology: The Immune System in Health and Disease.5th edition. New York: Garland Science; 2001. NCBI Bookshelf. 5 pages.

Jefferis et al., "IgG-Fc-mediated effector functions: Molecular definition of interaction site for effector ligands and the role of glycosylation," Immunol. Rev. 163:59-76, (1998).

Jones et al., "Severe prekallikrein deficiency associated with homozygosity for an Arg94Stop nonsense mutation" Br J Haematol, 2004. 127(2): p. 220-3.

Jonkam et al., "Effects of the bradykinin B2 receptor antagonist icatibant on microvascular permeability after thermal injury in sheep" Shock, 28:704-709 (2007).

Jorg et al., Kinetic analysis of plasminogen activation by purified plasma kallikrein. Thromb Res. Aug. 1, 1985;39(3):323-31.

Jostock et al., "Rapid generation of functional human IgG antibodies derived from Fab-on-phage display libraries" J. Immunol. Methods, 289(1-2):65-80 (2004).

Kabat et al. Sequences of Proteins of Immunological Interest, Fifth Edition, U.S. Dept. of Health and Human Services, NIH Publication No. 91-3242 (1991).

Kantor et al., "The experimental animal models for assessing treatment of restenosis" Cardiovasc Radiat Med. 1 (1):48-54 (1999).

Kaplan et al., A prealbumin activator of prekallikrein. 3. Appearance of chemotactic activity for human neutrophils by the conversion of human prekallikrein to kallikrein. J Exp Med. Jan. 1972;135(1):81-97.

Katre et al., "Chemical modification of recombinant interleukin 2 by polyethylene glycol increases its potency in the murine Meth A sarcoma model," PNAS USA, 1987, vol. 84, pp. 1487-1491.

Katre et al., "Immunogenicity of recombinant IL-2 modified by covalent attachment of polyethylene glycol," J. Immunol., 1990, vol. 144, pp. 209-213.

Katz et al., "Animal models of vasculitides" Clin Rev Allergy Immunol. 35(1-2): 11-8 (2008).

Kaufman et al., "Amplification and expression of sequences cotransfected with a modular dihydrofolate reductase complementary dna gene", Mol. Biol. 159:601 621 (1982).

Kelly et al., "Diabetes insipidus in uricase-deficient mice: a model for evaluating therapy with poly(ethylene glycol)-modified," J. Am. Soc. Nephrol., 2001, vol. 12, pp. 1001-1009.

Kemp et al., "Synthesis of Peptide-Functionalized Daicylaminoepinodolidiones," Tetrahedron Letters, 29:5077-5080 (1988).

Kenniston et al., Discovery and Characterization of a Highly Specific Antibody Inhibitor of Plasma Kallikrein. Blood 2013; 122: 1067. Abstract only.

Kenniston et al., Inhibition of plasma kallikrein by a highly specific active site blocking antibody. J Biol Chem. Aug. 22, 2014;289(34):23596-608. doi: 10.1074/jbc.M114.569061. Epub Jun. 26, 2014.

Kettleborough et al., Humanization of a mouse monoclonal antibody by CDR-grafting: the importance of framework residues on loop conformation. Protein Eng. Oct. 1991;4(7):773-83.

Kido et al., "Kunitz-type Protease Found in Rat Mast Cells," J. Biol. Chem. 263(34):18104-18107 (1988).

Kido et al., "Protease Specificity of Kunitz Inhibitor Domain of Alzheimer's Disease Amyloid Protein Precursor," Biochem Biophys Res Commun. Mar. 16, 1990;167(2):716-21.

Kirchhofer et al., "Hepsin activates pro-hepatocyte growth factor and is inhibited by hepatocyte growth factor activator-1B (HAI-1B) and HAI-2," FEBS Letters, 2005, vol. 579, pp. 1945-1950.

Kirchhoff et al., "A Major Human Epididymis-Specific cDNA Encodes a Protein with Sequence Homology to Extracellular Proteinase Inhibitors," Biology of Reproduction, 45:350-357 (1991).

Kline et al. "Hirulog Peptides with Scissile Bond Replacements Resistant to Thrombin Cleavage," Biochem. Biophys. Res. Comm., 177:1049-1055 (1991).

Knappik et al., "Fully synthetic human combinatorial antibody libraries (HuCAL) based on modular consensus frameworks and CDRs randomized with trinucleotides," J. Mol. Biol. 296:57-86 (2000).

Ko et al., "Biotransformation of uridine monophosphate (UMP) and glucose to uridine diphosphate-glucose (UDPG) by Candida saitoana KCTC7249 cells." Appl Biochem Biotechnol.; 60(1):41-8 (Jul. 1996).

Kobayashi et al., "Amended structure of side chains in a cell wall mannan from *Candida albicans* serotype A strain grown in yeast extract—Sabouraud liquid medium under acidic conditions: detection of the branched side chains corresponding to antigenic factor 4.", FEMS Microbiol Lett.; 152(2):235-42 (Jul. 15, 1997).

Koizumi et al., Experimental studies of ischemic brain edema. 1. A new experimental model of cerebral embolism in rats in which recirculation can be introduced in the ischemic area. Jpn J Stroke 1986;8:1-8.

Kozyr et al., "Production of DNA-hydrolyzing antibody BV04-01 Fab fragment in methylotrophic yeast *Pichia pastoris*" Mol Biol (Mosk). Nov.-Dec. 2004;38(6):1067-75.

Krogh et al. "Hidden Markov models in computational biology. Applications to protein modeling." (1994) J. Mol. Biol. 235:1501-1531. O.

Kuno et al., "Possible involvement of neutrophil elastase in impaired mucosal repair in patients with ulcerative colitis," Journal of Gastroenterology, 2002, vol. 37, Supple XIV, pp. 22-32.

Kurjan et al., Structure of a yeast pheromone gene (MF alpha): a putative alpha-factor precursor contains four tandem copies of mature alpha-factor. Cell. Oct. 1982;30(3):933-43.

Lamminmaki et al., Crystal structure of a recombinant anti-estradiol Fab fragment in complex with 17beta-estradiol. J Biol Chem. Sep. 28, 2001;276(39):36687-94. Epub Jul. 12, 2001.

Laskowski et al., "Inhibitors with Class-Specific Reactive Sites," Ann. Rev. Biochem., 49:593-626 (1980).

Leatherbarrow et al., "Design of a Small Peptide-Based Proteinase Inhibitor by Modeling the Active-Site Region of Barley Chymotrypsin Inhibitor 2," Biochemistry, 30:10717-10721 (1991).

Lederman et al., A Single Amino Acid Substitution in a Common African Allele of the CD4 Molecule Ablates Binding of the Monoclonal Antibody, OKT4. Molecular Immunology. 1991;28(11):1171-1181.

Leeb-Lundberg et al. "International union of pharmacology. XLV. Classification of the kinin receptor family: from molecular mechanisms to pathophysiological consequences", (2005) Pharmacol Rev 57, 27-77.

Leonetti et al., "Increasing immunogenicity of antigens fused to Ig-binding proteins by cell surface targeting," The Journal of Immunology, 1998, vol. 160, pp. 3820-3827.

Levy et al., The therapeutic potential of a kallikrein inhibitor for treating hereditary angioedema. Expert Opin Investig Drugs. Sep. 2006;15(9):1077-90.

Ley et al., "Obtaining a Family of High-Affinity, High Specificity Protein Inhibitors of Plasmin and Plasma Kallikrein," Molecular Diversity, 2:119-124, (1996).

Li et al., β-Endorphin omission analogs: Dissociation of immunoreactivity from other biological activities. Proc. Natl. Acad. Sci. USA. Jun. 1980;77(6):3211-3214.

Lilla et al., "Active plasma kallikrein localizes to mast cells and regulates epithelial cell apoptosis, adipocyte differentiation, and stromal remodeling during mammary gland involution" J Biol Chem. 284(20):13792-13803 (2009).

Liu et al., Plasma kallikrein-kinin system and diabetic retinopathy. Biol Chem. Mar. 2013;394(3):319-28. doi: 10.1515/hsz-2012-0316. Author manuscript.

Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

Lohmann et al., Plasmin- and Plasminogen-Activator Inhibitors after Excimer Laser Photorefractive Keratectomy: New Concept in Prevention of Postoperative Myopic Regression and Haze, Refractive and Corneal Surgery, 9:300-302, (1993).

(56) References Cited

OTHER PUBLICATIONS

Longa et al., "Reversible middle cerebral artery occlusion without craniectomy in rats" Stroke 20 (1): 84-91 (1989).
Lucas et al., "The Binding of Human Plasminogen to Fibrin and Fibrinogen," J. Biol. Chem., 258:4249-4256 (1983).
Lumry et al., Interim Results of EDEMA2, A Multicenter, Open-Label, Repeat-Dosing Study of Intravenous and Subcutaneous Administration of Ecallantide (DX-88) in Hereditary Angioedema. J. Allergy and Clinical Immunology 117(2) (Suppl. 1):S179 Abstract699 (2006).
Lumry et al., Subcutaneous self-administration of lanadelumab for prophylactic treatment in patients with hereditary angioedema (HAE). Ann Allerg Asthma Im. Nov. 2018;121(5):S57.
MacCallum et al., Antibody-antigen interactions: contact analysis and binding site topography. J Mol Biol. Oct. 11, 1996;262(5):732-45.
MacGilchrist, "Effect of the Serine Protease Inhibitor, Aprotinin, on Systemic Haemodynamics and Renal Function in Patients with Hepatic Cirrhosis and Ascites," Clin. Sci., 87:329-335 (1994).
MacGinnitie AJ. Pediatric hereditary angioedema. Pediatr Allergy Immunol. Aug. 2014;25(5):420-7. doi: 10.1111/pai.12168. Epub Dec. 9, 2013.
Magklara et al., "Characterization of the enzymatic activity of human kallikrein 6: autoactivation, substrate specificity and regulation by inhibitors," Biochem. Biophys. Res. Commun., Aug. 8, 2003, vol. 307, No. 4, pp. 948-955, Abstract Only.
Mann et al., Hemostasis and Thrombosis, Chapter 10, 2nd Edition, Basic Principles and Clinical Practice: 148-161 (1987).
Mannucci, "Hemostatic Drugs" New England Journal of Medicine, Drug Therapy, 339(4):245-253 (1998).
March, Advanced Organic Chemistry, 3rd Edition, Reactions, Mechanisms, and Structure, John Wiley and Sons, New York: 396-398; 1057-1060; 1099-1100 (1985).
Markland et al., "Iterative Optimization of High-Affinity Protease Inhibitors Using Phage Display. 1. Plasmin," Biochemistry, 35:8045-8057 (1996).
Markland et al., "Iterative Optimization of High-Affinity Protease Inhibitors Using Phage Display. 2. Plasma Kallikrein and Thrombin," Biochemistry 35(24):8058-67 (1996).
Markland et al., "Selection for Protease Inhibitors Using Bacteriophage Display," Methods Enzymol., 267:28-51 (1996).
Markland, Cell. Biochem. Supp., 1994, O, vol. 18D, pp. 157, Abstract S 331.
Martin et al., "Animal models of neuropathic pain" Methods Mol Med. 84:233-42 (2003).
Mathews et al., Biochemistry, The Benjamin Cummins Publishing Co., Inc. Redwood City CA: 208-212 (1990).
Mattheakis et al. "An in vitro polysome display system for identifying ligands from very large peptide libraries" Proc. Natl. Acad. Sci. USA 91:9022 (1994).
Maxfield et al., "Conformation of poly(ethylene oxide) in the solid state, melt and solution measured by Raman scattering," Polymer, 1975, vol. 16, pp. 505-509.
Mayzel-Oreg, "Microsphere-induced embolic stroke: an MRI study" Magn Reson Med 51: 1232-8 (2004).
McCarty, "Crystal-induced inflammation of the joints," Annual Reviews of Medicine, vol. 21, pp. 357-366 (1970).
McConnell et al., "New Leupeptin Analogues: Synthesis and Inhibition Data," J. Med. Chem., 33:86-93 (1990).
Merriam-Webster reference for the term "prevent." web date: 2010. 2 pages.
Merrifield, "Solid Phase Peptide Synthesis. I. The Synthesis of a Tetrapeptide," Am. Chem. Soc. 85:2149-2154 (1963).
Migliore et al: "Open pilot study of ultrasound-guided intra-articular injection of hylan G-F 20 (Synvisc) in the treatment of symptomatic hip osteoarthritis", Clinical Rheumatology; Journal of the International League of Associations for Rheumatology, Springer-Verlag, LO, vol. 24, No. 3, pp. 285-289 (Jun. 1, 2005).
Mine et al., "Structural mechanism for heparin-binding of the third Kunitz domain of human tissue factor pathway inhibitor," Biochemistry, 2002, vol. 41, pp. 78-85.
Miyajima et al., Secretion of mature mouse interleukin-2 by *Saccharomyces cerevisiae*: use of a general secretion vector containing promoter and leader sequences of the mating pheromone alpha-factor. Gene. 1985;37(1-3):155-61.
Molineux, "Pegylation: engineering improved pharmaceuticals for enhanced therapy," Cancer Treatment Reviews, 2002, vol. 28, pp. 13-16.
Monteseirin et al., "Plasma Kallikrein Amidolytic Activity in Bronchial Asthma," Allergol. Immunopathol., (Madr)., 20:211-214 (1992).
Moreland, "Intra-articular hyaluronan (hyaluronic acid) and hylans for the treatment of osteoarthritis: mechanisms of action," Arthritis Res. Ther, 2003, vol. 5, pp. 54-67.
Morishita et al., "Novel factor Xa and plasma kallikrein inhibitory—activities of the second Kunitz-type inhibitory domain of urinary trypsin inhibitor" Thromb Res, 73(3-4): p. 193-204 (1994).
Morrison "Transfectomas provide novel chimeric antibodies." (1985) Science 229:1202-1207.
Mould et al., Pharmacokinetics and pharmacodynamics of monoclonal antibodies: concepts and lessons for drug development. BioDrugs. Feb. 1, 2010;24(1):23-39. doi: 10.2165/11530560-000000000-00000.
Murkin et al., "Aprotinin significantly decreases bleeding and transfusion requirements in patients receiving aspirin and undergoing cardiac operations," J. Thorac. Cardiovasc. Surg., vol. 107, pp. 554-561 (1994).
Nadkarni et al., "Optimization of a mouse recombinant antibody fragment for efficient production from *Escherichia coli*" 2007 Protein Expr Purif 52(1):219-29.
Naess et al., "Effects of a Combined Drug Regimen on Tumour Necrosis Factor and Plasma Kallikrein Activity in Experimental Endotoxaemia," Eur. J. Surg., 160:77-86 (1994).
Nagai et al., Bicyclic turned dipeptide (BTD) as a β-turn mimetic; its design, synthesis and incorporation into bioactive peptides Tetrahedron, 49:3577-3592 (1993).
Nagai et al., Synthesis of a bicyclic dipeptide with the shape of β-turn central part. Tetrahedron Letters, 26 (5):647-650 (1985).
Needleman et al. "A general method applicable to the search for similarities in the amino acid sequences of two proteins" (1970) J. Mol. Biol. 48:444-453.
Nektar—Transforming Therapeutics, Nektar Advanced PEGylation: Polyethylene Glycol and Derivatives for Advanced PEGylation, pp. 1-24, catalogue 2004.
Nektar—Transforming Therapeutics, Nektar Molecule Engineering: Polyethylene Glycol and Derivatives for Advanced PEGylation, pp. 1-20, catalogue—2003.
Neuhaus et al., "Effect of Aprotinin on Intraoperative Bleeding and Fibrinolysis in Liver Transplantation," Lancet, 2: 924-925 (1989).
Ngo et al., "The protein folding problem and tertiary structure prediction, Chapter 14: Computational complexity protein structure prediction, and the Levinthal paradox," pp. 433-440 and 492-495 only (1994).
Ning et al., "Production of recombinant humanized anti-HBsAg Fab fragment from Pichia pastoris by fermentation.", J Biochem Mol Biol. ;38(3):294-9. (May 31, 2005).
Nof Corporation, "PEG Derivatives, Phospholipid and Drug Delivery Materials for Pharmaceutical Products and Formulations," pp. 1-59, catalogue Ver. 8—Apr. 2006.
Nof Corporation, "PEG Derivatives, Phospholipid and Drug Delivery Materials for Pharmaceuticals," pp. 1-46, catalogue—2003, 1st.
Nof Corporation, "PEG Derivatives, Phospholipid and Drug Delivery Materials for Pharmaceuticals," pp. 1-50, catalogue—2003 2nd.
Novotney et al., "Purification and Characterization of the Lipoprotein-associated Coagulation Inhibitor from Human Plasma," J. Biol. Chem. 264:18832-18837 (1989).
Nwariaku et al., "Effect of a bradykinin antagonist on the local inflammatory response following thermal injury" Burns, 22:324-327 (1996). (Abstract only).
Oi et al. "Chimeric Antibodies" (1986) BioTechniques 4:214.

(56) References Cited

OTHER PUBLICATIONS

Okamoto et al., "A Finding of Highly Selective Synthetic Inhibitor of Plasma Kallikrein; Its Action to Bradykinin Generation, Intrinsic Coagulation and Experimental DIC," Agents Actions Suppl., 38(I):198-205 (1992).
Okano et al., Chapter 9.1.2 Drug Action and Blood Concentration. Shin Yakuzaiaku Soron, revised 3rd Edition, Apr. 10, 1987:250-253.
O'Reilly et al., "Angiostatin: A Novel Angiogenesis Inhibitor That Mediates the Suppression of Metastases by a Lewis Lung Carcinoma," Cell, 79 317-328 (1994).
Padlan et al., Structure of an antibody-antigen complex: crystal structure of the HyHEL-10 Fab-lysozyme complex. Proc Natl Acad Sci U S A. Aug. 1989;86(15):5938-42.
Palm et al., The Importance of the Concentration-Temperature-Viscosity Relationship for the Development of Biologics. BioProcess International. Mar. 10, 2015. https://bioprocessintl.com/manufacturing/monoclonal-antibodies/importance-concentration-temperature-viscosity-relationship-development-biologics/ [last accessed Mar. 2, 2022]. 7 pages.
Pan et al., "Reperfusion injury following cerebral ischemia: pathophysiology, MR imaging, and potential therapies," Neuroradiology, 2007, vol. 49, pp. 93-102.
Park et al., "Three Dimensional Structure of the Kringle Sequence: Structure of Prothrombin Fragment 1," Biochemistry, 25:3977-3982 (1986).
Paul. Fv Structure and Diversity in Three Dimensions. Fundamental Immunology, 3rd Edition. 1993: 292-5.
Peng, "Experimental use of murine lupus models" Methods Mol Med. 102:227-72 (2004).
Petersen et al., "Inhibitory properties of separate recombinant Kunitz-type-protease-inhibitor domains from tissue-factor-pathway inhibitor," Eur. J. Biochem., 1996, vol. 235, pp. 310-316.
Phillips, "The challenge of gene therapy and DNA delivery," J. Pharm. Pharmacology, vol. 53, pp. 1169-1174 (2001).
Phipps et al., Plasma kallikrein mediates angiotensin II type 1 receptor-stimulated retinal vascular permeability. Hypertension. Feb. 2009;53(2):175-81. doi:10.1161/HYPERTENSIONAHA.108.117663. Epub Jan. 5, 2009.
Pintigny et al., "Aprotinin can inhibit the proteolytic activity of thrombin: a fluorescence and an enzymatic study," Eur. J. Biochem., 1992, vol. 207, pp. 89-95.
Piro et al., "Role for the Kunitz-3 domain of tissue factor pathway inhibitor-a in cell surface binding," Circulation, 2004, vol. 110, pp. 3567-3572.
Pirollo et al., "Targeted delivery of small interfering RNA: approaching effective cancer therapies," Cancer Res., 2008, vol. 68, No. 5, pp. 1247-1250.
Pitt et al., Rabbit monoarticular arthritis as a model for intra-articular drug injections. The local action of administered cortisol and alpha-1 proteinase inhibitor. Agents Actions. Dec. 1984;15(5-6):541-8.
Polypure, Products; PEG amines; PEG acids and amino acids, PEG thils and disulfides; Biotins, Apr. 2005.
Polypure, Products; PEG amines; PEG acids and amino acids; PEG thiols and disulfides; Biotins, Apr. 2004.
Powers et al., "Expression of Single-Chain Fv-Fc Fusions in *Pichia pastoris*", J. Immunol. Methods. 251:123-35 (2001).
Poznansky et al., "Growth hormone-albumin-conjugates reduced renal toxicity and altered plasma clearance," 1988, vol. 239, pp. 18-22.
Putterman, "Aprotinin Therapy in Septic Shock," ACTA Chir. Scand., 155:367 (1989).
Quanta Biodesign, Labeling, Derivatization and Crosslinking Reagents for Biological and Related Materials with dPEGTM, pp. 1-38, Mar. 12, 2004.
Quanta Biodesign, Labeling, Modification and Crosslinking Reagents incorporating our unique monodispersed dPEGTM, pp. 1-31, Nov. 5, 2004.
Quanta Biodesign, Leading innovator, producer and provider of monodisperse discrete PEGTM (dPEGTM) derivatives, Product Catalogue, pp. 1-51, Updated: Nov. 17, 2005.
Rahman et al., "Identification and functional importance of plasma kallikrein in the synovial fluids of patients with rheumatoid, psoriatic, and osteoarthritis," Annals of the Rheumatic Diseases, vol. 54, pp. 345-350 (1995).
Raspi, Kallikrein and kallikrein-like proteinases: purification and determination by chromatographic and electrophoretic methods. J Chromatogr B Biomed Appl. Sep. 20, 1996;684(1-2):265-87.
Reginato et al., "Genetics and experimental models of crystal-induced arthritis. Lessons learned from mice and men: is it crystal clear?" Curr Opin Rheumatol. 19(2):134-45 (2007).
Reichert, "Technology evaluation: lumiliximab, Biogen Idec" Curr Opin Mol Ther., 6(6):675-83 (2004). (Abstract only).
Ren et al., "Inflammatory Models of Pain and Hyperalgesia" Ilar J. 40(3): 111-118 (1999).
Riedl et al., 322: Attack-Free Status of Patients With Hereditary Angioedema (HAE) During Extended Treatment With Lanadelumab in the Help Ole Study. Journal of Allergy and Clinical Immunology. Feb. 1, 2020;145(2):AB104.
Riedl et al., An open-label study to evaluate the long-term safety and efficacy of lanadelumab for prevention of attacks in hereditary angioedema: design of the HELP study extension. Clin Transl Allergy. Oct. 6, 2017;7: 36. doi: 10.1186/s13601-017-0172-9.
Riedl et al., Lanadelumab demonstrates rapid and sustained prevention of hereditary angioedema attacks. Allergy. Nov. 2020;75(11):2879-2887. doi: 10.1111/all.14416. Epub Jul. 6, 2020.
Robbins et al., Hemostasis and Thrombosis, Chapter 21, 2nd Edition, Basic Principles and Clinical Practice: 340-357 (1987).
Roberts et al., "Chemistry for peptide and protein PEGylation", Advanced Drug Delivery Reviews, 54, pp. 459-476, 2002.
Roberts et al., "Directed evolution of a protein: selection of potent neutrophil elastase inhibitor displayed on M13 fusion phage," PNAS USA, vol. 89, pp. 2429-2433 (1992).
Roberts et al., "Protease inhibitor display M13 phage: selection of high-affinity neutrophil elastase inhibitors," Gene, vol. 121, pp. 9-15 (1992).
Rossi et al., The Synthetic Peptide DX88 Binds to Endothelial Cells In Vitro and Retains the Inhibitory Activity on Kallikrein, International Immunopharmacology 2(9):1313, Abstract 142 (2002).
Rudikoff et al., Single amino acid substitution altering antigen-binding specificity. Proc Natl Acad Sci U S A. Mar. 1982;79(6):1979-83.
Ruggieri et al., Successful private-public funding of paediatric medicines research: lessons from the EU programme to fund research into off-patent medicines. Eur J Pediatr. Apr. 2015;174(4):481-91. doi: 10.1007/s00431-014-2398-z. Epub Sep. 23, 2014.
Sainz et al., "Fifty years of research on the plasma kallikrein-kinin system: from protein structure and function to cell biology and in-vivo pathophysiology" Thromb Haemost 98, 77-83, 2007.
Sartor et al., "Selective Kallikrein-Kinin System Activation in Inbred Rats Differentially Susceptible to Granulomatous Enterocolitis," Gastroenterology, 110:1467-1481 (1996).
Scarff et al., "Targeted disruption of SP13/Serpinb6 does not result in development of growth defects, leukocyte dysfunction, or susceptibility to stroke," Molecular and Cellular Biology, May 2004, pp. 4075-4082.
Scatchard, The Attractions of Proteins for Small Molecules and Ions, Ann. NY Acad. Sci, 51:660-672 (1949).
Schaffirzel et al., "Ribosome display: an in vitro method for selection and evolution of antibodies from libraries" J Immunol Methods. 231(1-2):119-35 (1999).
Schechter et al., On the Active Site of Proteases, III Mapping the Active Site of Papain; Specific Peptide Inhibitors of Papain, Biochemical and Biophysical Research Communications 32(5):898-902 (1968).
Schechter et al., On the Size of the Active Site on Proteases, I Papain, Biochemical and Biophysical Research Communications 27(2):157-162 (1967).
Schmaier et al., Hemostasis and Thrombosis, Chapter 2, 2nd Edition, Basic Principals and Clinical Practice: 18-38 (1987).

(56) References Cited

OTHER PUBLICATIONS

Schmaier, "Assembly, activation, and physiologic influence of the plasma kallikrein/kinin system" (2008) Int Immunopharmaco18, 161-165. Author manuscript.
Schmid-Elsaesser et al., "A critical reevaluation of the intraluminal thread model of focal cerebral ischemia: evidence of inadvertent premature reperfusion and subarachnoid hemorrhage in rats by laser-Doppler flowmetry" Stroke 29 (10): 2162-70(1989).
Schmidt et al., "A male accessory gland peptide with protease inhibitory activity in *Drosophila funebris*," J Biol Chem. Jun. 15, 1989;264(17):9745-9.
Schnabel et al., Aprotinin: Preparation by Partial Desulphurization of Aprotinin by Means of Raney Nickel and Comparison with Other Aprotinin Derivatives, Biol. Chem. Hoppe-Seyler, 367:1167-1176 (1986).
Schneider et al., Critical role of kallikrein in hereditary angioedema pathogenesis: a clinical trial of ecallantide, a novel kallikrein inhibitor. J Allergy Clin Immunol. Aug. 2007;120(2):416-22. Epub Jun. 7, 2007.
Schofield et al., "Monoclonal antibodies that neutralize HEV recognize an antigenic site at the carboxyterminus of an ORF2 protein vaccine" Vaccine (2003) 22(2):257-67.
Schoonbroodt et al., Human antibodies selected by phage display as potent and selective protease inhibitors. Human Antibodies. 2007;16(1-2):18-22.
Schoonooghe et al., "Efficient production of human bivalent and trivalent anti-MUC1 Fab-scFv antibodies in Pichia pastoris", BMC Biotechnol. Aug. 11, 2009;9:70.
Schopf, "IDEC-114 (IDEC)" Curr Opin Investig Drugs, 2(5):635-8 (2001). (Abstract only).
Schultz et al. "SMART, a simple modular architecture research tool: identification of signaling domains" (1998) Proc. Natl. Acad. Sci. USA 95:5857-5864.
Schultz et al., "SMART: a web-based tool for the study of genetically mobile domains" (2000) Nucl. Acids Res 28:231-234.
Schwartz et al., "Stability studies on derivatives of the bovine trypsin inhibitor," Biochemistry, vol. 26, pp. 3544-3551 (1987).
Sekiguchi et al., "Experimental spinal stenosis: relationship between degree of cauda equina compression, neuropathology, and pain" Spine 29, 1105-1111 (2004)).
Sela-Culang et al., The structural basis of antibody-antigen recognition. Front Immunol. Oct. 8, 2013;4:302. doi: 10.3389/fimmu.2013.00302.
Sexton et al., Comparison of Plasma Kallikrein Inhibition by The Endogenous C1-Inhibitor Versus DX-2930, a Monoclonal Antibody Inhibitor. Blood. 2013; 122: 1066. Abstract only.
Sexton et al., Discovery and characterization of fully human monoclonal antibody inhibitor of plasma kallikrein for the treatment of plasma kallikrein-mediated edema. J Allergy Clin Immunol. Feb. 2013;131(2): AB32. Suppl S. Annual meeting of the American Academy of Allergy, Asthma, and Immunology. San Antonio, TX, USA; Feb. 22-26.
Sexton et al., Specific inhibition of tissue kallikrein 1 with a human monoclonal antibody reveals a potential role in airway diseases. Biochem J. Aug. 13, 2009;422(2):383-92. doi: 10.1042/BJ20090010.
Shariat-Madar et al., Assembly and activation of the plasma kallikrein/kinin system: a new interpretation. Int Immunopharmacol. Dec. 2002;2(13-14):1841-9.
Sharma et al., "The kinin antagonist hoe 140 reduces acute paw oedema in rats caused by carrageenan, bradykinin and kaolin" Inflammopharmacology 6,9-17 (1998).
Shearwater Corporation, Polyethylene Glycol and Derivatives for Biomedical Applications, pp. 1-17, catalogue—2001.
Shearwater Polymers, Inc., Polyethylene Glycol and Derivatives, pp. 1-50, catalogue—Jul. 1997.
Shearwater Polymers, Inc., Polyethylene Glycol Derivatives: Functionalized Biocompatible Polymers for Research and Pharmaceuticals, pp. 1-50, catalogue—2000.
Shearwater Polymers, Inc., pp. 2-49, catalogue—Mar. 1995.
Sheppard et al., Acid-Labile Resin Linkage Agents for Use in Solid Phase Peptide Synthesis, Int. J. Peptide Protein Res., 20:451-454 (1982).
Sheridan et al., A Multicenter Trial of the Use of the Proteolytic Enzyme Inhibitor Aprotinin in Colorectal Surgery, Dis. Colon Rectum, 32:505-508 (1989).
Shibuya et al., "Primary Structure of Guinea Pig Plasma Prekallikrein", Immunopharmacology, vol. 45 (1-3), p. 127-134, Abstract p. 131, Fig 1, 2 (1999).
Siebeck et al., "Inhibition of plasma kallikrein with aprotinin in porcine endotoxin shock," J. Trauma, vol. 34, pp. 193-198 (1993).
Silverberg et al. "The Contact System and Its Disorders," in Blood: Principles and Practice of Hematology, Handin R. et al., eds. J B. Lippincott Co., Philadelphia, (1995).
Singer et al., "A porcine burn model" Methods Mol Med. 78: 107-19 (2003).
Skolnick et al., "From genes to protein structure and function: novel applications of computational approaches in the genomic era," Trends in Biotech., 2000, vol. 18, No. 1, pp. 34-39.
Slootstra et al., "Structural aspects of antibody-antigen interaction revealed through small random peptide libraries", Molecular Diversity,1, 87-96 (1996).
Smith et al. "Prolonged in vivo residence times of antibody fragments associated with albumin" Bioconjug Chem 12(5):750-756 (2001).
Smith, "Filamentous fusion phage: novel expression vectors that display cloned antigens on the virion surface" Science 228:1315-1317 (1985).
Sonhammer et al., "Pfam: a comprehensive database of protein domain families based on seed alignments" (1997) Proteins 28(3):405-420.
Sonis et al., "An animal model for mucositis induced by cancer chemotherapy" (1990) Oral Surg Oral Med Oral Pathol. 69:437-43.
Sonis et al., "Validation of a new scoring system for the assessment of clinical trial research of oral mucositis induced by radiation or chemotherapy. Mucositis Study Group." (1999) Cancer 85:2103-13.
Sprecher et al., "Molecular Cloning, Expression, and Partial Characterization of a Second Human Tissue-Factor-Pathway Inhibitor," Proc. Natl. Acad. Sci. USA, 91:3353-3357 (1994).
Stadnicki et al., "Activation of plasma contact and coagulation systems and neutrophils in the active phase of ulcerative colitis," Digestive Diseases and Sciences, 1997, vol. 42, No. 1, pp. 2356-2366.
Stadnicki et al., "Activation of the contact system and circulating neutrophil elastase in ulcerative colitis patients" 10th World Congress of Gastroenterology, p. 1166, 1994.
Stadnicki et al., "Activation of the Kallikrein-Kinin System in Indomethacin-Induced Entercolitis in Genetically Susceptible Rats," J. Invest. Med., 44:299A (1996).
Stadnicki et al., "Selective Plasma Kallikrein Inhibitor Attenuates Acute Intestinal Inflammation in Lewis Rat," Dig. Dis. Sci., 41:912-920 (1996).
Stevenson et al., "A mouse model of burn wounding and sepsis" Methods Mol Med. 78:95-105 (2003).
Stewart et al., Solid-Phase Peptide Synthesis (W.H. Freeman Co., San Francisco 1989). 6 pages.
Stultz et al., "Structural analysis based on state-space modeling." Protein Sci. 2:305-314 (1993).
Sunkureddi et al., "Clinical signs of gout," Hospital Physician, 2006, pp. 39-41. Retrieved from the internet <http://citeseerx.ist.psu.edu/viewdoc/download?doi=10.1.1.643.7808&rep=rep1&type=pdf> on Aug. 1, 2018.
Taby et al., "Inhibition of activated protein C by aprotinin and the uses of the insolubilized inhibitor for its purification," Thrombosis Research, 1990, vol. 59, pp. 27-35.
Tachdjian et al., Lanadelumab efficacy after switching from placebo: results from the HELP and HELP open-label extension studies. Ann Allergy Asthma Immunol. Nov. 2018;121(5):S38.
Taggart et al., "Inactivation of human-b-defensins 2 and 3 by elastolytic cathepsins1," The Journal of Immunology, 2003, vol. 170, pp. 931-937.

(56) References Cited

OTHER PUBLICATIONS

Takahashi et al., "Production of humanized Fab fragment against human high affinity IgE receptor in Pichia pastoris" Biosci Biotechnol Biochem 64(10):2138-44 (2000).
Tamura et al., "Focal cerebral ischaemia in the rat: 1. Description of technique and early neuropathological consequences following middle cerebral artery occlusion" J Cereb Blood Flow Metab 1: 53-60 (1981).
Tanaka et al. "A novel rat model of abdominal aortic aneurysm using a combination of intraluminal elastase infusion and extraluminal calcium chloride exposure" J Vasc Surg. 50(6):1423-32 (2009).
Tang et al., Expression, crystallization, and three-dimensional structure of the catalytic domain of human plasma kallikrein. J Biol Chem. Dec. 9, 2005;280(49):41077-89. Epub Sep. 30, 2005.
The Merck Index, 11th edition, 1989. pp. 145, 146, 263, 427, 428, 1183, and 1184. 9 pages.
Tian et al., Synthesis of optically pure C alpha-methyl-arginine. Int J Pept Protein Res. Aug. 1992;40(2):119-26.
Timmerman et al., "Functional reconstruction and synthetic mimicry of a conformational epitope using CLIPS TM technology" J. Mol. Recognit. 20:283-99 (2007).
Tinning et al., Make your Best Guess: an updated method for paediatric weight estimation in emergencies. Emerg Med Australas. Dec. 2007;19(6):528-34. doi: 10.1111/j.1742-6723.2007.01026.x.
Tomlinson et al. "Structural repertoire of the human Vk domain" EMBO J. 14(18):4628-3 (1995).
Tomlinson et al. "The repertoire of human germline VH sequences reveals about 50 groups of VH segments with different hypervariable loops" J. Mol. Biol. 227:776-798 (1992).
Travis et al., "Pulmonary perspective: potential problems in designing elastase inhibitors for therapy," Am. Rev. Respir. Dig., 1991, vol. 143, pp. 1412-1415.
Tremblay et al., "Anti-inflammatory activity of neutrophil elastase inhibitors," Current Opinion in Investigational Drugs, 2003, vol. 4, No. 5, pp. 556-565.
Tschesche et al., "Semisynthetic engineering of proteinase inhibitor homologues," Biochim. Biophys. Acta, vol. 913, pp. 97-101 (1987).
Uebel, Die Behandlung von Kniegelenksarthrosen mit Trasylol [The treatment of arthroses of the knee joint with Trasylol]. Langenbacks Arch. Chir., vol. 325, pp. 356-358 (1969).
Urlaub et al., "Isolation of Chinese hamster cell mutants deficient in dihydrofolate reductase activity", Proc. Natl. Acad. Sci. USA 77:4216-4220 (1980).
Vajdos et al., Comprehensive functional maps of the antigen-binding site of an anti-ErbB2 antibody obtained with shotgun scanning mutagenesis. J Mol Biol. Jul. 5, 2002;320(2):415-28.
Van Der Logt et al., "Intron-Exon Organization of the Human Gene Coding for the Lipoprotein-associated Coagulation Inhibitor: The Factor Xa Dependent of Inhibitor of the Extrinsic Pathway of Coagulation," Biochemistry, 30:1571-1577 (1991).
Van Dijl et al., "Signal Peptidase 1 of Bacillus subtilis: Patterns of Conserved Amino Acids in Prokaryotic and Eukaryotic Type 1 Signal Peptidases," The EMBO Journal, 11:2819-2828 (1992).
Varadi et al., "Location of Plasminogen-Binding Sites in Human Fibrin(ogen)," Biochemistry, 22:2440-2446 (1983).
Varadi et al., Segment of Fibrinogen Is in a Region Essential for Plasminogen Binding by Fibrin Fragment E, Biochemistry, 23:2108-2112 (1984).
Vedvick et al., "High-Level Secretion of Biologically Active Aprotinin from the Yeast *Pichia pastoris*," J. Ind. Microbiol., 7:197-201 (1991).
Veloso et al., A monoclonal anti-human plasma prekallikrein antibody that inhibits activation of prekallikrein by factor XIIa on a surface. Blood. Oct. 1987;70(4):1053-62.
Veronese, "Peptide and protein PEGylation: a review of problems and solutions," Biomaterials, Mar. 1, 2001, vol. 22, No. 5, pp. 405-417.
Veronez et al., The involvement of proteoglycans in the human plasma prekallikrein interaction with the cell surface. PLoS One. Mar. 12, 2014;9(3):e91280. doi: 10.1371/journal.pone.0091280. eCollection 2014.
Vidal et al., "Making sense of antisense," European Journal of Cancer, 2005, vol. 41, pp. 2812-2818.
Viswanathan et al., "Engineered protein protease inhibitors", Current Enzyme Inhibition, Jan. 1, 2009, pp. 87-98, vol. 5, No. 2, Betham Science Publishers Ltd., Hilversum, NL.
Volpe-Junior et al., "Augmented plasma and tissue kallikrein like activity in synovial fluid of patients with inflammatory articular diseases," Inflamm. Res., 1996, vol. 45, pp. 198-202.
Wade et al., Solid-phase synthesis of alpha-human atrial natriuretic factor: comparison of the Boc-polystyrene and Fmoc-polyamide methods. Biopolymers. 1986;25 Suppl:S21-37.
Wagner et al., High level expression, purification, and characterization of the Kunitz-type protease inhibitor domain of protease nexin-2/amyloid beta-protein precursor. Biochem Biophys Res Commun. Jul. 31, 1992;186(2):1138-45.
Walpole et al., The weight of nations: an estimation of adult human biomass. BMC Public Health. Jun. 18, 2012;12:439. doi: 10.1186/1471-2458-12-439.
Wang et al., "Monitoring of heparin-induced anticoagulation with kaolin-activated clotting time in cardiac surgical patients treated with aprotinin," Anesthesiology, vol. 77, pp. 1080-1084 (1992).
Wang et al., Antibody structure, instability, and formulation. J Pharm Sci. Jan. 2007;96(1):1-26. doi: 10.1002/jps.20727.
Ward et al. "Binding activities of a repertoire of single immunoglobulin variable domains secreted from *Escherichia coli*" (1989) Nature 341:544-546.
Wark et al., Latest technologies for the enhancement of antibody affinity. Adv Drug Deliv Rev. Aug. 7, 2006;58(5-6):657-70. Epub May 22, 2006.
Wark, "DX-890 (Dyax)", iDrugs, 5, pp. 586-589, Jun. 2002.
Watson et al., "Induction of reproducible brain infarction by photochemically initiated thrombosis" Ann Neurol17: 497-504 (1985).
Weaver, Animal studies paint misleading picture. Nature International Weekly Journal of Science. Published online Mar. 30, 2010. Retrieved on Aug. 1, 2017 from http://www.nature.com/news.2010.158.html.
Wedi, Lanadelumab to treat hereditary angioedema. Drugs Today (Barc). Jul. 2019;55(7):439-448. doi: 10.1358/dot.2019.55.7.2985293.
Wedner et al., Modeling and Analyses to Identify Potential Dosing Regimens of DX-2930 for the Long-Term Prophylaxis of Hereditary Angioedema. J All Clin Immunol. Feb. 1, 2016;137(2):AB252.
Wei et al., "Production and characterization of ectoine by *Marinococcus* sp. ECT1 isolated from a high-salinity environment." J Biosci Bioeng. Mar. 2011;111(3):336-42. Epub Dec. 15, 2010.
Wellington et al., "Tranexamic Acid: A review of its use in the management of menorrhagia", Drugs, vol. 63, No. 13, pp. 1417-1433, 2003.
Wells, "Additivity of Mutational Effects in Proteins", Biochemistry, vol. 29 (37), pp. 8509-8517 (1990).
Wendel et al., Lower Cardiac Troponin T Levels in Patients Undergoing Cardiopulmonary Bypass and Receiving High-Dose Aprotinin Therapy Indicate Reduction of Perioperative Myocardial Damage; Journal of Thoracic Cardiovascular Surgery, vol. 109, No. 6, pp. 1164-1172 (1995).
Williams et al. "Collagen-induced arthritis as a model for rheumatoid arthritis" Methods Mol Med. 98:207-16 (2004).
Wilson et al., "An animal model of chronic inflammatory pain: pharmacological and temporal differentiation from acute models" Eur J Pain. 10(6):537-49 (2006).
Wilson et al., "The Calculation and Synthesis of a Template Molecule," Tetrahedron, 49:3655-3663 (1993).
Wood, "Hemostatic Drugs" New England Journal of Medicine, Drug Therapy, 339(4):245-253 (1998).
Worthy et al., Kallikreins and kinins: mediators in inflammatory joint disease? Int J Exp Pathol. Aug. 1990;71(4):587-601.
Wu et al., Humanization of a murine monoclonal antibody by simultaneous optimization of framework and CDR residues. J Mol Biol. Nov. 19, 1999;294(1):151-62.

(56) References Cited

OTHER PUBLICATIONS

Wu, Lanadelumab for the treatment of hereditary angioedema. Expert Opin Biol Ther. Dec. 2019;19(12):1233-1245. doi: 10.1080/14712598.2019.1685490. Epub Nov. 4, 2019.
Wun et al., “Cloning and Characterization of a cDNA Coding for the Lipoprotein-associated Coagulation Inhibitor Shows that it Consists of Three Tandem Kunitz-type Inhibitory Domains,” J. Biol. Chem. 263:6001-6004 (1988).
Yao et al., Progress in the Research of Prophylaxis and Treatment for Hereditary Angioedema. J Diagn Ther Dermato-Venereol. Feb. 28, 2018;25(1):53-6.
Yetkin et al., “The healing effect of TGF-[alpha] on gastric ulcer induced by acetylsalicylic acid in rats”, International Journal of Pharmaceutics, vol. 277, No. 1-2, Jun. 1, 2004, pp. 163-172.
Zuraw et al., “Clinical practice. Hereditary angioedema” N Engl J Med. 2008;359:1027-36.
Zuraw et al., Lanadelumab Exposure During Steady State: Achievement of Effective Concentrations in Patients in the Help Study. Annals of Allergy, Asthma & Immunology. Nov. 1, 2018;121(5):S37-8.
Zuraw et al., Lanadelumab Exposure During Steady State: Achievement of Effective Concentrations in Patients in the HELP Study. Poster. American College of Asthma, Allergy & Immunology. Annual Scientific Meeting. Seattle, WA. Nov. 2018.
Zuraw, HAE therapies: past present and future. Allergy Asthma Clin Immunol. Jul. 28, 2010;6(1):23. doi: 10.1186/1710-1492-6-23.
[No Author Listed], ClinicalTrials. gov Identifier: NCT02093923. A Double-Blind, Multiple Ascending Dose Study to Assess Safety, Tolerability and Pharmacokinetics of DX-2930 in Hereditary Angioedema Participants. Oct. 16, 2014. https://clinicaltrials.gov/ct2/show/NCT02093923 [last accessed Sep. 10, 2025]. 5 pages.
Bernstein et al., Sustained Effectiveness, Tolerability, and Safety of Long-Term Prophylaxis with Lanadelumab in Hereditary Angioedema: The Prospective, Phase 4, Noninterventional Empower Real-World Study. Adv Ther. Aug. 2025;42(8):3882-3901. doi: 10.1007/s12325-025-03226-3. Epub Jun. 12, 2025.
Khayat et al., Animal Models of Retinal Vein Occlusion. Invest Ophthalmol Vis Sci. Dec. 1, 2017;58(14):6175-6192. doi: 10.1167/iovs.17-22788.
Lambert et al., Laser-induced choroidal neovascularization model to study age-related macular degeneration in mice. Nat Protoc. Nov. 2013;8(11):2197-211. doi: 10.1038/nprot.2013.135. Epub Oct. 17, 2013.
Luyt et al., Virus-induced acute respiratory distress syndrome: Epidemiology, management and outcome. Presse Med. Dec. 2011;40(12 Pt 2):e561-8. doi: 10.1016/j.lpm.2011.05.027. Epub Nov. 16, 2011.
Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.
Reyns et al., Selection Strategy of In Vivo Models for Ophthalmic Drug Development in Diabetic Retinopathy. J Mol Genet Med. 2016;10(1):1000202. doi: 10.4172/1747-0862.1000202. 18 pages.
Shah et al., A Mouse Model for Laser-induced Choroidal Neovascularization. J Vis Exp. Dec. 27, 2015;(106):e53502. doi: 10.3791/53502.
Sun et al., Why 90% of clinical drug development fails and how to improve it? Acta Pharm Sin B. Jul. 2022;12(7):3049-3062. doi: 10.1016/j.apsb.2022.02.002. Epub Feb. 11, 2022.

* cited by examiner

KITS

RELATED APPLICATIONS

This application is a continuation of U.S. application Ser. No. 16/817,671, filed Mar. 13, 2020, which claims the benefit under 35 U.S.C. § 119(e) of U.S. Provisional Application No. 62/818,189, filed Mar. 14, 2019. The entire contents of each of these referenced applications are incorporated by reference herein.

REFERENCE TO AN ELECTRONIC SEQUENCE LISTING

The contents of the electronic sequence listing (D061770132US02-SEQ-EMB.xml; Size: 13,936 bytes; and Date of Creation: May 2, 2025) is herein incorporated by reference in its entirety.

BACKGROUND

Plasma kallikrein is a serine protease component of the contact system and a potential drug target for different inflammatory, cardiovascular, infectious (sepsis) and oncology diseases (Sainz I. M. et al., *Thromb Haemost* 98, 77-83, 2007). The contact system is activated by either factor XIIa upon exposure to foreign or negatively charged surfaces or on endothelial cell surfaces by prolylcarboxypeptidases (Sainz I. M. et al., *Thromb Haemost* 98, 77-83, 2007). Activation of the plasma kallikrein amplifies intrinsic coagulation via its feedback activation of factor XII and enhances inflammation via the production of the proinflammatory nonapeptide bradykinin. As the primary kininogenase in the circulation, plasma kallikrein is largely responsible for the generation of bradykinin in the vasculature. A genetic deficiency in the C1-inhibitor protein (C1-INH), the major natural inhibitor of plasma kallikrein, leads to hereditary angioedema (HAE). Patients with HAE suffer from acute attacks of painful edema often precipitated by unknown triggers (Zuraw B. L. et al., *N Engl J Med* 359, 1027-1036, 2008).

SUMMARY

Provided herein are regimens for treating hereditary angioedema (HAE) attack, reducing the rate of HAE attack, or blocking HAE attack using antibodies capable of binding and inhibiting human plasma kallikrein (pKal) in the active form, for example, antibodies having the same complementarity determining regions (CDRs) as DX-2930 (a.k.a. SHP643, lanadelumab).

In aspect, the present disclosure provides a method for treating hereditary angioedema (HAE) attack or reducing the rate of HAE attack, the method comprising: (i) administering (e.g., subcutaneously) to a subject in need thereof an antibody that binds human plasma kallikrein at about 300 mg every about two weeks in a first treatment period, which is about 4-9 months (e.g., 6 months); (ii) monitoring the subject for HAE attack during the first treatment period; and (iii) reducing the dosage of the antibody to about 300 mg every about 4 weeks in the subject, who is free of HAE attack in the first treatment period.

In some instances, the antibody used in the method described herein comprises the same heavy chain complementarity-determining regions (CDRs) and the same light chain CDRs as DX-2930. For example, the antibody may comprise a heavy chain immunoglobulin variable domain ($V_H$) of SEQ ID NO: 3 and a light chain immunoglobulin variable domain ($V_L$) of SEQ ID NO: 4. Such an antibody may be a full-length antibody (e.g., an IgG1 molecule). Alternatively, the antibody may be an antigen-binding fragment thereof. In one example, the antibody may comprise a heavy chain of SEQ ID NO:1 and a light chain of SEQ ID NO: 2.

Any of the antibodies described herein may be formulated in a pharmaceutical composition comprising a pharmaceutically acceptable carrier. In some embodiments, the pharmaceutical composition may comprise sodium phosphate, citric acid, histidine, sodium chloride, and polysorbate 80. In some examples, the pharmaceutical composition comprises sodium phosphate at a concentration of about 30 mM, citric acid at a concentration of about 19 mM, histidine at a concentration of about 50 mM, sodium chloride is at a concentration of about 90 mM, and polysorbate 80 at about 0.01%.

The subject to be treated in any of the methods described herein may be a human patient having a low body weight, for example, less than 35 kg. In some instances, the human patient is a pediatric patient. The subject may be a human patient having, suspected of having, or at risk for HAE (e.g., Type I or Type II).

The details of one or more embodiments of the invention are set forth in the description below. Other features or advantages of the present invention will be apparent from the following drawing and detailed description of several embodiments, and also from the appended claims.

DETAILED DESCRIPTION

Definitions

Figure 1:
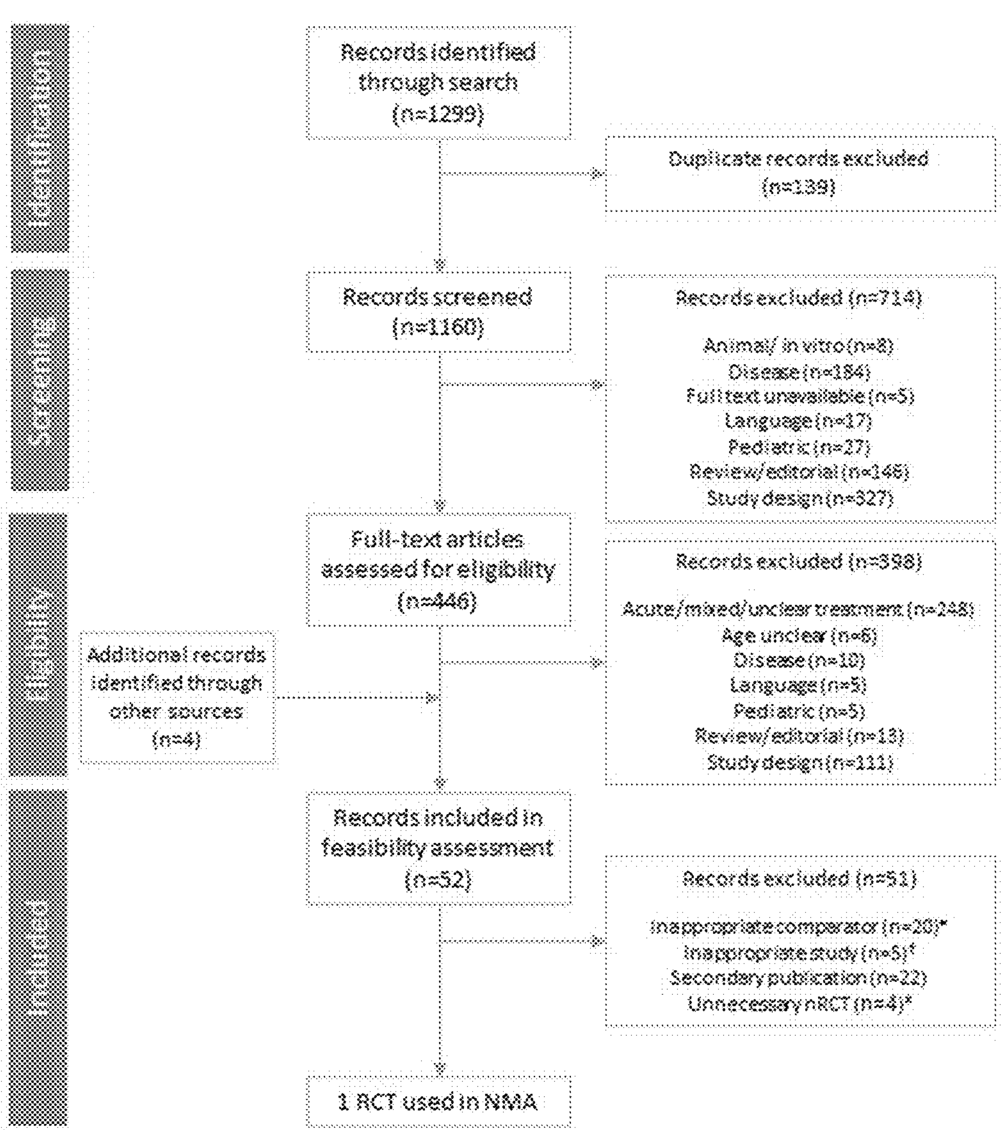
FIG. 1 is a Preferred Reporting Items for Systematic Reviews and Meta-Analyses (PRISMA) diagram documenting the systemic literature review used to identify studies for an indirect treatment comparison. An asterisk (*) indicates studies describing use of interventions that lacked real-world applicability, which were excluded as inappropriate comparators and included attenuated androgens (danazol, stanozolol, methyltestosterone, fluoxymesterone, oxymetholone, and tibolone; n=17), combination therapy of SC C1-INH/recombinant human hyaluronidase (n=1), and SC C1-INH (n=2). A dagger (†) indicates inappropriate studies excluded because of differences and/or lack of clarity in study design, study population, intervention, endpoints, and/or patient characteristics, as summarized in Table 2. A double-dagger (‡) indicates the exclusion of four unnecessary non-randomized control trials, as one randomized control trial for IV C1-INH (Cinryze®) was identified as appropriate for NMA. The four nRCTs for this same intervention were excluded. C1-INH, C1 esterase inhibitor; IV, intravenous; NMA, network meta-analysis; nRCT, non-randomized controlled trial; PRISMA, Preferred Reporting Items for Systematic Reviews and Meta-Analyses; RCT, randomized controlled trial; SC, subcutaneous.

For convenience, before further description of the present invention, certain terms employed in the specification, examples and appended claims are defined here. Other terms are defined as they appear in the specification.

The singular forms "a", "an", and "the" include plural references unless the context clearly dictates otherwise.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The term "antibody" refers to an immunoglobulin molecule capable of specific binding to a target, such as a carbohydrate, polynucleotide, lipid, polypeptide, etc., through at least one antigen recognition site located in the variable region of the immunoglobulin molecule. An antibody may include at least one heavy (H) chain that comprises a heavy chain immunoglobulin variable domain ($V_H$), at least one light chain that comprises a light chain immunoglobulin variable domain ($V_L$), or both. For example, an antibody can include a heavy (H) chain variable region (abbreviated herein as $V_H$ or HV) and a light (L) chain variable region (abbreviated herein as $V_L$ or LV). In another example, an antibody includes two heavy (H) chain variable regions and two light (L) chain variable regions.

As used herein, the term "antibody" encompasses not only intact (i.e., full-length) polyclonal or monoclonal antibodies, but also antigen-binding fragments thereof (such as Fab, Fab', $F(ab')_2$, Fv), single chain (scFv), domain antibody (dAb) fragments (de Wildt et. al., *Euro. J. Immunol.* (1996) 26 (3): 629-639), any mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgAQ1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. Antibodies may be from any source, but primate (human and non-human primate) and primatized are preferred.

The $V_H$ and/or $V_L$ regions may include all or part of the amino acid sequence of a naturally-occurring variable domain. For example, the sequence may omit one, two or more N-or C-terminal amino acids, internal amino acids, may include one or more insertions or additional terminal amino acids, or may include other alterations. In one embodiment, a polypeptide that includes immunoglobulin variable domain sequence can associate with another immunoglobulin variable domain sequence to form an antigen binding site, e.g., a structure that preferentially interacts with plasma kallikrein.

The $V_H$ and $V_L$ regions can be further subdivided into regions of hypervariability, termed "complementarity determining regions" ("CDRs"), interspersed with regions that are more conserved, termed "framework regions" ("FRs"). The extent of the framework region and CDRs have been defined (see, Kabat, E. A., et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917). Kabat definitions are used herein. Each $V_H$ and $V_L$ is typically composed of three CDRs and four FRs, arranged from amino-terminus to carboxy-terminus in the following order: FR1, CDR1, FR2, CDR2, FR3, CDR3, FR4.

In addition to the $V_H$ or $V_L$ regions, the heavy chain or light chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3. The light chain constant region includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The light chains of the immunoglobulin may be of type kappa or lambda. In one embodiment, the antibody is glycosylated. An antibody can be functional for antibody-dependent cytotoxicity and/or complement-mediated cytotoxicity.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and/or LC CDR3. Each of the light chain (LC) and/or heavy chain (HC) CDRs can be human. HC CDR3 can be human. One or more of the framework regions can be human, e.g., FR1, FR2, FR3, and/or FR4 of the HC and/or LC. For example, the Fc region can be human. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. In one embodiment, the framework (FR) residues of a selected Fab can be converted to the amino-acid type of the corresponding residue in the most similar primate germline gene, especially the human germline gene. One or more of the constant regions can be human or effectively human. For example, at least 70, 75, 80, 85, 90, 92, 95, 98, or 100% of an immunoglobulin variable domain, the constant region, the constant domains (CH1, CH2, CH3, and/or CL1), or the entire antibody can be human or effectively human.

An antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the many immunoglobulin variable region genes. Full-length immunoglobulin "light chains" (about 25 KDa or about 214 amino acids) are encoded by a variable region gene at the NH2-terminus (about 110 amino acids) and a kappa or lambda constant region gene at the COOH-terminus. Full-length immunoglobulin "heavy chains" (about 50 KDa or about 446 amino acids), are similarly encoded by a variable region gene (about 116 amino acids) and one of the other aforementioned constant region genes, e.g., gamma (encoding about 330 amino acids). The length of human HC varies considerably because HC CDR3 varies from about 3 amino-acid residues to over 35 amino-acid residues.

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody and that retain functionality include (i) a Fab fragment, a monovalent fragment consisting of the $V_L$, $V_H$, CL and CH1 domains; (ii) a $F(ab')_2$ fragment, a bivalent fragment including two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., U.S. Pat. Nos. 5,260,203, 4,946,778, and 4,881,175; Bird et al. (1988) *Science* 242:423-426; and Huston et al. (1988) *Proc. Natl. Acad. Sci. USA* 85:5879-5883. Antibody fragments can be obtained using any appropriate technique including conventional techniques known to those with skill in the art.

The term "monospecific antibody" refers to an antibody that displays a single binding specificity and affinity for a particular target, e.g., epitope. This term includes a "monoclonal antibody" or "monoclonal antibody composition," which as used herein refers to a preparation of antibodies or fragments thereof of single molecular composition, irrespective of how the antibody was generated. Antibodies are "germlined" by reverting one or more non-germline amino acids in framework regions to corresponding germline amino acids of the antibody, so long as binding properties are substantially retained.

The inhibition constant ($K_i$) provides a measure of inhibitor potency; it is the concentration of inhibitor required to reduce enzyme activity by half and is not dependent on enzyme or substrate concentrations. The apparent $K_i$ ($K_{i,app}$) is obtained at different substrate concentrations by measuring the inhibitory effect of different concentrations of inhibitor (e.g., inhibitory binding protein) on the extent of the reaction (e.g., enzyme activity); fitting the change in pseudo-first order rate constant as a function of inhibitor concentration to the Morrison equation (Equation 1) yields an estimate of the apparent $K_i$ value. The $K_i$ is obtained from the y-intercept extracted from a linear regression analysis of a plot of $K_{i,app}$ versus substrate concentration.

$$v = v_o - v_o\left(\frac{(K_{i,app} + I + E) - \sqrt{(K_{i,app} + I + E)^2 - 4 \cdot I \cdot E}}{2 \cdot E}\right) \quad \text{Equation 1}$$

Where v=measured velocity; v0=velocity in the absence of inhibitor; $K_{i,app}$=apparent inhibition constant; I=total inhibitor concentration; and E=total enzyme concentration.

As used herein, "binding affinity" refers to the apparent association constant or $K_A$. The $K_A$ is the reciprocal of the dissociation constant ($K_D$). A binding antibody may, for example, have a binding affinity of at least 105, 106, 107, 108, 109, 1010 and 1011 M-1 for a particular target molecule, e.g., plasma kallikrein. Higher affinity binding of a binding antibody to a first target relative to a second target can be indicated by a higher $K_A$ (or a smaller numerical value $K_D$) for binding the first target than the $K_A$ (or numerical value $K_D$) for binding the second target. In such cases, the binding antibody has specificity for the first target (e.g., a protein in a first conformation or mimic thereof) relative to the second target (e.g., the same protein in a second conformation or mimic thereof; or a second protein). Differences in binding affinity (e.g., for specificity or other comparisons) can be at least 1.5, 2, 3, 4, 5, 10, 15, 20, 30, 40, 50, 70, 80, 90, 100, 500, 1000, 10,000 or $10^5$ fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH 7.4, 150 mM NaCl, 0.005% (v/v) Surfactant P20). These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[\text{Bound}] = N \cdot [\text{Free}]/((1/KA)+[\text{Free}]).$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2 fold higher, to obtain a qualitative measurement of affinity, or to obtain an inference of affinity, e.g., by activity in a functional assay, e.g., an in vitro or in vivo assay.

The term "binding antibody" (or "binding protein" used interchangeably herein) refers to an antibody that can interact with a target molecule. The term "target molecule" is used interchangeably with "ligand." A "plasma kallikrein binding antibody" refers to an antibody that can interact with (e.g., bind) plasma kallikrein, and includes, in particular, antibodies that preferentially or specifically interact with and/or inhibit plasma kallikrein. An antibody inhibits plasma kallikrein if it causes a decrease in the activity of plasma kallikrein as compared to the activity of plasma kallikrein in the absence of the antibody and under the same conditions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

It is possible for one or more framework and/or CDR amino acid residues of a binding protein to include one or more mutations (for example, substitutions (e.g., conservative substitutions or substitutions of non-essential amino acids), insertions, or deletions) relative to a binding protein described herein. A plasma kallikrein binding protein may have mutations (e.g., substitutions (e.g., conservative substitutions or substitutions of non-essential amino acids), insertions, or deletions) (e.g., at least one, two, three, or four, and/or less than 15, 12, 10, 9, 8, 7, 6, 5, 4, 3, or 2 mutations) relative to a binding protein described herein, e.g., mutations which do not have a substantial effect on protein function. The mutations can be present in framework regions, CDRs, and/or constant regions. In some embodiments, the mutations are present in a framework region. In some embodiments, the mutations are present in a CDR. In some embodiments, the mutations are present in a constant region. Whether or not a particular substitution will be tolerated, i.e., will not adversely affect biological properties, such as binding activity, can be predicted, e.g., by evaluating whether the mutation is conservative or by the method of Bowie, et al. (1990) *Science* 247:1306-1310.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

An "epitope" refers to the site on a target compound that is bound by a binding protein (e.g., an antibody such as a Fab or full length antibody). In the case where the target compound is a protein, the site can be entirely composed of amino acid components, entirely composed of chemical modifications of amino acids of the protein (e.g., glycosyl moieties), or composed of combinations thereof. Overlapping epitopes include at least one common amino acid residue, glycosyl group, phosphate group, sulfate group, or other molecular feature.

A "humanized" immunoglobulin variable region is an immunoglobulin variable region that is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762.

An "isolated" antibody refers to an antibody that is removed from at least 90% of at least one component of a natural sample from which the isolated antibody can be obtained. Antibodies can be "of at least" a certain degree of purity if the species or population of species of interest is at least 5, 10, 25, 50, 75, 80, 90, 92, 95, 98, or 99% pure on a weight-weight basis.

The methods described herein involve administering multiple doses of an antibody to a human subject in need thereof. The terms "patient," "subject" or "host" may be used interchangeably. A subject may be a subject that has undergone a prior treatment for HAE, such as a treatment involving an antibody described herein. In some embodiments, the subject is a pediatric subject (e.g., an infant, child, or adolescent subject). In some embodiments, the human subject is an adolescent less than 18 years old. In some embodiments, the human subject is an adolescent between the ages of 12 and 18 years old. In some embodiments, the subject is between the ages of 40 and less than 65 years old.

In some embodiments, the human subject is defined by gender. For example, in some embodiments, the subject is female.

In some embodiments, the human subject is defined by weight. In some embodiments, the human subject weighs less than 50 kg. In some embodiments, the human subject weighs between 50 kg and 75 kg. In some embodiments the human subject weighs between 75 kg and 100 kg. In some embodiments, the human subject weighs 100 kg or more.

In some embodiments, the human subject is defined by prior history of laryngeal attacks or absence thereof. In some embodiments, the subject has experienced at least one (e.g., 1, 2, 3, 4, 5, or more) laryngeal attack (i.e. laryngeal HAE attack) prior to administration of the antibodies described herein. In some embodiments, the subject has not experienced a laryngeal attack prior to administration of the antibodies described herein.

The terms “prekallikrein” and “preplasma kallikrein” are used interchangeably herein and refer to the zymogen form of active plasma kallikrein, which is also known as prekallikrein.

As used herein, the term “substantially identical” (or “substantially homologous”) is used herein to refer to a first amino acid or nucleic acid sequence that contains a sufficient number of identical or equivalent (e.g., with a similar side chain, for example, conserved amino acid substitutions) amino acid residues or nucleotides to a second amino acid or nucleic acid sequence such that the first and second amino acid or nucleic acid sequences have (or encode proteins having) similar activities, e.g., a binding activity, a binding preference, or a biological activity. In the case of antibodies, the second antibody has the same specificity and has at least 50%, at least 25%, or at least 10% of the affinity relative to the same antigen.

Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02. Particular binding proteins may show a difference, e.g., in specificity or binding that are statistically significant (e.g., P value <0.05 or 0.02). The terms “induce”, “inhibit”, “potentiate”, “elevate”, “increase”, “decrease” or the like, e.g., which denote distinguishable qualitative or quantitative differences between two states, may refer to a difference, e.g., a statistically significant difference, between the two states.

A “therapeutically effective dosage” preferably modulates a measurable parameter, e.g., plasma kallikrein activity, by a statistically significant degree or at least about 20%, more preferably by at least about 40%, even more preferably by at least about 60%, and still more preferably by at least about 80% relative to untreated subjects. The ability of a compound to modulate a measurable parameter, e.g., a disease-associated parameter, can be evaluated in an animal model system predictive of efficacy in human disorders and conditions. Alternatively, this property of a composition can be evaluated by examining the ability of the compound to modulate a parameter in vitro.

The term “treating” as used herein refers to the application or administration of a composition including one or more active agents to a subject, who has HAE, a symptom of HAE, is suspected of having HAE, or a predisposition toward or risk of having HAE, with the purpose to cure, heal, alleviate, relieve, alter, remedy, ameliorate, improve, or affect the disease, the symptoms of the disease, or the predisposition toward the disease. “Prophylactic treatment,” also known as “preventive treatment,” refers to a treatment that aims at protecting a person from, or reducing the risk for a disease to which he or she has been, or may be, exposed. In some embodiments, the treatment methods described herein aim at preventing occurrence and/or recurrence of HAE.

The term “preventing” a disease in a subject refers to subjecting the subject to a pharmaceutical treatment, e.g., the administration of a drug, such that at least one symptom of the disease is prevented, that is, administered prior to clinical manifestation of the unwanted condition (e.g., disease or other unwanted state of the host animal) so that it protects the host against developing the unwanted condition. “Preventing” a disease may also be referred to as “prophylaxis” or “prophylactic treatment.”

A “prophylactically effective amount” refers to an amount effective, at dosages and for periods of time necessary, to achieve the desired prophylactic result. Typically, because a prophylactic dose is used in subjects prior to or at an earlier stage of disease, the prophylactically effective amount will be less than the therapeutically effective amount.

Antibodies Binding to Plasma Kallikrein (pKal)

Plasma kallikrein binding antibodies (anti-pKal antibodies) for use in the methods described herein can be full-length (e.g., an IgG (including an IgG1, IgG2, IgG3, IgG4), IgM, IgA (including, IgA1, IgA2), IgD, and IgE) or can include only an antigen-binding fragment (e.g., a Fab, $F(ab')_2$ or scFv fragment. The binding antibody can include two heavy chain immunoglobulins and two light chain immunoglobulins, or can be a single chain antibody. Plasma kallikrein binding antibodies can be recombinant proteins such as humanized, CDR grafted, chimeric, deimmunized, or in vitro generated antibodies, and may optionally include constant regions derived from human germline immunoglobulin sequences. In one embodiment, the plasma kallikrein binding antibody is a monoclonal antibody.

In one aspect, the disclosure features an antibody (e.g., an isolated antibody) that binds to plasma kallikrein (e.g., human plasma kallikrein and/or murine kallikrein) and includes at least one immunoglobulin variable region. For example, the antibody includes a heavy chain (HC) immunoglobulin variable domain sequence and/or a light chain (LC) immunoglobulin variable domain sequence. In one embodiment, the antibody binds to and inhibits plasma kallikrein, e.g., human plasma kallikrein and/or murine kallikrein.

In some embodiments, the antibodies described herein have the same CDR sequences as DX-2930, e.g., heavy chain CDR sequences set forth as SEQ ID NOs: 5-7 and light chain CDR sequences set forth as SEQ ID NOs: 8-10. In some embodiments, the antibody comprises the same CDR sequences as DX-2930 and a LC immunoglobulin variable domain sequence that is at least 85, 88, 89, 90, 91, 92, 93, 94, 95, 96, 97, 98, 99, or 100% identical to a LC variable domain described herein (e.g., overall or in framework regions). In some embodiments, the antibody comprises the same CDR sequences as DX-2930 and an HC immunoglobulin variable domain sequence that is at least 85, 88, 89, 90, 91, 92, 93, 94, 95, 96, 97, 98, 99, or 100% identical to a HC variable domain described herein (e.g., overall or in framework regions). In some embodiments, the antibody comprises the same CDR sequences as DX-2930 and LC sequence that is at least 85, 88, 89, 90, 91, 92, 93, 94, 95, 96, 97, 98, 99, or 100% identical to a LC sequence described herein (e.g., overall or in framework regions). In some embodiments, the antibody comprises the same CDR sequences as DX-2930 and HC sequence that is at least 85, 88, 89, 90, 91, 92, 93, 94, 95, 96, 97, 98, 99, or 100% identical to a HC sequence described herein (e.g., overall or in framework regions).

The plasma kallikrein binding protein may be an isolated antibody (e.g., at least 70, 80, 90, 95, or 99% free of other proteins). In some embodiments, the plasma kallikrein binding antibody, or composition thereof, is isolated from antibody cleavage fragments (e.g., DX-2930) that are inactive or partially active (e.g., bind plasma kallikrein with a $K_i$, app of 5000 nM or greater) compared to the plasma kallikrein binding antibody. For example, the plasma kallikrein binding antibody is at least 70% free of such antibody cleavage fragments; in other embodiments the binding antibody is at least 80%, at least 90%, at least 95%, at least 99% or even 100% free from antibody cleavage fragments that are inactive or partially active.

The plasma kallikrein binding antibody may additionally inhibit plasma kallikrein, e.g., human plasma kallikrein.

In some embodiments, the plasma kallikrein binding antibody does not bind prekallikrein (e.g., human prekallikrein and/or murine prekallikrein), but binds to the active form of plasma kallikrein (e.g., human plasma kallikrein and/or murine kallikrein).

In certain embodiments, the antibody binds at or near the active site of the catalytic domain of plasma kallikrein, or a fragment thereof, or binds an epitope that overlaps with the active site of plasma kallikrein.

The antibody can bind to plasma kallikrein, e.g., human plasma kallikrein, with a binding affinity of at least $10^5$, $10^6$, $10^7$, $10^8$, $10^9$, $10^{10}$ and $10^{11}$ $M^{-1}$. In one embodiment, the antibody binds to human plasma kallikrein with a $K_{off}$ slower than 1Ø$10^{-3}$, 5Ø$10^{-4}$ $s^{-1}$, or 1Ø$10^{-4}$ $s^{-1}$. In one embodiment, the antibody binds to human plasma kallikrein with a $K_{on}$ faster than 1Ø$10^2$, 1Ø$10^3$, or 5Ø$10^3$ $M^{-1}s^{-1}$. In one embodiment, the antibody binds to plasma kallikrein, but does not bind to tissue kallikrein and/or plasma prekallikrein (e.g., the antibody binds to tissue kallikrein and/or plasma prekallikrein less effectively (e.g., 5-, 10-, 50-, 100-, or 1000-fold less or not at all, e.g., as compared to a negative control) than it binds to plasma kallikrein.

In one embodiment, the antibody inhibits human plasma kallikrein activity, e.g., with a Ki of less than $10^{-5}$, $10^{-6}$, $10^{-7}$, $10^{-8}$, $10^{-9}$, and $10^{-10}$ M. The antibody can have, for example, an $IC_{50}$ of less than 100 nM, 10 nM, 1, 0.5, or 0.2 nM. For example, the antibody may modulate plasma kallikrein activity, as well as the production of Factor XIIa (e.g., from Factor XII) and/or bradykinin (e.g., from high-molecular-weight kininogen (HMWK)). The antibody may inhibit plasma kallikrein activity, and/or the production of Factor XIIa (e.g., from Factor XII) and/or bradykinin (e.g., from high-molecular-weight kininogen (HMWK)). The affinity of the antibody for human plasma kallikrein can be characterized by a $K_D$ of less than 100 nm, less than 10 nM, less than 5 nM, less than 1 nM, less than 0.5 nM. In one embodiment, the antibody inhibits plasma kallikrein, but does not inhibit tissue kallikrein (e.g., the antibody inhibits tissue kallikrein less effectively (e.g., 5-, 10-, 50-, 100-, or 1000-fold less or not at all, e.g., as compared to a negative control) than it inhibits plasma kallikrein.

In some embodiments, the antibody has an apparent inhibition constant ($K_{i,app}$) of less than 1000, 500, 100, 5, 1, 0.5 or 0.2 nM.

Plasma kallikrein binding antibodies may have their HC and LC variable domain sequences included in a single polypeptide (e.g., scFv), or on different polypeptides (e.g., IgG or Fab).

In one embodiment, the HC and LC variable domain sequences are components of the same polypeptide chain. In another, the HC and LC variable domain sequences are components of different polypeptide chains. For example, the antibody is an IgG, e.g., IgG1, IgG2, IgG3, or IgG4. The antibody can be a soluble Fab. In other implementations the antibody includes a Fab2', scFv, minibody, scFv::Fc fusion, Fab::HSA fusion, HSA::Fab fusion, Fab::HSA::Fab fusion, or other molecule that comprises the antigen combining site of one of the binding proteins herein. The VH and VL regions of these Fabs can be provided as IgG, Fab, Fab2, Fab2', scFv, PEGylated Fab, PEGylated scFv, PEGylated Fab2, VH::CH1::HSA+LC, HSA::VH::CH1+LC, LC::HSA+VH::CH1, HSA::LC+VH::CH1, or other appropriate construction.

In one embodiment, the antibody is a human or humanized antibody or is non-immunogenic in a human. For example, the antibody includes one or more human antibody framework regions, e.g., all human framework regions, or framework regions at least 85, 88, 89, 90, 91, 92, 93, 94, 95, 96, 97, 98, 99% identical to human framework regions. In one embodiment, the antibody includes a human Fc domain, or an Fc domain that is at least 95, 96, 97, 98, or 99% identical to a human Fc domain.

In one embodiment, the antibody is a primate or primatized antibody or is non-immunogenic in a human. For example, the antibody includes one or more primate antibody framework regions, e.g., all primate framework regions, or framework regions at least 85, 88, 89, 90, 91, 92, 93, 94, 95, 96, 97, 98, 99% identical to primate framework regions. In one embodiment, the antibody includes a primate Fc domain, or an Fc domain that is at least 95, 96, 97, 98, or 99% identical to a primate Fc domain. "Primate" includes humans (*Homo sapiens*), chimpanzees (*Pan troglodytes* and *Pan paniscus* (bonobos)), gorillas (*Gorilla gorilla*), gibons, monkeys, lemurs, aye-ayes (*Daubentonia madagascariensis*), and tarsiers. In some embodiments, the affinity of the primate antibody for human plasma kallikrein is characterized by a $K_D$ of less than 1000, 500, 100, 10, 5, 1, 0.5 nM, e.g., less than 10 nM, less than 1 nM, or less than 0.5 nM.

In certain embodiments, the antibody includes no sequences from mice or rabbits (e.g., is not a murine or rabbit antibody).

In some embodiments, the antibody used in the methods described herein may be DX-2930 as described herein or a functional variant thereof.

In one example, a functional variant of DX-2930 comprises the same complementary determining regions (CDRs) as DX-2930. In another example, the functional variants of DX-2930 may contain one or more mutations (e.g., conservative substitutions) in the FRs of either the $V_H$ or the $V_L$ as compared to those in the $V_H$ and $V_L$ of DX-2930. Preferably, such mutations do not occur at residues which are predicted to interact with one or more of the CDRs, which can be determined by routine technology. In other embodiments, the functional variants described herein contain one or more mutations (e.g., 1, 2, or 3) within one or more of the CDR regions of DX-2930. Preferably, such functional variants retain the same regions/residues responsible for antigen-binding as the parent. In yet other embodiments, a functional variant of DX-2930 may comprise a $V_H$ chain that comprises an amino acid sequence at least 85% (e.g., 90%, 92%, 94%, 95%, 96%, 97%, 98%, or 99%) identical to that of the $V_H$ of DX-2930 and/or a $V_L$ chain that has an amino acid sequence at least 85% (e.g., 90%, 92%, 94%, 95%, 96%, 97%, 98%, or 99%) identical to that of the $V_L$ of DX-2930.

These variants are capable of binding to the active form of plasma kallikrein and preferably do not bind to prekallikrein.

The "percent identity" of two amino acid sequences is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. *Such an algorithm is incorporated into the NBLAST and XBLAST programs* (*version* 2.0) of Altschul, et al. *J. Mol. Biol.* 215:403-10, 1990. BLAST protein searches can be performed with the XBLAST program, score=50, wordlength=3 to obtain amino acid sequences homologous to the protein molecules of interest. Where gaps exist between two sequences, Gapped BLAST can be utilized as described in Altschul et al., *Nucleic Acids Res.* 25 (17): 3389-3402, 1997. When utilizing BLAST and Gapped BLAST programs, the default parameters of the respective programs (e.g., XBLAST and NBLAST) can be used.

In some embodiments, the antibody used in the methods and compositions described herein may be the DX-2930 antibody. The heavy and light chain full and variable sequences for DX-2930 are provided below, with signal sequences in italics. The CDRs are boldfaced and underlined.

DX-2930 Heavy Chain Amino Acid Sequence (451 amino acids, 49439.02 Da)

MGWSCILFLVATATGAHSEVQLLESGG-GLVQPGGSLRLSCAASGFTFSHYIMMWVRQ APGK-GLEWVSGIYSSGGITVYADSVKGRFTISRDNSKNT-LYLQMNSLRAEDTAVYY CAYRRIGVPRRDEFDIWGQGTMVTVSSASTKGPSVF-PLAPSSKSTSGGTAALGCLV KDYF-PEPVTVSWNSGALTSGVHTFPAVLQSSGLYS-LSSVVTVPSSSLGTQTYICNVNH KPSNTKVDKRVEPKSCDKTHTCPPCPA-PELLGGPSVFLFPPKPKDTLMISRTPEVTCV VVDVSHEDPEVKFNWYVDGVEVHNAKTKPRE-EQYNSTYRVVSVLTVLHQDWLNG KEYKCKVSNKA-LPAPIEKTISKAKGQPREPQVYTLPPSREEMT-KNQVSLTCLVKGFYP SDIA VEWESNGQPENNYKTTPPVLDSDGSFFLYSK-LTVDKSRWQQGNVFSCSVMHE ALHNHYTQKSLSL-SPG (SEQ ID NO: 1)

DX-2930 Light Chain Amino Acid Sequence (213 amino acids, 23419.08 Da)

MGWSCILFLVATATGAHSDIQMTQSPSTL-SASVGDRVTITCRASQSISSWLAWYQQKP GKAPKLLIYKASTLESGVPSRFSGSGSGTEFTLTIS-SLQPDDFATYYCQQYNTYWTF GQGTKVEIKRTVAAPSVFIFPPSDEQLKSG-TASVVCLLNNFYPREAKVQWKVDNALQ SGNSQESVTEQDSKDSTYSLSSTLTL-SKADYEKHKVYACEVTHQGLSSPVTKSFNRG EC (SEQ ID NO: 2)

DX-2930 Heavy Chain Variable Domain Amino Acid Sequence

EVQLLESGGGLVQPGGSLRLSCAASGFTFSHY-IMMWVRQAPGKGLEWVSGIYSSGG ITVY-ADSVKGRFTISRDNSKNTLYLQMNSLRAEDTAVYY-CAYRRIGVPRRDEFDIW GQGTMVTVSS (SEQ ID NO: 3)

DX-2930 Light Chain Variable Domain Amino Acid Sequence

DIQMTQSPSTLSASVGDRVTITCRASQSISS-WLAWYQQKPGKAPKLLIYKASTLESG VPSRFSGSGSGTEFTLTISSLQPDDFATYY-CQQYNTYWTFGQGTKVEIK (SEQ ID NO: 4)

TABLE 1A

CDRs for DX-2930.

| CDR | Amino acid sequence |
|---|---|
| Heavy chain CDR1 | HYIMM (SEQ ID NO: 5) |
| Heavy chain CDR2 | GIYSSGGITVYADSVKG (SEQ ID NO: 6) |
| Heavy chain CDR3 | RRIGVPRRDEFDI (SEQ ID NO: 7) |
| Light chain CDR1 | RASQSISSWLA (SEQ ID NO: 8) |
| Light chain CDR2 | KASTLES (SEQ ID NO: 9) |
| Light chain CDR3 | QQYNTYWT (SEQ ID NO: 10) |

Antibody Preparation

An antibody as described herein (e.g., DX-2930) can be made by any method known in the art. See, for example, Harlow and Lane, (1988) *Antibodies: A Laboratory Manual*, Cold Spring Harbor Laboratory, New York and Greenfield, (2013) *Antibodies: A Laboratory Manual*, Second edition, Cold Spring Harbor Laboratory Press.

The sequence encoding the antibody of interest, e.g., DX-2930, may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the activity of PKal. It will be apparent to one of skill in the art that one or more polynucleotide changes can be made to the antibody and still maintain its binding specificity to the target antigen.

Some antibodies, e.g., Fabs, can be produced in bacterial cells, e.g., *E. coli* cells (see e.g., Nadkarni, A. et al., 2007 *Protein Expr Purif* 52 (1): 219-29). For example, if the Fab is encoded by sequences in a phage display vector that includes a suppressible stop codon between the display entity and a bacteriophage protein (or fragment thereof), the vector nucleic acid can be transferred into a bacterial cell that cannot suppress a stop codon. In this case, the Fab is not fused to the gene III protein and is secreted into the periplasm and/or media.

Antibodies can also be produced in eukaryotic cells. In one embodiment, the antibodies (e.g., scFv's) are expressed in a yeast cell such as *Pichia* (see, e.g., Powers et al., 2001, *J. Immunol. Methods.* 251:123-35; Schoonooghe S. et al., 2009 *BMC Biotechnol.* 9:70; Abdel-Salam, H A. et al., 2001 *Appl Microbiol Biotechnol* 56 (1-2): 157-64; Takahashi K. et al., 2000 *Biosci Biotechnol Biochem* 64 (10): 2138-44; Edqvist, J. et al., 1991 *J Biotechnol* 20 (3): 291-300), Hanseula, or *Saccharomyces*. One of skill in the art can optimize antibody production in yeast by optimizing, for example, oxygen conditions (see e.g., Baumann K., et al. 2010 *BMC Syst. Biol.* 4:141), osmolarity (see e.g., Dragosits, M. et al., 2010 *BMC Genomics* 11:207), temperature (see e.g., Dragosits, M. et al., 2009 *J Proteome Res.* 8 (3): 1380-92), fermentation conditions (see e.g., Ning, D. et al. 2005 *J. Biochem*, and *Mol. Biol.* 38 (3): 294-299), strain of yeast (see e.g., Kozyr, A V et al. 2004 *Mol Biol* (Mosk) 38 (6): 1067-75; Horwitz, A H. et al., 1988 *Proc Natl Acad Sci*

*USA* 85 (22): 8678-82; Bowdish, K. et al. 1991 *J Biol Chem* 266 (18): 11901-8), overexpression of proteins to enhance antibody production (see e.g., Gasser, B. et al., 2006 *Biotechol. Bioeng.* 94 (2): 353-61), level of acidity of the culture (see e.g., Kobayashi H., et al., 1997 *FEMS Microbiol Lett* 152 (2): 235-42), concentrations of substrates and/or ions (see e.g., Ko J H. et al., 2996 *Appl Biochem Biotechnol* 60 (1): 41-8). In addition, yeast systems can be used to produce antibodies with an extended half-life (see e.g., Smith, B J. et al. 2001 *Bioconjug Chem* 12 (5): 750-756).

In one preferred embodiment, antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin, 1980*, Proc. Natl. Acad. Sci. USA* 77:4216-4220, used with a DHFR selectable marker, e.g., as described in Kaufman and Sharp, 1982*, Mol. Biol.* 159:601 621), lymphocytic cell lines, e.g., NS0 myeloma cells and SP2 cells, COS cells, HEK293T cells (*J. Immunol. Methods* (2004) 289 (1-2): 65-80), and a cell from a transgenic animal, e.g., a transgenic mammal. For example, the cell is a mammary epithelial cell.

In some embodiments, plasma kallikrein binding antibodies are produced in a plant or cell-free based system (see e.g., Galeffi, P., et al., 2006 *J Transl Med* 4:39).

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

In an exemplary system for recombinant expression of an antibody, or antigen-binding portion thereof, a recombinant expression vector encoding both the antibody heavy chain and the antibody light chain is introduced into dhfr CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G coupled matrix.

For antibodies that include an Fc domain, the antibody production system may produce antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement Clq (Burton and Woof, 1992*, Adv. Immunol.* 51:1-84; Jefferis et al., 1998*, Immunol. Rev.* 163:59-76). In one embodiment, the Fc domain is produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

Pharmaceutical Compositions

An antibody as described herein (e.g., DX-2930) can be present in a composition, e.g., a pharmaceutically acceptable composition or pharmaceutical composition. The antibody as described herein (e.g., DX-2930) can be formulated together with a pharmaceutically acceptable carrier. In some embodiments, 150 mg or 300 mg of DX-2930 antibody are present in a composition optionally with a pharmaceutically acceptable carrier, e.g., a pharmaceutically acceptable composition or pharmaceutical composition.

A pharmaceutically acceptable carrier includes any and all solvents, dispersion media, coatings, antibacterial and antifungal agents, isotonic and absorption delaying agents, and the like that are physiologically compatible. Preferably, the carrier is suitable for subcutaneous, intravenous, intramuscular, parenteral, spinal, or epidermal administration (e.g., by injection or infusion), although carriers suitable for inhalation and intranasal administration are also contemplated.

The pharmaceutically acceptable carrier in the pharmaceutical composition described herein may include one or more of a buffering agent, an amino acid, and a tonicity modifier. Any suitable buffering agent or combination of buffering agents may be used in the pharmaceutical composition described herein to maintain or aid in maintaining an appropriate pH of the composition. Non-limiting examples of buffering agents include sodium phosphate, potassium phosphate, citric acid, sodium succinate, histidine, Tris, and sodium acetate. In some embodiments, the buffering agents may be at a concentration of about 5-100 mM, 5-50 mM, 10-50 mM, 15-50 mM, or about 15-40 mM. For example, the one or more buffering agents may be at a concentration of about 15 mM, 16 mM, 17 mM, 18 mM, 19 mM, 20 mM, 21 mM, 22 mM, 23 mM, 24 mM, 25 mM, 26 mM, 27 mM, 28 mM, 29 mM, 30 mM, 31 mM, 32 mM, 33 mM, 35 mM, 36 mM, 37 mM, 38 mM, 39 mM, or about 40 mM. In some examples, the pharmaceutically acceptable carrier comprises sodium phosphate and citric acid, which may be at a concentration of about 30 mM and about 19 mM, respectively.

In some embodiments, the pharmaceutically acceptable carrier includes one or more amino acids, which may decrease aggregation of the antibody and/or increase stability of the antibody during storage prior to administration. Exemplary amino acids for use in making the pharmaceutical compositions described herein include, but are not limited to, alanine, arginine, asparagine, aspartic acid, glycine, histidine, lysine, proline, or serine. In some examples, the concentration of the amino acid in the pharmaceutical composition may be about 5-100 mM, 10-90 mM, 20-80 mM, 30-70 mM, 40-60 mM, or about 45-55 mM. In some examples, the concentration of the amino acid (e.g., histidine) may be about 40 mM, 41 mM, 42 mM, 43 mM, 44 mM, 45 mM, 46 mM, 47 mM, 48 mM, 49 mM, 50 mM, 51 mM, 52 mM, 53 mM, 54 mM, 55 mM, 56 mM, 57 mM, 58 mM, 59 mM, or about 60 mM. In one example, the pharmaceutical composition contains histidine at a concentration of about 50 mM.

Any suitable tonicity modifier may be used for preparing the pharmaceutical compositions described herein. In some embodiments, the tonicity modifier is a salt or an amino acid. Examples of suitable salts include, without limitation, sodium chloride, sodium succinate, sodium sulfate, potassium chloride, magnesium chloride, magnesium sulfate, and calcium chloride. In some embodiments, the tonicity modifier in the pharmaceutical composition may be at a concentration of about 10-150 mM, 50-150 mM, 50-100 mM, 75-100 mM, or about 85-95 mM. In some embodiments, the tonicity modifier may be at a concentration of about 80 mM, 81 mM, 82 mM, 83 mM, 84 mM, 85 mM, 86 mM, 87 mM, 88 mM, 89 mM, 90 mM, 91 mM, 92 mM, 93 mM, 94 mM, 95 mM, 96 mM, 97 mM, 98 mM, 99 mM, or about 100 mM. In one example, the tonicity modifier may be sodium chloride, which may be at a concentration of about 90 mM.

The pharmaceutically acceptable carrier in the pharmaceutical compositions described herein may further comprise one or more pharmaceutically acceptable excipients. In general, pharmaceutically acceptable excipients are pharmacologically inactive substances. Non-limiting examples of excipients include lactose, glycerol, xylitol, sorbitol, mannitol, maltose, inositol, trehalose, glucose, bovine serum albumin (BSA), dextran, polyvinyl acetate (PVA), hydroxypropyl methylcellulose (HPMC), polyethyleneimine (PEI), gelatin, polyvinylpyrrolidone (PVP), hydroxyethylcellulose (HEC), polyethylene glycol (PEG), ethylene glycol, glycerol, dimethysulfoxide (DMSO), dimethylformamide (DMF), polyoxyethylene sorbitan monolaurate (Tween-20), polyoxyethylene sorbitan monooleate (Tween-80), sodium dodecyl sulphate (SDS), polysorbate, polyoxyethylene copolymer, potassium phosphate, sodium acetate, ammonium sulfate, magnesium sulfate, sodium sulfate, trimethylamine N-oxide, betaine, zinc ions, copper ions, calcium ions, manganese ions, magnesium ions, CHAPS, sucrose monolaurate and 2-O-beta-mannoglycerate. In some embodiments, the pharmaceutically acceptable carrier comprises an excipient between about 0.001%-0.1%, 0.001%-0.05%, 0.005-0.1%, 0.005%-0.05%, 0.008%-0.05%, 0.008%-0.03% or about 0.009%-0.02%. In some embodiments, the excipient is at about 0.005%, 0.006%, 0.007%, 0.008%, 0.009%, 0.01%, 0.02%, 0.03%, 0.04%, 0.05%, 0.06%, 0.07%, 0.08%, 0.09%, or about 0.1%. In some embodiments, the excipient is polyoxyethylene sorbitan monooleate (Tween-80). In one example, the pharmaceutically acceptable carrier contains 0.01% Tween-80.

In some examples, the pharmaceutical composition described herein comprises the anti-pKal antibody as also described herein (e.g., DX-2930), and one or more of sodium phosphate (e.g., sodium phosphate dibasic dihydrate), citric acid (e.g., citric acid monohydrate), histidine (e.g., L-histidine), sodium chloride, and Polysorbate 80. For example, the pharmaceutical composition may comprise the antibody, sodium phosphate, citric acid, histidine, sodium chloride, and Polysorbate 80. In some examples, the antibody is formulated in about 30 mM sodium phosphate, about 19 mM citric acid, about 50 mM histidine, about 90 mM sodium chloride, and about 0.01% Polysorbate 80. The concentration of the antibody (e.g., DX-2930) in the composition can be about 150 mg/mL or 300 mg/mL. In one example, the composition comprises or consists of about 150 mg DX-2930 per 1 mL solution, about 30 mM sodium phosphate dibasic dihydrate, about 19 mM (e.g., 19.6 mM) citric acid monohydrate, about 50 mM L-histidine, about 90 mM sodium chloride, and about 0.01% Polysorbate 80. In another example, the composition comprises or consists of about 300 mg DX-2930 per 1 mL solution, about 30 mM sodium phosphate dibasic dihydrate, about 19 mM (e.g., 19.6 mM) citric acid monohydrate, about 50 mM L-histidine, about 90 mM sodium chloride, and about 0.01% Polysorbate 80.

A pharmaceutically acceptable salt is a salt that retains the desired biological activity of the compound and does not impart any undesired toxicological effects (see, e.g., Berge, S. M., et al., 1977, *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids, and the like. Base addition salts include those derived from alkaline earth metals, such as sodium, potassium, magnesium, calcium, and the like, as well as from nontoxic organic amines, such as N,N'-dibenzylethylenediamine, N-methylglucamine, chloroprocaine, choline, diethanolamine, ethylenediamine, procaine, and the like.

The compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Many compositions are in the form of injectable or infusible solutions, such as compositions similar to those used for administration of humans with antibodies. An exemplary mode of administration is parenteral (e.g., intravenous, subcutaneous, intraperitoneal, intramuscular). In one embodiment, the plasma kallikrein binding protein is administered by intravenous infusion or injection. In another embodiment, the plasma kallikrein binding protein is administered by intramuscular injection. In another embodiment, the plasma kallikrein binding protein is administered by subcutaneous injection. In another preferred embodiment, the plasma kallikrein binding protein is administered by intraperitoneal injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In some embodiments, the antibody is administered subcutaneously.

The composition can be formulated as a solution, microemulsion, dispersion, liposome, or other ordered structure suitable to high drug concentration. Sterile injectable solutions can be prepared by incorporating the binding protein in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An antibody as described herein (e.g., DX-2930) can be administered by a variety of methods, including intravenous injection, subcutaneous injection, or infusion. For example, for some therapeutic applications, the antibody can be administered by intravenous infusion at a rate of less than 30, 20, 10, 5, or 1 mg/min to reach a dose of about 1 to 100 mg/m2 or 7 to 25 mg/m2. The route and/or mode of administration will vary depending upon the desired results. In certain embodiments, the active compound may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are available. See, e.g., Sustained and Controlled Release Drug Delivery Systems, J. R. Robinson, ed., 1978, Marcel Dekker, Inc., New York.

Pharmaceutical compositions can be administered with medical devices. For example, in one embodiment, a pharmaceutical composition disclosed herein can be administered with a device, e.g., a needleless hypodermic injection device, a pump, or implant.

In certain embodiments, an antibody as described herein (e.g., DX-2930) can be formulated to ensure proper distribution in vivo. For example, the blood-brain barrier (BBB) excludes many highly hydrophilic compounds. To ensure that the therapeutic compounds disclosed herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade, 1989, *J. Clin. Pharmacol.* 29:685).

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms can be dictated by and directly dependent on (a) the unique characteristics of the active compound and the particular therapeutic effect to be achieved, and (b) the limitations inherent in the art of compounding such an active compound for the treatment of sensitivity in individuals.

An exemplary, non-limiting range for a therapeutically or prophylactically effective amount of an antibody as described herein (e.g., DX-2930) is about 150 mg or 300 mg. As will be understood by one of ordinary skill in the art, a therapeutically or prophylactically effective amount of an antibody may be lower for a pediatric subject than for an adult subject. In some embodiments, the effective amount that is administered to a pediatric subject is a fixed dose or a weight based dose. In some embodiments, effective amount that is less than about 150 mg or 300 mg is administered to a pediatric subject. In some embodiments, a therapeutically or prophylactically effective amount of an antibody is administered every two weeks or every four weeks for a first treatment period. In some embodiments, the antibody may be administered to the subject for a second treatment period. In some embodiments, the therapeutically or prophylactically effective amount of the antibody in the first treatment period is different than the therapeutically or prophylactically effective amount of the antibody in the second treatment period. In some embodiments, the therapeutically or prophylactically effective amount of the antibody in the first treatment period is 150 mg and the therapeutically or prophylactically effective amount of the antibody in the second treatment period is 300 mg. In some embodiments, the therapeutically or prophylactically effective amount of the antibody in the first treatment period is the same as the therapeutically or prophylactically effective amount of the antibody in the second treatment period. In one example, therapeutically or prophylactically effective amount of the antibody in the first treatment period and the second treatment period is 300 mg.

In some embodiments, an exemplary, non-limiting range for a therapeutically or prophylactically effective amount of an antibody as described herein (e.g., DX-2930) is about 300 mg. In some embodiments, a therapeutically or prophylactically effective amount of an antibody is administered in a single dose. If the subject experiences a HAE attack, the antibody may be further administered to the subject in multiple doses, such in doses of about 300 mg administered every two weeks.

Kits

An antibody as described herein (e.g., DX-2930) can be provided in a kit, e.g., as a component of a kit. For example, the kit includes (a) a DX-2930 antibody, e.g., a composition (e.g., a pharmaceutical composition) that includes the antibody, and, optionally (b) informational material. The informational material can be descriptive, instructional, marketing or other material that relates to a method described herein and/or the use of an antibody as described herein (e.g., DX-2930), e.g., for a method described herein. In some embodiments, the kit comprises one or more doses of DX-2930. In some embodiments, the one or more doses are 150 mg or 300 mg.

The informational material of the kit is not limited in its form. In one embodiment, the informational material can include information about production of the compound, molecular weight of the compound, concentration, date of expiration, batch or production site information, and so forth. In one embodiment, the informational material relates to using the antibody to treat, prevent, or diagnosis of disorders and conditions, e.g., a plasma kallikrein associated disease or condition.

In one embodiment, the informational material can include instructions to administer an antibody as described herein (e.g., DX-2930) in a suitable manner to perform the methods described herein, e.g., in a suitable dose, dosage form, mode of administration or dosing schedule (e.g., a dose, dosage form, dosing schedule or mode of administration described herein). In another embodiment, the informational material can include instructions to administer an antibody as described herein (e.g., DX-2930) to a suitable subject, e.g., a human, e.g., a human having, or at risk for, a plasma kallikrein associated disease or condition. For example, the material can include instructions to administer an antibody as described herein (e.g., DX-2930) to a patient with a disorder or condition described herein, e.g., a plasma kallikrein associated disease, e.g., according to a dosing schedule described herein. The informational material of the kits is not limited in its form. In many cases, the informational material, e.g., instructions, is provided in print but may also be in other formats, such as computer readable material.

An antibody as described herein (e.g., DX-2930) can be provided in any form, e.g., liquid, dried or lyophilized form. It is preferred that an antibody be substantially pure and/or sterile. When an antibody is provided in a liquid solution, the liquid solution preferably is an aqueous solution, with a sterile aqueous solution being preferred. When an antibody is provided as a dried form, reconstitution generally is by the addition of a suitable solvent. The solvent, e.g., sterile water or buffer, can optionally be provided in the kit.

The kit can include one or more containers for the composition containing an antibody as described herein (e.g., DX-2930). In some embodiments, the kit contains separate containers, dividers or compartments for the composition and informational material. For example, the composition can be contained in a bottle, vial, or syringe, and the informational material can be contained in association with the container. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of an antibody as described herein (e.g., DX-2930). For example, the kit includes a plurality of syringes, ampules, foil packets, or blister packs, each containing a single unit dose of an antibody as described herein (e.g., DX-2930). The containers of the kits can be air tight, waterproof (e.g., impermeable to changes in moisture or evaporation), and/or light-tight.

The kit optionally includes a device suitable for administration of the composition, e.g., a syringe, or any such delivery device. In one embodiment, the device is an implantable device that dispenses metered doses of the antibody. The disclosure also features a method of providing a kit, e.g., by combining components described herein.

Treatment

In some aspects, the disclosure provides the use of an antibody as described herein (e.g., DX-2930) in treating HAE. In particular, the present disclosure provides a treatment regimen that allows for reducing the dosage of DX-2930 and/or extending the dosing schedule (e.g., from once every two weeks to once every four weeks) for patients whose disease is well controlled (e.g., free of attack in a period of time such as 4-9 months) and/or for patients with low body weight (e.g., pediatric patients).

(i) Hereditary Angioedema

Hereditary angioedema (HAE) is also known as "Quincke edema," C1 esterase inhibitor deficiency, C1 inhibitor deficiency, and hereditary angioneurotic edema (HANE). HAE is characterized by unpredictable, recurrent attacks of severe subcutaneous or submucosal swelling (angioedema), which can affect, e.g., the limbs, face, genitals, gastrointestinal tract, and airway (Zuraw, 2008). Symptoms of HAE include, e.g., swelling in the arms, legs, lips, eyes, tongue, and/or throat; airway blockage that can involve throat (larynx) swelling, sudden hoarseness and/or cause death from asphyxiation (Bork et al., 2012; Bork et al., 2000). Approximately 50% of all HAE patients will experience a laryngeal attack in their lifetime, and there is no way to predict which patients are at risk of a laryngeal attack (Bork et al., 2003; Bork et al., 2006). HAE symptoms also include repeat episodes of abdominal cramping without obvious cause; and/or swelling of the intestines, which can be severe and can lead to abdominal cramping, vomiting, dehydration, diarrhea, pain, shock, and/or intestinal symptoms resembling abdominal emergencies, which may lead to unnecessary surgery (Zuraw, 2008). Swelling may last up to five or more days. About one-third of individuals with this HAE develop a non-itchy rash called erythema *marginatum* during an attack. Most patients suffer multiple attacks per year.

HAE is an orphan disorder, the exact prevalence of which is unknown, but current estimates range from 1 per 10,000 to 1 per 150,000 persons, with many authors agreeing that 1 per 50,000 is likely the closest estimate (Bygum, 2009; Goring et al., 1998; Lei et al., 2011; Nordenfelt et al., 2014; Roche et al., 2005).

Plasma kallikrein plays a critical role in the pathogenesis of HAE attacks (Davis, 2006; Kaplan and Joseph, 2010). In normal physiology, C1-INH regulates the activity of plasma kallikrein as well as a variety of other proteases, such as C1r, C1s, factor XIa, and factor XIIa. Plasma kallikrein regulates the release of bradykinin from high molecular weight kininogen (HMWK). Due to a deficiency of C1-INH in HAE, uncontrolled plasma kallikrein activity occurs and leads to the excessive generation of bradykinin. Bradykinin is a vasodilator which is thought to be responsible for the characteristic HAE symptoms of localized swelling, inflammation, and pain (Craig et al., 2012; Zuraw et al., 2013).

Swelling of the airway can be life threatening and causes death in some patients. Mortality rates are estimated at 15-33%. HAE leads to about 15,000-30,000 emergency department visits per year.

Trauma or stress, e.g., dental procedures, sickness (e.g., viral illnesses such as colds and the flu), menstruation, and surgery can trigger an attack of angioedema. To prevent acute attacks of HAE, patients can attempt to avoid specific stimuli that have previously caused attacks. However, in many cases, an attack occurs without a known trigger. Typically, HAE symptoms first appear in childhood and worsen during puberty. On average, untreated individuals have an attack every 1 to 2 weeks, and most episodes last for about 3 to 4 days (ghr.nlm.nih.gov/condition/hereditary-angioedema). The frequency and duration of attacks vary greatly among people with hereditary angioedema, even among people in the same family.

There are three types of HAE, known as types I, II, and III, all of which can be treated by the methods described herein. It is estimated that HAE affects 1 in 50,000 people, that type I accounts for about 85 percent of cases, type II accounts for about 15 percent of cases, and type III is very rare. Type III is the most newly described form and was originally thought to occur only in women, but families with affected males have been identified.

HAE is inherited in an autosomal dominant pattern, such that an affected person can inherit the mutation from one affected parent. New mutations in the gene can also occur, and thus HAE can also occur in people with no history of the disorder in their family. It is estimated that 20-25% of cases result from a new spontaneous mutation.

Mutations in the SERPING1 gene cause hereditary angioedema type I and type II. The SERPING1 gene provides instructions for making the C1 inhibitor protein, which is important for controlling inflammation. C1 inhibitor blocks the activity of certain proteins that promote inflammation. Mutations that cause hereditary angioedema type I lead to reduced levels of C1 inhibitor in the blood. In contrast, mutations that cause type II result in the production of a C1 inhibitor that functions abnormally. Approximately 85% of patients have Type I HAE, characterized by very low production of functionally normal C1-INH protein, while the remaining approximately 15% of patients have Type II HAE and produce normal or elevated levels of a functionally impaired C1-INH (Zuraw, 2008). Without the proper levels of functional C1 inhibitor, excessive amounts of bradykinin are generated from high molecular weight kininogen (HMWK), and there is increased vascular leakage mediated by bradykinin binding to the B2 receptor (B2-R) on the surface of endothelial cells (Zuraw, 2008). Bradykinin promotes inflammation by increasing the leakage of fluid through the walls of blood vessels into body tissues. Excessive accumulation of fluids in body tissues causes the episodes of swelling seen in individuals with hereditary angioedema type I and type II.

Mutations in the F12 gene are associated with some cases of hereditary angioedema type III. The F12 gene provides instructions for making coagulation factor XII. In addition to playing a critical role in blood clotting (coagulation), factor XII is also an important stimulator of inflammation and is involved in the production of bradykinin. Certain mutations in the F12 gene result in the production of factor XII with increased activity. As a result, more bradykinin is generated and blood vessel walls become more leaky, which leads to episodes of swelling. The cause of other cases of hereditary angioedema type III remains unknown. Mutations in one or more as-yet unidentified genes may be responsible for the disorder in these cases.

HAE can present similarly to other forms of angioedema resulting from allergies or other medical conditions, but it differs significantly in cause and treatment. When hereditary angioedema is misdiagnosed as an allergy, it is most commonly treated with antihistamines, steroids, and/or epinephrine, which are typically ineffective in HAE, although epinephrine can be used for life-threatening reactions. Misdiagnoses have also resulted in unnecessary exploratory surgery for patients with abdominal swelling, and in some HAE patients abdominal pain has been incorrectly diagnosed as psychosomatic.

Like adults, children with HAE can suffer from recurrent and debilitating attacks. Symptoms may present very early in childhood, and upper airway angioedema has been reported in HAE patients as young as the age of 3 (Bork et al., 2003). In one case study of 49 pediatric HAE patients, 23 had suffered at least one episode of airway angioedema by the age of 18 (Farkas, 2010). An important unmet medical need exists among children with HAE, especially adolescents, since the disease commonly worsens after puberty (Bennett and Craig, 2015; Zuraw, 2008).

C1 inhibitor therapies, as well as other therapies for HAE, are described in Kaplan, A. P., *J Allergy Clin Immunol,* 2010, 126 (5): 918-925.

Acute treatment of HAE attacks is provided to halt progression of the edema as quickly as possible. C1 inhibitor concentrate from donor blood, which is administered intravenously, is one acute treatment; however, this treatment is not available in many countries. In emergency situations where C1 inhibitor concentrate is not available, fresh frozen plasma (FFP) can be used as an alternative, as it also contains C1 inhibitor.

Purified C1 inhibitor, derived from human blood, has been used in Europe since 1979. Several C1 inhibitor treatments are now available in the U.S. and two C1 inhibitor products are now available in Canada. Berinert P (CSL Behring), which is pasteurized, was approved by the F.D.A. in 2009 for acute attacks. Cinryze (ViroPharma), which is nanofiltered, was approved by the F.D.A. in 2008 for prophylaxis. Rhucin (Pharming) is a recombinant C1 inhibitor under development that does not carry the risk of infectious disease transmission due to human blood-borne pathogens.

Treatment of an acute HAE attack also can include medications for pain relief and/or IV fluids.

Other treatment modalities can stimulate the synthesis of C1 inhibitor, or reduce C1 inhibitor consumption. Androgen medications, such as danazol, can reduce the frequency and severity of attacks by stimulating production of C1 inhibitor.

*Helicobacter pylori* can trigger abdominal attacks. Antibiotics to treat *H. pylori* will decrease abdominal attacks.

Newer treatments attack the contact cascade. Ecallantide (KALBITOR®, DX-88, Dyax) inhibits plasma kallikrein and has been approved in the U.S., Icatibant (FIRAZYR®, Shire) inhibits the bradykinin B2 receptor, and has been approved in Europe and the U.S.

Diagnosis of HAE can rely on, e.g., family history and/or blood tests. Laboratory findings associated with HAE types I, II, and III are described, e.g., in Kaplan, A. P., *J Allergy Clin Immunol,* 2010, 126 (5): 918-925. In type I HAE, the level of C1 inhibitor is decreased, as is the level of C4, whereas Clq level is normal. In type II HAE, the level of C1 inhibitor is normal or increased; however, C1 inhibitor function is abnormal. C4 level is decreased and Clq level is normal. In type III, the levels of C1 inhibitor, C4, and Clq can all be normal.

Symptoms of HAE can be assessed, for example, using questionnaires, e.g., questionnaires that are completed by patients, clinicians, or family members. Such questionnaires are known in the art and include, for example, visual analog scales. See, e.g., McMillan, C. V. et al. *Patient.* 2012; 5 (2): 113-26. In some embodiments, the subject has HAE type I or HAE type II. HAE type I or HAE type II may be diagnosed using any method known in the art, such as by clinical history consistent with HAE (e.g., subcutaneous or mucosal, nonpruritic swelling episodes) or diagnostic testing (e.g., C1-INH functional testing and C4 level assessment).

(ii) Reducing Dosage of DX-2930 in HAE Treatment

The disclosure provides methods of treating (e.g., ameliorating, stabilizing, or eliminating one or more symptoms) of hereditary angioedema (HAE) by administering to an HAE patient with an anti-pKal antibody such as DX-2930 at a first dosing schedule, for example 300 mg every two weeks, for a first treatment period (e.g., 4-9 weeks). Occurrence of HAE attack is monitored in the patient subject to the first period of treatment following standard medical practice. When the patient is free of HAE attack in the first treatment period, dosage of the antibody can be reduced and/or dosing interval of the antibody can be prolonged, for example, reduced to 300 mg every four weeks or 300 mg every six weeks.

In some embodiments, the human patient may have a low body weight. As used herein, a low body weight, when applied to an adult, refers to the body weight of the adult that is significantly lower than the average body weight of adults with matched physical features, such as height, age, gender, etc. For example, an adult patient having a low body weight may have a body weight that is at least 20% (e.g., 30%, 40%, 50%, or above) lower than the average of body weight of adults with matched physical features as noted above. In some instances, the human patient is an adult HAE patient having a body weight lower than 40 kg (e.g., lower than 35 kg, lower than 30 kg, lower than 25 kg, etc.). In other instances, the human patient having a low body weight may be a pediatric patient (e.g., younger than 15 yrs). Such a pediatric patient may have a body weight less than 30 kg (e.g., lower than 25 kg, lower than 20 kg, lower than 15 kg, or lower than 10 kg, etc.).

In some embodiments, the subject may be defined by gender. For example, in some embodiments, the subject is female. In other embodiments, the subject is male.

In some embodiments, the human subject is defined by prior history of laryngeal attacks or absence thereof. In some embodiments, the subject has experienced at least one (e.g., 1, 2, 3, 4, 5, or more) laryngeal attack (i.e. laryngeal HAE attack) prior to administration of the antibodies described herein. In some embodiments, the subject has not experienced a laryngeal attack prior to administration of the antibodies described herein.

Treating includes administering an amount effective to alleviate, relieve, alter, remedy, ameliorate, improve or affect the disorder, the symptoms of the disorder or the predisposition toward the disorder. The treatment may also delay onset, e.g., prevent onset, or prevent deterioration of a disease or condition.

Methods of administering DX-2930 antibodies are also described in "Pharmaceutical Compositions." Suitable dosages of the antibody used can depend on the age and weight of the subject and the particular drug used. The antibody can be used as competitive agents to inhibit, reduce an undesirable interaction, e.g., between plasma kallikrein and its substrate (e.g., Factor XII or HMWK). The dose of the antibody can be the amount sufficient to block 90%, 91%, 92%, 93%, 94%, 95%, 96%, 97%, 98% 99%, or 99.9% of the activity of plasma kallikrein in the patient, especially at the site of disease. In some embodiments, 150 mg or 300 mg of the antibody is administered every two weeks or every four weeks. In some embodiments, the antibody is administered to the subject in a first treatment period comprising administration of 150 mg or 300 mg of the antibody every two weeks or every four weeks. In some embodiments, the antibody is administered to the subject in a second treatment period following the first treatment period. In some embodiments, 300 mg of the antibody is administered in a single dose. If the subject experiences an HAE attack after the single dose, the antibody may be administered at 300 mg every two weeks in the first treatment period.

In one embodiment, the antibodies are used to inhibit an activity (e.g., inhibit at least one activity of plasma kallikrein, e.g., reduce Factor XIIa and/or bradykinin production) of plasma kallikrein, e.g., in vivo. The binding proteins can be used by themselves or conjugated to an agent, e.g., a cytotoxic drug, cytotoxin enzyme, or radioisotope.

The antibodies can be used directly in vivo to eliminate antigen-expressing cells via natural complement-dependent cytotoxicity (CDC) or antibody dependent cellular cytotoxicity (ADCC). The antibodies described herein can include complement binding effector domain, such as the Fc portions from IgG1, -2, or -3 or corresponding portions of IgM which bind complement. In one embodiment, a population of target cells is ex vivo treated with an antibody described herein and appropriate effector cells. The treatment can be supplemented by the addition of complement or serum containing complement. Further, phagocytosis of target cells coated with an antibody described herein can be improved by binding of complement proteins. In another embodiment target, cells coated with the antibody which includes a complement binding effector domain are lysed by complement.

Methods of administering DX-2930 antibodies are described in "Pharmaceutical Compositions." Suitable dosages of the molecules used will depend on the age and weight of the subject and the particular drug used. The antibodies can be used as competitive agents to inhibit or reduce an undesirable interaction, e.g., between a natural or pathological agent and the plasma kallikrein.

A therapeutically effective amount of an antibody as described herein, can be administered to a subject having, suspected of having, or at risk for HAE, thereby treating (e.g., ameliorating or improving a symptom or feature of a disorder, slowing, stabilizing and/or halting disease progression) the disorder.

The antibody described herein can be administered in a therapeutically effective amount. A therapeutically effective amount of an antibody is the amount which is effective, upon single or multiple dose administration to a subject, in treating a subject, e.g., curing, alleviating, relieving or improving at least one symptom of a disorder in a subject to a degree beyond that expected in the absence of such treatment.

Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. In other examples, a bolus may be administered followed by several doses over time or the dose may be proportionally reduced or increased as indicated by the exigencies of the therapeutic situation. In other examples, a dose may be divided into several doses and be administered over time. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Any of the subjects described herein may have undergone prior treatment of HAE, such as a prophylactic or therapeutic treatment of HAE. Aspects of the present disclosure also provide methods of administering an antibody as described herein (e.g., DX-2930) to a subject that has received one or more prior treatment for HAE. In some embodiments, the prior treatment of HAE is a treatment that involves an antibody described herein (e.g., DX-2930). In some embodiments, the subject was previously administered multiple doses of DX-2930 every two weeks or every four weeks. In some embodiments, the subject was previously administered DX-2930 at 150 mg every two weeks. In some embodiments, the subject was previously administered DX-2930 at 300 mg every two weeks. In some embodiments, the subject was previously administered DX-2930 at 300 mg every four weeks. In some embodiments, the multiple doses of the antibody of the prior treatment are administered at least two times, at least three times, at least four times, at least five times, at least six times, at least seven times, at least eight times, at least nine times, at least ten times, at least eleven times, at least twelve time, at least thirteen times.

In some embodiments, the subject has received one or more prior treatment for HAE, which may involve any of the therapeutic agent for HAE known in the art. Exemplary anti-HAE agents include, but are not limited to, C1-inhibitors (e.g., Cinryze®, Berinert®, or Ruconest®), plasma kallikrein inhibitors (e.g., Kalbitor®), bradykinin receptor inhibitors (e.g., Firazyr®), annenuated androgens (e.g., danazol), and anti-fibrinolytics (e.g., traexamic acid). In some examples, a subject may undergo a tapering period before receiving the anti-pKal antibody treatment as described herein. A tapering period refers to a period, prior to the anti-pKal antibody treatment, during which a subject who is on an anti-HAE treatment (e.g., C1-INH, oral androgen, and/or oral anti-fibrinolytics) gradually reduces the dosage, frequency, or both of the anti-HAE agent such that the subject can gradually transit from the prior HAE treatment to the anti-pKal antibody treatment as described herein. In some embodiments, the tapering involving a gradual or step-wise method of reducing the dosage of the prior treatment and/or the frequency with which the prior treatment is administered. The tapering period may last 2-4 weeks and can vary based on factors of an individual patent. In some examples, the prior treatment terminates before the anti-pKal antibody treatment starts. In other examples, the prior treatment may terminate within a suitable timeframe (e.g., 2 weeks, 3 weeks, or 4 weeks) after the subject is given his or her first dose of the anti-pKal antibody.

Alternatively, a subject who is on a prior HAE treatment may be transitioned to the anti-pKal antibody treatment as described herein directly without the tapering period.

In other embodiments, the subject is free of any prior treatment of HAE before the first treatment, first treatment period, and/or the follow-on single and multiple dose treatments as described herein (the second treatment period). In some embodiments, the subject is free of any treatment other than with the antibodies described herein during the first treatment period and/or during the second treatment period. In some embodiments, the subject is free of any prior treatment of HAE for at least two weeks (e.g., at least two, three, four, five weeks or more) before the first treatment or first treatment period, during the first treatment or first treatment period, and/or during the second treatment period. In some embodiments, the subject is free of long-term prophylaxis for HAE (e.g., C1 inhibitor, attenuated androgens, anti-fibrinolytics) for at least the two weeks prior to the first treatment or first treatment period, during the first treatment period, and/or during the second treatment period. In some embodiments, the subject is free of an HAE treatment involving an angiotensin-converting enzyme (ACE) inhibitor for at least the four weeks prior to the first treatment or first treatment period, during the first treatment period, and/or during the second treatment period. In some embodiments, the subject is free of an estrogen-containing medication for at least the four weeks prior to the first treatment or first treatment period, during the first treatment period, and/or during the second treatment period. In some embodiments, the subject is free of androgens (e.g. stanozolol, danazol, oxandrolone, methyltestosterone, testosterone) for at least the two weeks prior to the first treatment or first treatment period, during the first treatment period and/or during the second treatment period.

Any of the methods described herein may further comprise monitoring the patient for side effects (e.g., elevation of creatine phosphatase levels) and/or inhibition levels of pKal by the antibody (e.g., serum or plasma concentration of the antibody or the pKal activity level) before and after the treatment or during the course of treatment. If one or more adverse effect is observed, the dose of the antibody might be reduced or the treatment might be terminated. If the inhibition level is below a minimum therapeutic level, further doses of the antibody might be administered to the patient. Patients may also be evaluated for the generation of antibody against the administered antibody; activity of C1-inhibitor, C4, and/or Clq; quality of life; incidence of any HAE attacks, health-related quality of life, anxiety and/or depression (e.g., Hospital Anxiety and Depression Scale (HADS)), work productivity (e.g., Work Productivity and Activity Impairment Questionnaire (WPAI)), preference of the subcutaneous administration of the antibody (e.g., D-2930) relative to other injectibles, quality of life (e.g, angioedema-quality of life (AE-QOL), EuroQoL Group 5-dimension report).

In some embodiments, the plasma or serum concentration of the antibody (e.g., DX-2930) may be measured during the course of the treatment (e.g., after the initial dosage) for assessing the efficacy of the treatment. If the plasma or serum concentration of the antibody is lower than about 80 nM, a follow-up dosage may be needed, which may be the same or higher than the initial dosage. The plasma or serum concentration of the antibody may be measured by determining the protein level of the antibody in a plasma or serum sample obtained from the subject, e.g., by an immune assay or MS assay. The plasma or serum concentration of the antibody may also be measured by determining the inhibitory level of pKal in a plasma or serum sample obtained from a subject treated with the antibody. Such assays may include the synthetic substrate assay or the Western blot assay for measuring cleaved kininogen as described herein.

Alternatively or in addition, the plasma or serum level of creatine kinase and/or one or more coagulation parameters (e.g., activated partial thromboplastin time (aPTT), prothrombin time (PT), bleeding events) can be monitored during the course of the treatment. If the plasma or serum level of creatine kinase is found to elevate during the treatment, the dosage of the antibody may be reduced or the treatment may be terminated. Similarly, if one or more coagulation parameters are found to be significantly affected during the treatment, the dosage of the antibody may be modified or the treatment may be terminated.

In some embodiments, an optimal dosage (e.g., optimal prophylactic dosage or optimal therapeutic dosage) of the antibody (e.g., DX-2930) may be determined as follows. The antibody is given to a subject in need of the treatment at an initial dose. The plasma concentration of the antibody in the subject is measured. If the plasma concentration is lower than 80 nM, the dose of the antibody is increased in a subsequent administration. A dosage of the antibody that maintains the antibody plasma concentration above about 80 nM can be chosen as the optimal dosage for the subject. The creatine phosphokinase level of the subject can be monitored during the course of treatment and the optimal dosage for that subject can be further adjusted based on the creatine phosphokinase level, e.g., the dosage of the antibody might be reduced is elevation of creatine phosphokinase is observed during treatment.

(iii) Combination Therapies

An antibody as described herein (e.g., DX-2930) can be administered in combination with one or more of the other therapies for treating a disease or condition associated with plasma kallikrein activity, e.g., a disease or condition described herein. For example, an antibody as described herein (e.g., DX-2930) can be used therapeutically or prophylactically (e.g., before, during, or after the course of treatment) with another anti-plasma kallikrein Fab or IgG (e.g., another Fab or IgG described herein), another plasma kallikrein inhibitor, a peptide inhibitor, small molecule inhibitor, or surgery. Examples of plasma kallikrein inhibitors that can be used in combination therapy with a plasma kallikrein binding antibodies described herein include plasma kallikrein inhibitors described in, e.g., WO 95/21601 or WO 2003/103475.

One or more plasma kallikrein inhibitors can be used in combination with an antibody as described herein (e.g., DX-2930). For example, the combination can result in a lower dose of the inhibitor being needed, such that side effects are reduced.

An antibody as described herein (e.g., DX-2930) can be administered in combination with one or more current therapies for treating HAE. For example, DX-2930 antibody can be co-used with a second anti-HAE therapeutic agent such as ecallantide, a C1 esterase inhibitor (e.g., CINRYZE™), aprotinin (TRASYLOL®), and/or a bradykinin B2 receptor inhibitor (e.g., icatibant (FIRAZYR®)).

The term "combination" refers to the use of the two or more agents or therapies to treat the same patient, wherein the use or action of the agents or therapies overlaps in time. The agents or therapies can be administered at the same time (e.g., as a single formulation that is administered to a patient or as two separate formulations administered concurrently) or sequentially in any order. Sequential administrations are administrations that are given at different times. The time between administration of the one agent and another agent can be minutes, hours, days, or weeks. The use of a plasma kallikrein binding antibody described herein can also be used to reduce the dosage of another therapy, e.g., to reduce the side effects associated with another agent that is being administered. Accordingly, a combination can include administering a second agent at a dosage at least 10, 20, 30, or 50% lower than would be used in the absence of the plasma kallikrein binding antibody. In some embodiments, a subject can be given a C1-inhibitor as a loading IV dose or SC dose simultaneously with the first dose of an anti-pKal antibody (e.g., DX-2930) as described herein. The subject can then continue with the anti-pKal antibody treatment (without further doses of the C1-inhibitor).

A combination therapy can include administering an agent that reduces the side effects of other therapies. The agent can be an agent that reduces the side effects of a plasma kallikrein associated disease treatment.

(iv) Assays for Assessing a Treatment Regimen

Also within the scope of the present disclosure are assay methods for assessing efficacy of any of the treatment methods described herein. In some embodiments, the plasma or serum concentration of one or more biomarkers (e.g., 2-chain HMWK) associated with HAE may be may be measured prior to and/or during the course of the treatment (e.g., after the initial dosage) for assessing the efficacy of the treatment. In some embodiments, the plasma or serum concentration (level) of one or more biomarkers associated with HAE obtained at a time point after administration of a dosage is compared to the concentration of the biomarker in a sample obtained at an earlier time point after administration of a dosage or prior to administration of the initial dosage. In some embodiments, the biomarker is 2-HMWK.

The level of the biomarker may be measured by detecting the biomarker in a plasma or serum sample obtained from the subject, e.g., by an immunoassay, such as Western blot assay or ELISA, using an antibody that specifically detects the biomarker. In some embodiments, the level of 2-HWMK in a plasma or serum sample obtained from the subject is assessed by an immunoassay. Antibodies for use in immunoassays for the detection of 2-HWMK are known in the art and selection of such an antibody for use in the methods described herein will be evident to one of ordinary skill in the art.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Indirect Treatment Comparison of DX-2930 and Intravenous C1 Esterase Inhibitor Treatments for Long-term Prophylaxis of Hereditary Angioedema Attacks Study Overview A systematic literature review was undertaken to identify and summarize the existing evidence for efficacy and safety of long-term prophylactic treatment of patients with type I and type II hereditary angioedema (HAE) for an indirect treatment comparison (ITC). Additionally, data from the HELP study (Banerji et al., *JAMA* 320 (20): 2108-21, 2018) were analyzed to establish the optimal parametric survival models for use in an ITC with the evidence identified by the systematic literature review. All analyses were conducted using R (R Core Team, 2018, www.R-project.org).

The HELP study assessed the efficacy and safety of subcutaneous lanadelumab (DX-2930) in preventing acute angioedema attacks in patients with type I and type II HAE in which three lanadelumab dosing regimens (300 mg every two weeks [q2w], 300 mg every four weeks [q4w], and 150 mg q4w) were investigated and compared with placebo (Banerji et al., *JAMA* 320 (20): 2108-21, 2018).

Materials and Methods

A systematic literature search through June 2017 was conducted using MEDLINE, Embase, MEDLINE In-Process, and the Cochrane Library database. A search of conference proceedings was conducted for the years 2016 and 2017 and included EAACI; American College of Allergy, Asthma and Immunology; World Allergy Congress; and European Society for Immunodeficiency. An additional search of key health technology assessment agencies included the National Institute for Health and Care Excellence (NICE), Canadian Agency for Drugs and Technologies in Health Common Drug Review, Scottish Medicines Consortium, and All Wales Medicines Strategy Group. The search focused on studies for long-term prophylaxis of angioedema attacks in patients with type I or type II HAE who were ≥12 years of age based on the criteria described in Table 1B.

TABLE 1B

Key Inclusion and Exclusion Criteria for Literature Search

| Category | Inclusion Criteria | Exclusion Criteria |
|---|---|---|
| Population | Patient with type I and type II HAE<br>Any race<br>Age ≥12 years | Healthy volunteers<br>Pediatric population (age <12 years)<br>Type III HAE<br>Disease other than HAE |
| Interventions | Prophylactic treatments (short- or long-term; mono- and/or combination therapy):<br>Berinert ®<br>Cinryze ® (formerly Cetor)<br>Lanadelumab (DX-2930)<br>Danazol<br>Stanozolol<br>Oxandrolone<br>Methyl testosterone<br>Testosterone | Nonpharmacologic treatments<br>Fresh frozen plasma, solvent detergent plasma, antifibrinolytic agents<br>Acute treatments<br>Icatibant (Firazyr ®), ecallantide (Kalbitor ®), recombinant C1 esterase inhibitor (Ruconest ®)<br>Surgery<br>Studies assessing interventions not in the list |
| Comparators | No restrictions | |
| Outcomes | No restrictions | |
| Study design | RCTs irrespective of blinding status<br>Non-RCTs<br>Observational studies<br>Single-arm studies<br>Cohort studies (prospective and retrospective)<br>Long-term follow-up studies<br>Systematic reviews and meta-analyses of RCTs/non-RCTs[a] | Case reports, case series<br>Pharmacokinetic and economic studies<br>Preclinical studies<br>Reviews, letters, and comment articles |
| Language | No restrictions[b] | |

HAE, hereditary angioedema; RCT, randomized controlled trial.

[a]Systematic reviews and meta-analyses of RCTs and non-RCTs were included and flagged for bibliography screening to determine if literature searches missed any potentially relevant studies.

[b]Non-English language publications were included and explored if no sufficient evidence was identified from publications written in English.

The development and reporting of this analysis followed Preferred Reporting Items for Systematic Reviews and Meta-Analyses (PRISMA) guidelines (Moher et al., *PLoS Med.* 6 (7): e1000097, 2009). Randomized controlled trials were considered the highest standard of evidence for ITC, and data from nonrandomized studies were also considered if no randomized controlled trial data were available.

Abstracts and full-text articles were evaluated for inclusion by two independent reviewers, and data extraction from the selected literature was performed by one reviewer and independently validated by a second reviewer; any uncertainties were resolved by a third reviewer. A descriptive assessment of the included randomized controlled trials was performed by two independent reviewers using comprehensive assessment criteria based on the recommendations in the NICE manufacturer's submission template (Single technology appraisal (STA): user guide for company evidence submission template. UK: National Institute for Health and Care Excellence;www.nice.org.uk/process/pmg24/chapter/instructions-for-companies #quality-assessment-of-the-relevant-randomised-controlled-trials, 2015).

Parametric Survival Models

Kaplan-Meier curves were derived for the time to first HAE attack (defined as all investigator-confirmed attacks) after day 0 and day 70 for each lanadelumab dosing regimen and placebo using patient-level data from the HELP study (Banerji et al., *JAMA* 320 (20): 2108-21, 2018). A univariate Cox proportional hazards model with treatment as the only covariate was fit to estimate the relative treatment effect (i.e., HR) for each lanadelumab dose compared with placebo.

To extrapolate long-term survival curves to be used in the NMA, standard parametric survival models (Exponential, Weibull, log-normal, log-logistic, Gompertz, and generalized gamma survival models) (Latimer, Decision Support Unit, National Institute for Health and Clinical Excellence; nicedsu.org.uk/wp-content/uploads/2016/03/NICE-DSU-TSD-Survival-analysis.updated-March-2013.v2.pdf, 2011) were fit to the Kaplan-Meier data. If the standard models did not fit to the observed data, a more flexible proportional hazards spline model was considered, which is an extension of the standard Weibull model that models the log cumulative hazard as a natural cubic spline function of log time (Royston et al., *Stat Med.* 21 (15): 2175-97, 2002). Methods employed to assess the fit of the model were clinical plausibility of extrapolations, goodness-of-fit measures, and visual inspection by overlaying fitted survival curves with observed survival data.

Attack Rate and Time to First HAE Attack

Outcomes of interest for this ITC were event (HAE attack) rate and time to event (first HAE attack). Attack rate was defined as the number of attacks experienced in a 28-day cycle, with relative treatment effects estimated as rate ratios (RRs). Time to first attack was defined as the time a patient with HAE had their first attack after day 0 (date of first administered dose of prophylactic therapy) or day 70 (approximate day at which steady state plasma lanadelumab concentration is reached). For time to first attack, relative treatment effects were estimated as hazard ratios (HRs).

A Bayesian NMA, relying on Markov chain Monte Carlo methods, was developed to evaluate the outcomes of attack rate and time to first attack. Relative efficacy was estimated using a treatment effect model to allow synthesis of direct and indirect evidence in one analysis while accounting for correlation arising from multi-arm trials (Dias et al., Decision Support Unit, National Institute for Health and Clinical Excellence; nicedsu.org.uk/wp-content/uploads/2017/05/TSD2-General-meta-analysis-corrected-2sep.2016v2.pdf, 2011). Some studies in the evidence network did not report time to first attack. However, because the proportion of patients who had not experienced an HAE attack was reported for every study, an extension of the NMA method was used to synthesize the count data and time-to-event data in the same analysis (Woods et al., *BMC Med* Res Methodol. 10:54, 2010). Treatment effects were compared using credible intervals (CrIs); for cases in which the CrI for treatment versus placebo did not include the value 1, the results were considered statistically significant. Both HELP and CHANGE were randomized, double-blind trials in patients with confirmed HAE (Banerji et al., *JAMA.* 320 (20): 2108-21, 2018; Zuraw et al., *N Engl J Med.* 363 (6): 513-22, 2010). Fixed- and random-effects models were considered for the NMA, and the choice of model was based on an assessment of study design, inclusion criteria, and patient characteristics.

Predicted Survival Curves

Predicted survival curves were derived for each treatment arm separately for time to first attack after day 0 and day 70 by combining the HRs from the ITC and the spline survival curve fitted to the placebo data from the HELP study. These curves were used to estimate the proportion of attack-free patients and 95% confidence intervals (CIs) at 60 months after the start of prophylactic treatment (day 0 or day 70) for each comparator in the ITC.

Results

Systematic Literature Review

A systematic literature review was undertaken. A summary of the records identified is presented in FIG. 1. The search identified 1299 records, of which 52 (22 records from seven randomized controlled trials [RCTs] and 30 records from 23 nonrandomized controlled trials [nRCTs]) met the eligibility criteria and were selected for detailed feasibility assessment for possible inclusion in the ITC with lanadelumab results from the HELP study. Twenty-two records were excluded because they were secondary publications for which a primary publication had already been identified among the 52 records that met the eligibility criteria. Of the remaining records in the feasibility assessment, 20 lacked real-world applicability and were therefore excluded as inappropriate comparators. Included in these were two RCTs (Gelfand et al., *N Engl J Med.* 295 (26): 1444-8, 1976; Sheffer et al., *Ann Int Med.* 86 (3): 306-8, 1977) and 15 nRCTs (Füst et al., *Eur J Clin Invest.* 41 (3): 256-62, 2011; Agostoni et al., Medicine (Baltimore).71 (4): 206-15, 1992; Bork et al., *Ann Allergy Asthma Immunol.* 100 (2): 153-61, 2008; Caminoa et al., Allergy. 68 (suppl 97): 61, 2013; Cicardi et al., *J Allergy Clin Immunol.* 99 (2): 194-6, 1997; Davis et al., *Johns Hopkins Med J.* 135 (6): 391-8, 1974; Farkas et al., *J Oral Maxillofac Surg.* 57 (4): 404-8, 1999; Kreuz et al., Transfusion.49 (9): 1987-95, 2009; Obtulowicz et al., *Int Rev Allergol Clin Immunol.* 3 (3): 163-6, 1997; Ott et al., *Clin Endocrinol* (Oxf). 66 (2): 180-4, 2007; Psarros et al., *Int Arch Allergy Immunol.* 164 (4): 326-32, 2014; Rosen et al., *Birth Defects: Orig Artic Ser.* 16 (1): 499-507; 1980; Steiner et al., *Orphanet J Rare Dis.* 11:43; 2016; Winnewisser et al., *J Int Med.* 241 (1): 39-46, 1997; Zotter et al., *Orphanet J Rare Dis.* 9:205, 2014) describing the use of attenuated androgens and one RCT (Riedl et al., *Allergy Asthma Proc.* 37 (6): 489-500, 2016) describing the use of a combination therapy of SC C1-INH/recombinant human hyaluronidase in patients with HAE, since these interventions are not recommended by the WAO/EAACI guidelines for HAE management as long-term prophylaxis (Maurer et al., *Allergy.* 73 (8): 1575-96, 2018); two RCTs (Longhurst et al., *N Engl J Med.* 376 (12): 1131-40, 2017; Zuraw et al., *Allergy.* 70 (10): 1319-28, 2015) describing the use of SC C1-INH were excluded because this product is not commercially available outside the United States and Canada (CSL Behring. Global product list; www.cslbehring.com/products/global-products-list; retrieved 2019 Feb. 20), limiting the real-world applicability of any comparison.

Figure 2:
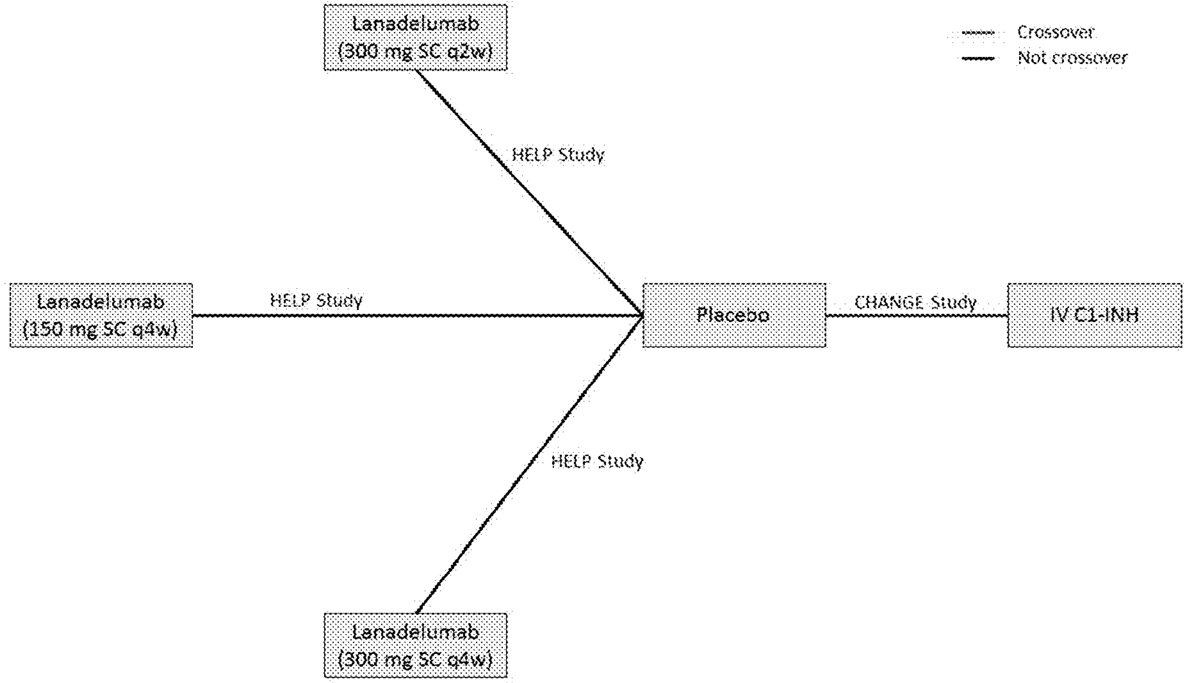
FIG. 2 is a final network diagram for an indirect treatment comparison of lanadelumab (HELP Study; Banerji et al., *JAMA.* 320 (20): 2108-21, 2018) and IV C1-INH (CHANGE Study; Zuraw et al., *N Engl J Med.* 363 (6): 513-22, 2010). The CHANGE study is a crossover study. C1-INH, C1 esterase inhibitor; IV, intravenous; q2w, every two weeks; q4w, every four weeks; SC, subcutaneous.

One record reported results from a phase 3 study of an IV C1-INH (Zuraw et al., *N Engl J Med.* 363 (6): 513-22, 2010) and was deemed appropriate for ITC with lanadelumab results from the HELP study. Because this RCT was appropriate for ITC, and because nRCTs were only considered if no RCTs for a given intervention could be identified, the four nRCTs for this intervention (Bernstein et al., *J Allergy Clin Immunol* Pract. 2 (1): 77-84 2014; Aygören-Pürsün et al., *J Allergy Clin Immunol.* 137 (2): AB251, 2016; Rasmussen et al., *Ann Allergy Asthma Immunol.* 116 (5): 476-7, 2016; Zuraw et al., *Am J Med.* 125 (9): 938.e1-. e7, 2012) were subsequently excluded. The remaining five studies (Banerji et al., *N Engl J Med.* 376 (8): 717-28, 2017; Bork et al., *Oral Surg Oral Med Oral Pathol Oral Radiol Endod.* 112 (1): 58-64, 2011; Bouillet et al., *Allergy.* 72 (Suppl 103): 593, 2017; Farkas et al., *Allergy.* 67 (12): 1586-93, 2012; Levi et al., *J Allergy Clin Immunol.* 117 (4): 904-8, 2006) were excluded because of differences and/or lack of clarity in study design, study population, intervention, endpoints, and/or patient characteristics (Table 2). The network diagram for the two studies included in the ITC is shown in FIG. 2. The design for each study is summarized in Table 3, and baseline demographic characteristics and results for primary outcomes for both studies are presented in Table 4.

TABLE 2

Summary of Feasibility Assessment of Select Records Identified by Systematic Literature Review for Potential Inclusion in the Indirect Treatment Comparison[a]

| Study | Study Design | Patients, n | Treatment, Dose, Regimen | Key Criteria for Inclusion/Exclusion From Indirect Treatment Comparison |
|---|---|---|---|---|
| Banerji 2017 [64] | Randomized, double-blind, placebo-controlled clinical trial | 11 | Lanadelumab 400 mg q2w SC | Excluded based on study design and endpoints: |
| | | 5 | Lanadelumab 300 mg q2w SC | Phase 2 dose-escalation study Outcomes focused on PK/PD |
| | | 4 | Lanadelumab 100 mg q2w SC | Attack rate measured as adverse event up to 120 days after final dose |
| | | 4 | Lanadelumab 30 mg q2w SC | |
| | | 13 | Placebo | |

TABLE 2-continued

Summary of Feasibility Assessment of Select Records Identified by Systematic Literature Review for Potential Inclusion in the Indirect Treatment Comparison[a]

| Study | Study Design | Patients, n | Treatment, Dose, Regimen | Key Criteria for Inclusion/Exclusion From Indirect Treatment Comparison |
|---|---|---|---|---|
| Levi 2006 [68] | Nonrandomized clinical trial | 43 | IV C1-INH (Cetor ® 1000 units every 5-7 days) | Excluded based on intervention and lack of endpoint data: Attack rate is reported only graphically, no values are available |
| Bork 2011 [65] | Retrospective, observational study | 33 | IV C1-INH (Berinert ® 500 U; single dose) | Excluded based on study population: Investigated as short-term |
| | | 18 | IV C1-INH (Berinert ® 1000 U; single dose) | prophylaxis for prevention of an attack following a surgical procedure |
| Bouillet 2017 [66] | Retrospective, observational study | 132 | IV C1-INH (Berinert ®)[b] | Excluded based on study population: Used only as an acute treatment after an attack |
| Farkas 2012 [67] | Retrospective, observational study | 87 | IV C1-INH (Berinert ® 500 U; single dose) | Excluded based on study population: |
| | | 38 | Danazol (oral; 2.5-10 mg/kg per day for 5 days) | Investigated as short-term prophylaxis for prevention of an attack following a dental, |
| | | 9 | Tranexamic acid (oral; 20-40 mg/kg per day for 5 days) | diagnostic, or surgical procedure |

C1-INH, C1 esterase inhibitor;
IV, intravenous;
PD, pharmacodynamics;
PK, pharmacokinetics;
q2w, every 2 weeks;
SC, subcutaneous.
[a]Does not include assessment of the feasibility of records that were included in the ITC (n = 1) or excluded as secondary publications (n = 22), inappropriate comparators (n = 20), or unnecessary nRCTs (n = 4).
[b]Detailed dosing information was not reported.

TABLE 3

Trial Design of the HELP and CHANGE Studies Used for Indirect Treatment Comparison

| Characteristic | HELP Study[b] | CHANGE Study[a] |
|---|---|---|
| Study design | Double-blind, placebo-controlled | Double-blind, placebo-controlled |
| Trial type | Parallel | Crossover[a] |
| Disease state inclusion criteria | Confirmed HAE diagnosis<br>C1-INH functional level <40% or 40%-50% if C4 level below normal range<br>≥1 of the following:<br>Age ≤30 years at reported onset of first angioedema symptoms<br>Family history consistent with HAE types I or II<br>C1q level within normal range<br>Experience baseline rate of ≥1 investigator-confirmed HAE attack per four weeks during run-in period | Confirmed HAE diagnosis<br>Low antigenic or functional C1-INH level or known HAE-causing mutation in C1-INH gene<br>Low C4 level<br>Normal C1q level<br>≥2 attacks per month (for prophylaxis study) |
| Primary endpoint | Number of investigator-confirmed attacks (day 0-182) | Number of attacks during each treatment period (normalized to number of days participated) |
| Administration | Subcutaneous | Intravenous |
| Washout period | ≥2 weeks | None |
| Treatment period | 26 weeks | 12 weeks[a] |

C1-INH, C1 esterase inhibitor; HAE, hereditary angioedema.
[a]The CHANGE study included two parts: part A, which evaluated IV C1-INH use in acute attacks, and part B, which evaluated its use in prophylaxis. Only part B is summarized here and was a crossover study that consisted of two 12-week treatment periods in which patients were randomly assigned to receive either IV C1-INH or placebo during the first treatment period and then crossed over, in a second treatment period, to the treatment that was not received during the first treatment period (Zuraw et al., N Engl J Med. 363(6):513 22, 2010).
[b]Banerji et al., JAMA 320(20):2108-21, 2018

TABLE 4

Demographic Characteristics and Primary Outcomes From the HELP and CHANGE Studies Used for Indirect Treatment Comparison

| Characteristic | HELP Study[b] Lanadelumab 300 mg q2w (n = 27) | Lanadelumab 300 mg q4w (n = 29) | Lanadelumab 150 mg q4w (n = 28) | Placebo (n = 41) | CHANGE Study[a] IV C1-INH (n = 11) | Placebo (n = 11) |
|---|---|---|---|---|---|---|
| Mean (SD) age, y | 40.3 (13.3) | 39.5 (12.8) | 43.4 (14.9) | 40.1 (16.8) | 41.7 (19.3) | 34.5 (14.8) |
| Female patients, n (%) | 15 (55.6) | 19 (65.5) | 20 (71.4) | 34 (82.9) | 9 (81.8) | 11 (100) |
| Type II HAE, n (%) | 4 (14.8) | 2 (6.9) | 3 (10.7) | 3 (7.3) | 2 (18.2) | 2 (18.2) |
| Patients with ≥ 2 attacks/month prior to study entry, n (%) | 20 (74.1) | 20 (69.0) | 18 (64.3) | 29 (70.7) | 11 (100) | 11 (100) |
| Primary endpoint | | | | | | |
| Rate of investigator-confirmed HAE attacks per 4 wk (day 0-182), LS mean (95% CI) | 0.26 (0.15, 0.46) | 0.53 (0.36, 0.77) | 0.48 (0.31, 0.74) | 1.97 (1.64, 2.36) | NA | NA |
| Change vs placebo, % (95% CI) | −86.9 (−92.8, −76.2)* | −73.3 (−82.4, −59.5)* | −75.6 (−84.7, −61.2)* | NA | NA | NA |
| Rate of investigator-confirmed HAE attacks per 4 wk (day 70-182), LS mean (95% CI) | 0.16 (0.07, 0.35) | 0.37 (0.22, 0.60) | 0.42 (0.26, 0.68) | 1.88 (1.54, 2.30) | NA | NA |
| Change vs placebo, % (95% CI) | −91.5 (−96.1, −81.1)* | −80.6 (−88.5, −67.3)* | −77.6 (−86.7, −62.3)* | NA | NA | NA |
| HAE attack rate per 12 wk, mean[a] | NA | NA | NA | NA | 6.26 | 12.73 |
| Change vs placebo, mean (95% CI) | NA | NA | NA | NA | −6.47 (−4.21, −8.73)* | NA |

C1-INH, C1 esterase inhibitor; CI, confidence interval; HAE, hereditary angioedema; IV, intravenous; LS, least squares; NA, not applicable; q2w, every two weeks; q4w, every four weeks; SD, standard deviation.
[a]An attack was defined as a discrete episode during which the subject progressed from no angioedema to symptoms of angioedema; attacks that progressed from one site to another, or that began to regress and then became worse before complete resolution, were considered to be a single attack (Zuraw et al., *N Engl J Med.* 363(6):513-22, 2010).
[b]Banerji et al., *JAMA* 320(20):2108-21, 2018
*P < 0.001 vs placebo.

Time to First Attack (HELP Study)

As demonstrated in the HELP study, time to first HAE attack was increased relative to placebo after each time point for all three lanadelumab dosing regimens, corresponding to reduced risks of experiencing a first attack after day 0 and day 70 from the start of treatment. After day 0, the median number of days to first attack was 59 (95% CI: 28—not estimable [NE]) for patients receiving lanadelumab 300 mg q2w; 28 (95% CI: 10-101) for lanadelumab 300 mg q4w; and 26 (95% CI: 11-NE) for lanadelumab 150 mg q4w, compared with 8 (95% CI: 6-18) for patients receiving placebo. After day 70, more than 50% of patients receiving lanadelumab 300 mg q2w and 150 mg q4w had no attacks through the end of the 6-month treatment period; thus, the median number of days to first attack was NE. The median time to first attack after day 70 in patients receiving lanadelumab 300 mg q4w was 61 days (95% CI: 25-NE) compared with 12 days (95% CI: 6-16) for patients receiving placebo.

As observed in the HELP study, 2.4% of patients receiving placebo were attack-free from day 0 to the end of the treatment period compared with 44%, 31%, and 39% of patients receiving lanadelumab 300 mg q2w, 300 mg q4w, and lanadelumab 150 mg q4w, respectively (Table 5). Similar or greater percentages of attack-free patients were observed with lanadelumab treatment from day 70 to the end of the treatment period. Proportions of attack-free lanadelumab-treated patients were also derived from the Kaplan-Meier estimates of time to first attack after treatment to confirm the validity of the Kaplan-Meier survival analysis. These estimated percentages of attack-free patients were generally consistent with the observed results from each day 0 and day 70 to the end of the 6-month treatment period (Table 5).

TABLE 5

Observed and Estimated Percentages of Attack-Free Patients in the HELP Study After Day 0 and Day 70 to End of Treatment

| Attack-free patients, n (%) | Lanadelumab 300 mg q2w (n = 27) | Lanadelumab 300 mg q4w (n = 29) | Lanadelumab 150 mg q4w (n = 28) | Placebo (n = 41) |
|---|---|---|---|---|
| After Day 0 to End of Treatment | | | | |
| Observed, n (%) | 12 (44.4) | 9 (31.0) | 11 (39.3) | 1 (2.4) |
| Estimated, n (% [95% CI])[a] | 27 (44.4 [29.2, 67.8]) | 29 (31.0 (18.0, 53.4]) | 28 (39.3 [24.8, 62.3]) | 41 (2.4 [0.4, 16.9]) |

TABLE 5-continued

Observed and Estimated Percentages of Attack-Free Patients in the HELP Study After Day 0 and Day 70 to End of Treatment

| Attack-free patients, n (%) | Lanadelumab 300 mg q2w (n = 27) | Lanadelumab 300 mg q4w (n = 29) | Lanadelumab 150 mg q4w (n = 28) | Placebo (n = 41) |
|---|---|---|---|---|
| After Day 70 to End of Treatment | | | | |
| Observed, n (%)[b] | 20 (76.9) | 13 (44.8) | 15 (53.6) | 1 (2.7) |
| Estimated, n (% [95% CI])[a,b] | 26 (76.9 [62.3, 94.9]) | 29 (43.0 [28.0, 65.8]) | 28 (53.6 [37.9, 75.6]) | 37 (2.7 [0.4, 18.7]) |

CI, confidence interval;
q2w, every two weeks;
q4w, every four weeks.
[a]Kaplan-Meier estimates of time to first attack after treatment were used to derive the proportions of patients who remained attack-free.
[b]Does not include patients who discontinued prior to day 70: lanadelumab 300 mg q2w, n = 26; lanadelumab 300 mg q4w, n = 29; lanadelumab 150 mg q4w, n =2 8; placebo, n = 37.

Model Selection for Time to First Attack Endpoints

Various parametric survival models were applied to data for time to first attack after days 0 and 70. Of the six standard parametric models, the Akaike information criterion (AIC) values indicated that the Gompertz model fit the Kaplan-Meier data best for the duration of the study (i.e., after day 0 and day 70). The Gompertz model predicted that patients who were attack-free from day 0 through the end of the study would remain attack-free indefinitely after the study ended. Conservatively based on the possibility of pharmacological drug tolerance and loss of response in which treatment effectiveness may lessen with prolonged exposure (Roda et al., *Clin Transl Gastroenterol.* 7: e135, 2016; Salvà Lacombe et al., *Drugs.* 51 (4): 552-70, 1996), however, the Gompertz model was considered clinically implausible.

Thus, because none of the standard distributions for parametric survival analysis fit the observed data well, the more flexible parametric model of a proportional hazards spline was fit to the data. A spline model with one internal knot (k=1) was found to fit the data best, and this was confirmed based on visual comparison with the Kaplan-Meier data and clinical plausibility of a reduction over time in the relative effect of each lanadelumab dose versus placebo. The addition of further internal knots (k=2-5) to the spline model did not lead to corresponding improvement in model fit.

Indirect Treatment Comparison Via Network Meta-Analysis

A fixed-effects model was chosen for the NMA because no systematic differences were identified between the patient populations in the HELP study and CHANGE trial; both patient populations were similar in age, sex, and percentage of patients with type I or type II HAE (Tables 3 and 4, above). It was therefore assumed that each trial was estimating the same treatment effect and any variation between studies was due only to sampling variation.

Attack Rate

Figure 3:
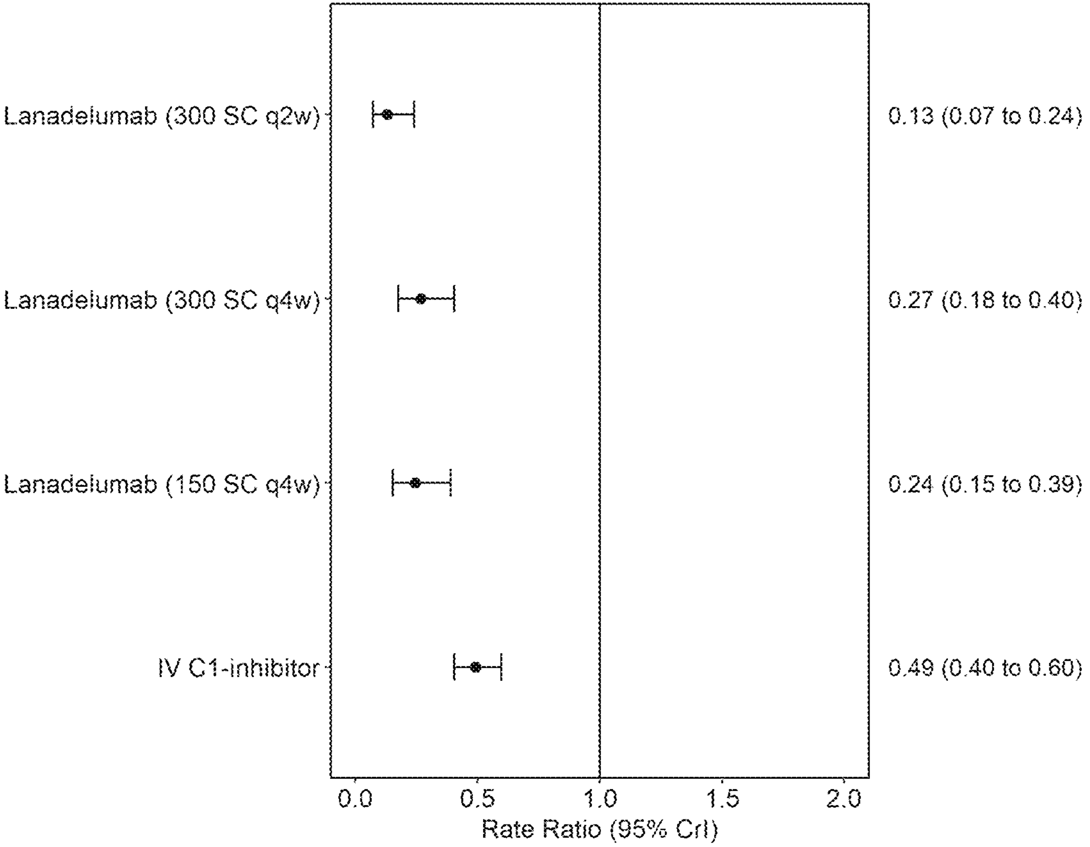
FIG. 3 includes attack rate ratios (95% credible interval, CrI) for all treatments compared to placebo. The rate ratios for lanadelumab vs. placebo were derived from HELP study data and are based on 26 weeks of treatment. The rate ratios for IV C1-INH vs. placebo are derived from CHANGE study data and are based on 12 weeks of treatment. C1-INH, C1 esterase inhibitor; CrI, credible interval; IV, intravenous; q2w, every two weeks; q4w, every four weeks; SC, subcutaneous.

RRs showed a significant reduction in attack rate for patients who received lanadelumab (all dosing regimens) or IV C1-INH compared with placebo (FIG. 3). Reductions in attack rate (per 4-week cycle) were 87%, 73%, and 76% for the lanadelumab 300 mg q2w, 300 mg q4w, and 150 mg q4w treatment arms, respectively (corresponding to respective median RRs [95% CrI] of 0.13 [0.07-0.24], 0.27 [0.18-0.40], and 0.24 [0.15-0.39]) and 51% for IV C1-INH (corresponding to median RR [95% CrI] of 0.49 [0.40-0.60]) compared with placebo.

Time to First Attack

Figure 4A:
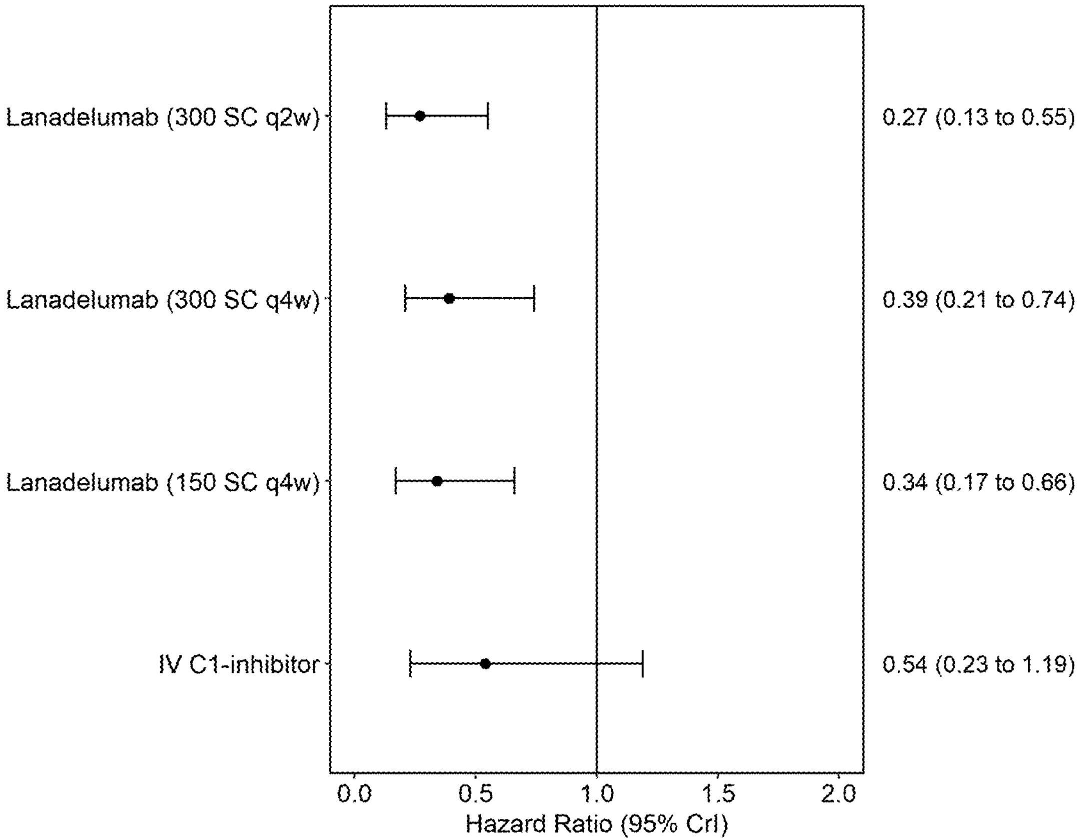
FIGS. 4A-4B include time to first attack hazard ratios (95% credible interval, CrI) for all treatments compared to placebo after day 0 (FIG. 4A) and after day 70 (FIG. 4B). The data for the IV C1-INH are from the CHANGE trial. C1-INH, C1 esterase inhibitor; CrI, credible interval; IV, intravenous; q2w, every two weeks; q4w, every four weeks; SC, subcutaneous.
Figure 4B:
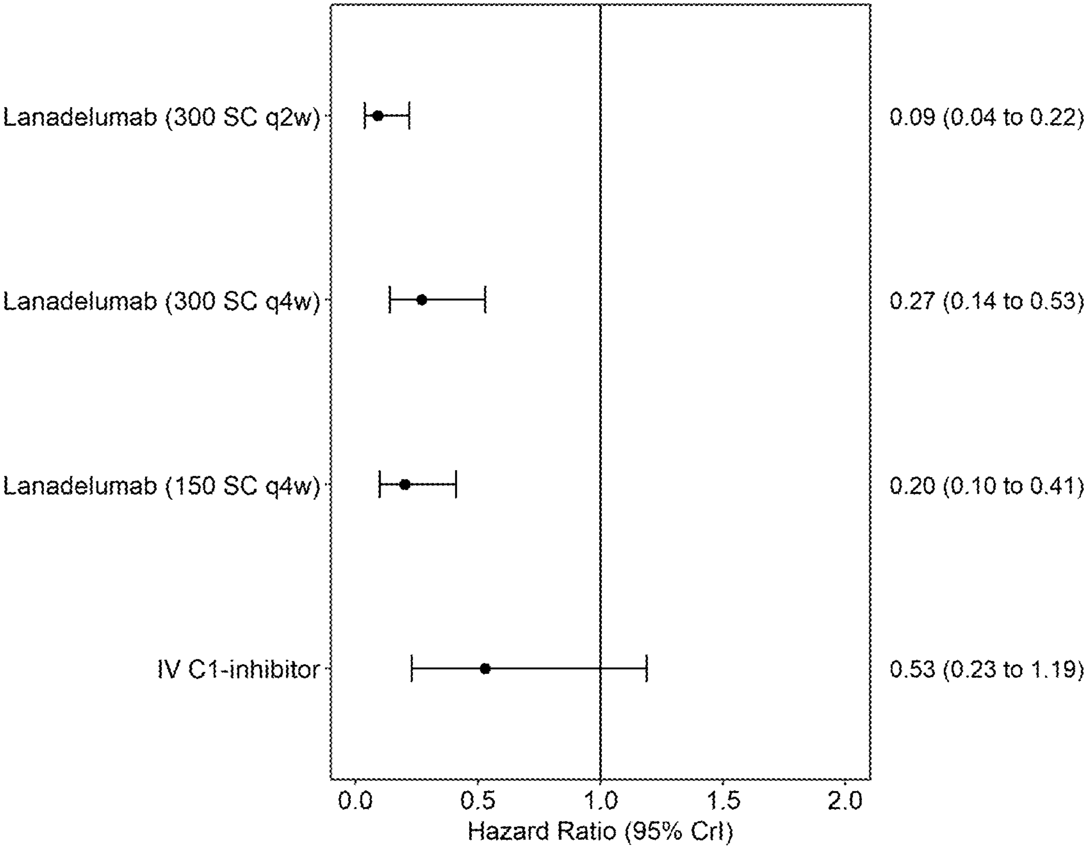

When comparing treatments with placebo, a significantly lower risk of first attack after day 0 was observed for all lanadelumab dosing regimens (median HR [95% CrI]: 300 mg q2w, 0.27 [0.13-0.55]; 300 mg q4w, 0.39 [0.21-0.74]; 150 mg q4w, 0.34 [0.17-0.66]), corresponding to a 61%-73% reduction in risk of first attacks after day 0 (FIG. 4A). Results were similar for risk of first attacks after day 70 (median HR [95% CrI]: 300 mg q2w, 0.09 [0.04-0.22]; 300 mg q4w, 0.27 [0.14-0.53]; 150 mg q4w, 0.20 [0.10-0.41]), with corresponding reductions of 73%-91% (FIG. 4B). In contrast, although a reduction in the risk of first attack was observed with IV C1-INH treatment compared with placebo, these reductions were not statistically significant (median HR [95% CrI]: day 0, 0.54 [0.23-1.19]; day 70, 0.53 [0.23-1.19]).

Predicted Survival Curves for 60-Month Duration

Figure 5A:
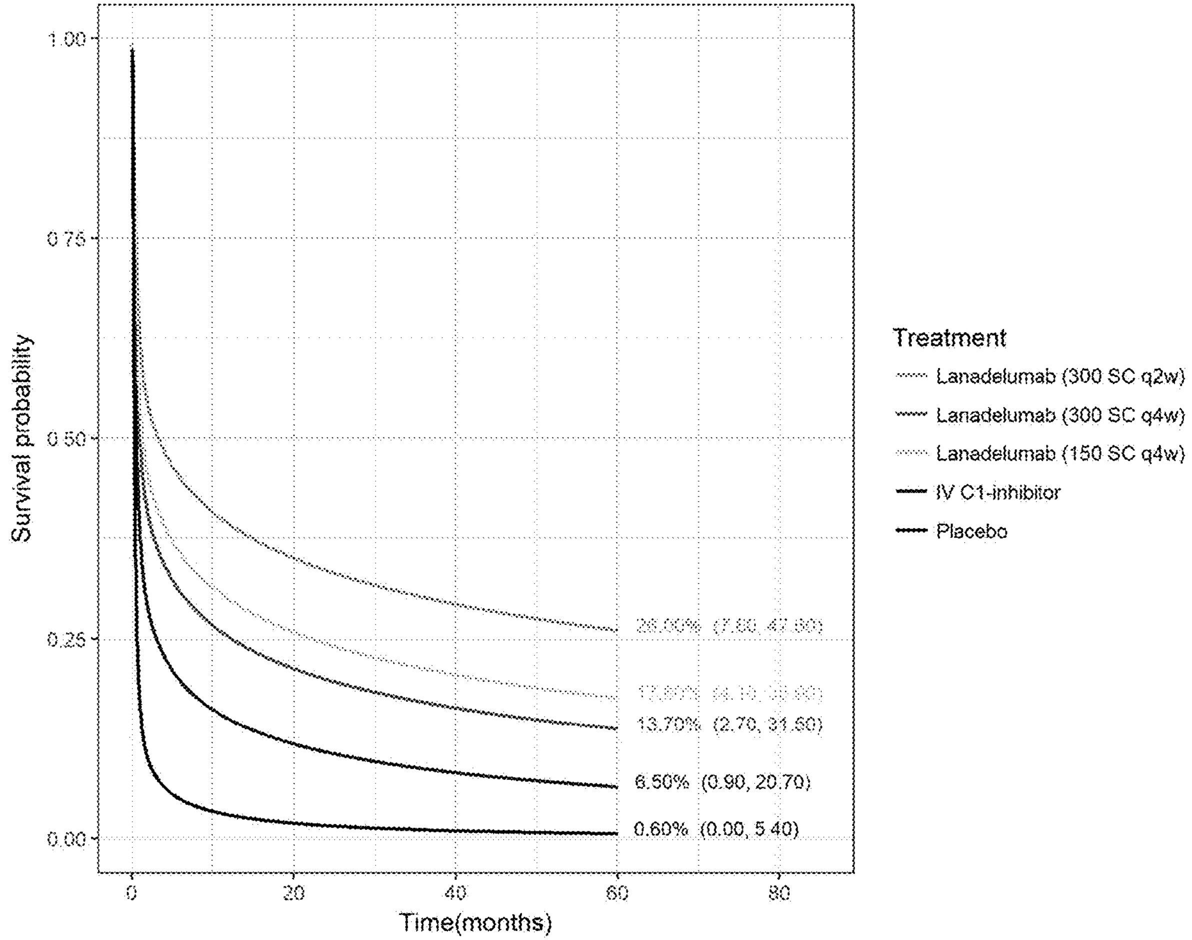
FIGS. 5A-5B include predicted survival curves for time to first attack after day 0 (FIG. 5A) and after day 70 (FIG. 5B). The data are labeled with predicted median (95% confidence interval) percentage of patients who were attack-free at 60 months. The data for the IV C1-INH are from the CHANGE trial. The data in FIG. 5A are as follows: lanadelumab (300 SC q2w), 26.00%, lanadelumab (300 SC q4w), 13.70%, lanadelumab (150 SC q4w), 17.60%, IV C1-inhibitor, 6.50%, and placebo, 0.60%. The data in FIG. 5B are as follows: lanadelumab (300 SC q2w), 46.20%, lanadelumab (300 SC q4w), 9.30%, lanadelumab (150 SC q4w), 16.50%, IV C1-inhibitor, 0.90%, and placebo, 0.00%. C1-INH, C1 esterase inhibitor; IV, intravenous; q2w, every two weeks; q4w, every four weeks; SC, subcutaneous.
Figure 5B:
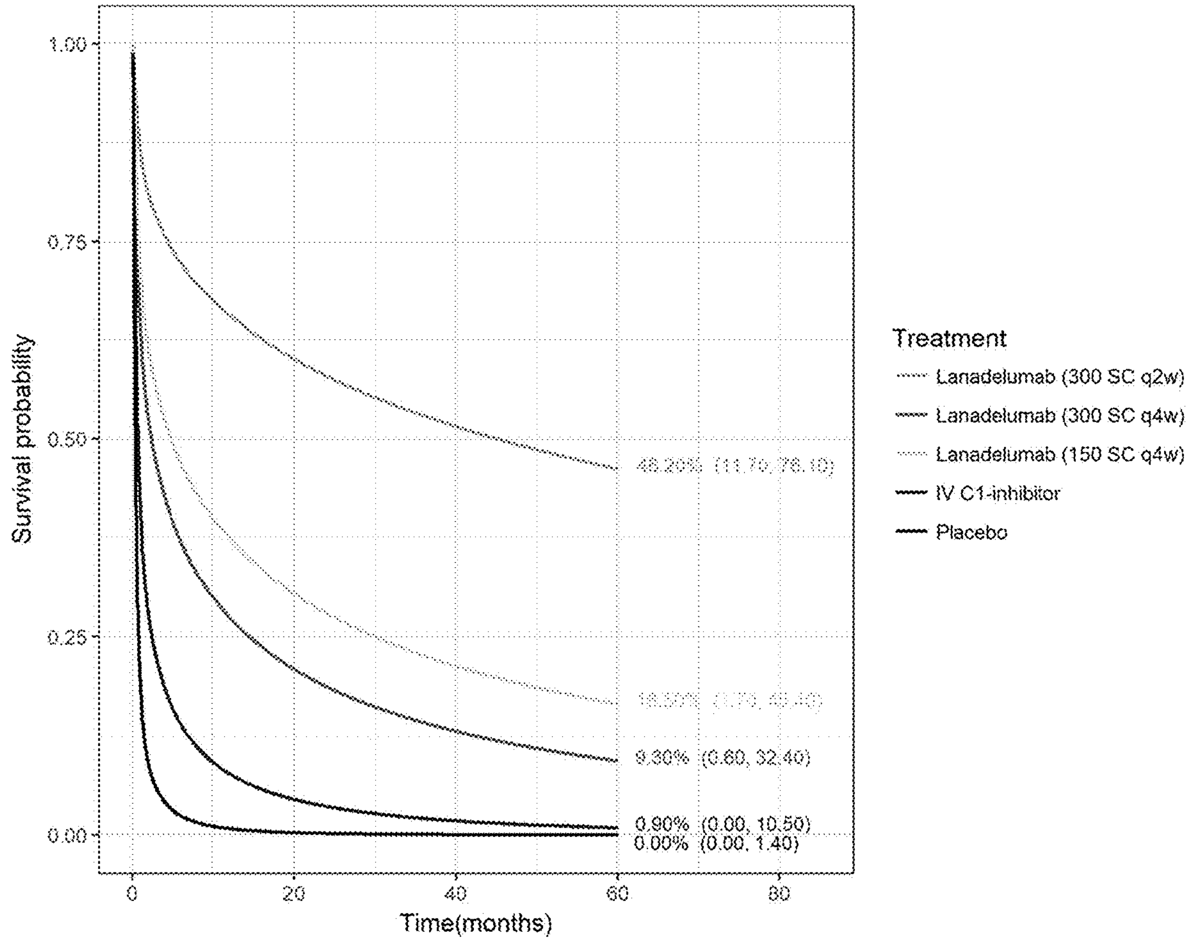

Predicted survival curves for 60-month duration based on time to first attack were derived for each treatment after day 0 and day 70 (FIGS. 5A-5B) by combining the HRs from the ITC and the spline survival curve fit to the HELP study placebo data. The highest predicted proportions of attack-free patients were observed with lanadelumab 300 mg q2w over both time points. When data for time to first attack after day 0 were extrapolated out to 60 months, the predicted percentages of attack-free patients were 26%, 6.5%, and 0.6% for treatment with lanadelumab 300 mg q2w, IV C1-INH, and placebo, respectively. When time to first attack data were extrapolated out to 60 months, the predicted percentages of attack-free patients were 46%, 0.9%, and 0% after day 70 for lanadelumab 300 mg q2w, IV C1-INH, and placebo, respectively.

A proportional hazards spline model with one internal knot (k=1) was found to best fit observed time to first attack data from the HELP study. These data demonstrated that a key benefit for receiving lanadelumab compared with placebo for prophylaxis of HAE attacks was the increase in duration of attack-free period. The highest predicted proportions of attack-free patients were observed with lanadelumab 300 mg q2w over all time points, whereas the lowest predicted proportions of patients who were attack-free were observed with IV C1-INH and placebo. Based on the approximately 14-day half-life of lanadelumab (range, 13.8-15.0 days), time to steady-state concentrations of lanadelumab has been estimated to be approximately 70 days. Thus, after day 70, when lanadelumab had reached steady-state concentration, more than 50% of patients in the lanadelumab 300-mg q2w treatment arm did not have an attack during the rest of the 6-month study period, and the median number of days to first attack after day 70 in the 300-mg q4w arm was 61 compared with 12 in the placebo arm. Based on the predicted survival curves, the proportion of attack-free patients after the first six months of treatment with lanadelumab 300 mg q2w (45% and 72%) increased as time to first attack was assessed later (after day 0 and day 70, respectively); a similar pattern was observed with the lanadelumab 300 mg q4w (31% and 37%, respectively) and 150 mg q4w (36% and 47%, respectively) treatment arms, but patients receiving C1-INH showed an opposite pattern of decreases (20% and 13%, respectively) with subsequent assessment. These findings remained generally consistent upon extrapolation of these data out to 60 months.

Accordingly, HAE patients on lanadelumab treatment for a period (e.g., 6 months) and showed free of HAE attach may receive a reduced dosage of lanadelumab, for example, from 300 mg/2 weeks to 300 mg/4 weeks.

Example 2: Indirect Treatment Comparison of DX-2930 and Intravenous C1 Esterase Inhibitor Treatments Using Individual Patient Data from the HELP-03 and CHANGE Studies Objectives The objective was to perform an indirect treatment comparison (ITC) of lanadelumab (300 mg subcutaneous every 2 weeks (300 mg SC q2w), 300 mg subcutaneous every four weeks (300 mg SC q 2w)) and Cinryze® (C1-INH) 1000 units intravenous (1000 U IV) using individual patient data (IPD) from the HELP-03 (HELP) and CHANGE studies. Using IPD in lieu of aggregated data is advantageous for several reasons. First, IPD provides more information, which reduces heterogeneity across networks and resolves potential issues of inconsistency. Further, IPD facilitates estimation of subgroup effects, aids convergence, and overall, yields more precise estimates. Additionally, IPD allows within-study associations to be distinguished from across-study associations. Utilizing IPD, even only from a few studies, can also reduce ecological bias, which is often problematic when the evidence is sparse and the sample sizes are small.

Outcomes of Interest

Both the HELP and CHANGE studies cited the number of HAE attacks per 28 days. A prior study by BresMed reported the time to first HAE attack following treatment at day 0 and 70 in the HELP study. This outcome measure was estimated using IPD reported in the CHANGE study. Only the HELP study disclosed the proportion of patients who experience ≥50% reduction in the number of attacks. While the CHANGE study did not report this outcome measure, it was not considered relevant for the ITC.

Conclusion

Overall, the similarity assumption was not deemed to hold between the HELP and CHANGE studies with respect to the baseline HAE attack rate per 28 days. This was confirmed by expert clinician opinion. Other covariates of interest (e.g., age, gender, and weight) also differed between the studies, but these were considered to have a lesser impact on the results. Therefore, it was determined that the base case analysis would account for HAE attack rate per 28 days at baseline, while regression models in sensitivity analyses would include other key covariates which might potentially modify treatment effects. Any differences between the base case and sensitivity analysis findings might indicate that the results of the base case were not robust and may possibly be driven by the study differences. In this case, a second sensitivity analysis is planned to evaluate whether an assessment of attacks per patient or investigators influences the results of the attack rates per 28 days. To account for this, the analysis will include only patient-reported HAE attacks in both studies.

Common Comparator

Figure 6:
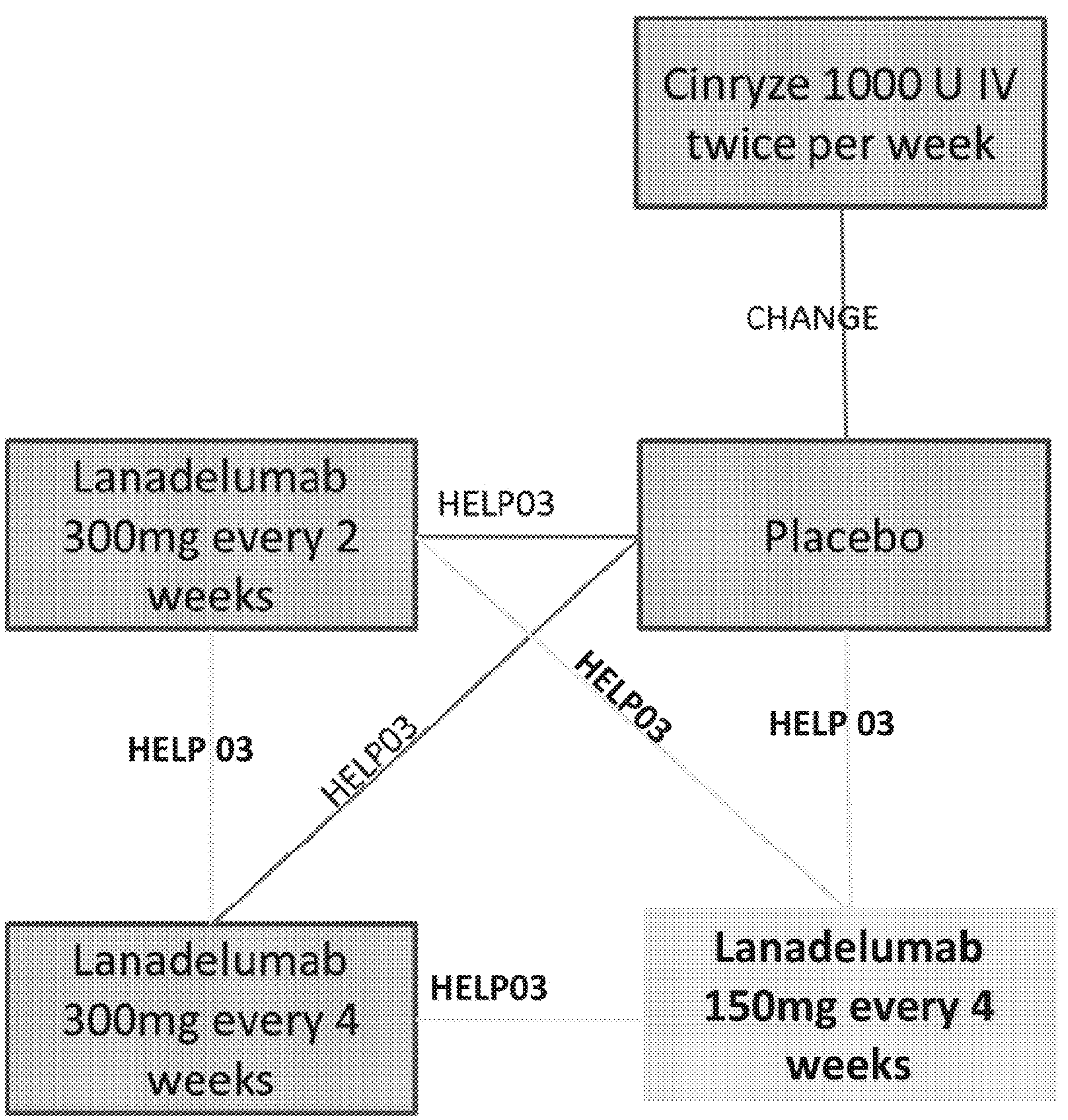
FIG. 6 is a network of evidence for the comparators in the HELP (HELP-03) and CHANGE studies. Cinryze® is a C1-INH, C1 esterase inhibitor.

As shown in the network of evidence in FIG. 6, the common comparator for Cinryze® (C1-INH) and lanadelumab in the HELP and CHANGE studies was placebo. The HELP study compared three different lanadelumab dose regimens to placebo, whereas the CHANGE study was a cross-over study comparing Cinryze® to placebo. Excluding the lanadelumab 150 mg dose (not approved for this indication) reduced the number of comparisons and circumvented the issue of multiplicity (e.g., multiple hypothesis testing). If multiple hypotheses are tested simultaneously, the alpha error increases, and therefore the significance level requires adjustment (e.g., Bonferroni). Identifying statistically significant differences at the significance level <5% may be difficult. Therefore, it is advised that multiple hypothesis testing be avoided.

Methods

Statistical approaches to evidence synthesis can be characterized primarily as frequentist or Bayesian methods. Frequentist methods, such as adjusted indirect comparisons (e.g., Bucher method, matched-adjusted indirect comparison [MAIC], and simulated treatment comparison [STC]), allow the indirect comparison of two interventions in a single step. The term network meta-analysis (NMA) refers to the simultaneous comparison of a larger network of interventions. In a Bayesian method, minimally informative priors are usually assigned treatment effects.

For the purposes of this ITC, a frequentist approach was preferred over a Bayesian approach due to the limited evidence base (N=2 studies). Currently, various frequentist approaches for including IPD in statistical models for evidence synthesis exist. These methods differ mainly on the basis of inclusion or exclusion of a common comparator arm ("anchor").

As a second step, the Bucher method is often used to combine the relative treatment effects in anchored comparisons for obtaining the final ITC results. Only two interventions may be compared at once. If multiple comparisons are of interest, multiple analyses must be conducted. The corresponding point estimates are expected to be very similar to those obtained through a Bayesian analysis. However, the 95% confidence intervals are usually not as wide as the credible intervals of a Bayesian analysis.

Following an extensive feasibility assessment, the present ITC was performed using a frequentist-based anchored approach. Importantly, this approach preserved randomization. In the base case analysis, regression models included the HAE attack rate per 28 days at baseline. Other covariates of interest (e.g., age, gender, and weight) were added in sensitivity analyses to investigate the overall impact of these variables on the results. A second sensitivity analysis evaluated the impact of patient-reported HAE attacks not confirmed by investigators on the base case results.

Poisson Regression—HAE Attack Rate Per 28 Days

Poisson regression analyses were performed to estimate rate ratios (RRs) for the HAE attack rates per 28 days. Poisson regression requires that the following assumptions are met: (1) observations are independent, (2) the counts follow a Poisson distribution, and (3) the conditional mean and variance of the model are identical.

Given that the outcome of interest (HAE attack rate per 28 days) is expressed as count data, Poisson regression was deemed appropriate, and the number of attacks per treatment period was considered in the models. Following Banjeri et al., the models included an offset variable in order to adjust for differences in follow-up time. The offset was defined as the logarithm of the number of days a patient was observed during the treatment period.

Measures of treatment effects (model inputs) were expressed as the estimated RR of attacks per 28 days. For the lanadelumab regimens (300 mg q2w and 300 mg q4w), this measure was represented as the ratio of the rate of attacks per 28 days during the respective treatment relative to that with placebo. For Cinryze® (C1-INH), the RR indicated the ratio of the rate of attacks per 28 days during treatment with Cinryze® relative to that with placebo. The estimated RRs generated by the Poisson models were then input into the ITC.

Non-Parametric Estimation and Cox Regression

For the outcome "time to first attack" a Cox regression analysis was conducted to estimate the hazard ratio (HR) of first attack with each of the lanadelumab regimens (300 mg q2w and 300 mg q4w) relative to placebo, and the HR of a first attack with Cinryze® relative to placebo. As described, the estimated HRs were then input into the ITC (via the Bucher method) comparing the lanadelumab dose regimens and Cinryze®. While Cox regression is semi-parametric and therefore, does not specify requirements regarding the form of the baseline hazard, the following assumptions must be met: (1) the proportional hazard, (2) linear relationship between covariates, and (3) independent observations.

Kaplan-Meier curves were derived via non-parametric estimation to model the outcome "time to first attack after 0 and 70 days". Patients were censored at the date of their last data capture. The graphs showed that the hazard functions were proportional over time and therefore, statistical measures to account for non-proportional hazards were not required.

In the base case, the model was adjusted for the number of HAE attacks per 28 days at baseline. For the sensitivity analyses, the model also included relevant covariates (age, gender, and weight). Due to the small sample size in the CHANGE study, no formal variable selection was conducted. Estimates obtained from these adjusted models were compared to unadjusted estimates from a model excluding the covariates.

Since the CHANGE study was a cross-over study, individuals who were observed twice (under placebo and Cinryze® treatment) were not independent. As described, mixed models, including fixed factors for treatment, period, and sequence, and a random effect for study subjects, were employed to account for repeated measurements in the study.

Results

1. HAE Attack Rate Per 28 Days

Table 6 shows that the respective baseline attack rates for placebo and Cinryze® treatment were identical. The CHANGE cross-over study did not include a run-in period. The attack rate per 28 days was higher with placebo during the treatment period compared to the baseline attack rate with Cinryze® treatment. The mean number of attacks per treatment period was considerably lower for Cinryze® than for placebo. Treatment duration was comparable between the two interventions. The time to first attack after 0 and 70 days of treatment was considerably shorter with placebo than with Cinryze® treatment.

TABLE 6

Descriptive Statistics on HAE Attacks in the CHANGE Study.

| Variable | Number (N) | Mean | Standard Deviation | Minimum | Maximum |
|---|---|---|---|---|---|
| Placebo Treatment | | | | | |
| Baseline rate | 22 | 3.80 | 1.95 | 1.84 | 8.00 |
| Rate per 28 days during treatment period | 22 | 4.24 | 1.55 | 1.98 | 6.83 |
| Number of attacks per treatment period | 22 | 12.73 | 4.80 | 6.00 | 22.00 |
| Duration of treatment period (days) | 22 | 84.05 | 5.96 | 67.00 | 96.00 |
| Time to first attack after 0 days of treatment | 22 | 4.77 | 7.85 | 0.00 | 32.00 |
| Time to first attack after 70 days of treatment | 21 | 3.48 | 3.41 | 0.00 | 14.00 |
| Cinryze ® Treatment | | | | | |
| Baseline rate | 22 | 3.80 | 1.95 | 1.84 | 8.00 |
| Rate per 28 days during treatment period | 22 | 2.09 | 1.85 | 0.00 | 5.88 |
| Number of attacks per treatment period | 22 | 6.14 | 5.43 | 0.00 | 17.00 |
| Duration of treatment period (days) | 22 | 80.05 | 10.42 | 34.00 | 86.00 |
| Time to first attack after 0 days of treatment | 22 | 20.68 | 28.16 | 0.00 | 82.00 |
| Time to first attack after 70 days of treatment | 21 | 7.10 | 4.30 | 0.00 | 14.00 |

TABLE 7

Descriptive Statistics on HAE Attacks in the HELP Study.

| Variable | Number (N) | Mean | Standard Deviation | Minimum | Maximum |
|---|---|---|---|---|---|
| Placebo Treatment | | | | | |
| Baseline rate | 41 | 4.02 | 3.26 | 0.97 | 14.67 |
| Rate per 28 days during treatment period | 41 | 2.45 | 2.08 | 0.00 | 8.31 |
| Number of attacks per treatment period | 41 | 13.95 | 12.01 | 0.00 | 54.00 |
| Duration of treatment period (days) | 41 | 168.39 | 45.37 | 13.00 | 197.00 |
| Time to first attack after 0 days of treatment | 41 | 21.41 | 34.45 | 2.00 | 183.00 |
| Time to first attack after 70 days of treatment | 37 | 21.43 | 28.68 | 1.00 | 113.00 |
| Lanadelumab 300 mg q4w | | | | | |
| Baseline rate | 29 | 3.71 | 2.51 | 0.97 | 10.50 |
| Rate per 28 days during treatment period | 29 | 0.60 | 0.80 | 0.00 | 2.91 |
| Number of attacks per treatment period | 29 | 3.62 | 4.80 | 0.00 | 19.00 |
| Duration of treatment period (days) | 29 | 178.17 | 21.68 | 73.00 | 188.00 |
| Time to first attack after 0 days of treatment | 29 | 74.90 | 77.96 | 1.00 | 185.00 |
| Time to first attack after 70 days of treatment | 29 | 62.62 | 46.18 | 2.00 | 115.00 |
| Lanadelumab 300 mg q2w | | | | | |
| Baseline rate | 27 | 3.52 | 2.33 | 0.97 | 9.00 |
| Rate per 28 days during treatment period | 27 | 0.31 | 0.50 | 0.00 | 1.85 |
| Number of attacks per treatment period | 27 | 1.70 | 2.83 | 0.00 | 12.00 |
| Duration of treatment period (days) | 27 | 177.74 | 28.56 | 35.00 | 186.00 |

TABLE 7-continued

Descriptive Statistics on HAE Attacks in the HELP Study.

| Variable | Number (N) | Mean | Standard Deviation | Minimum | Maximum |
|---|---|---|---|---|---|
| Time to first attack after 0 days of treatment | 27 | 97.04 | 80.53 | 1.00 | 186.00 |
| Time to first attack after 70 days of treatment | 26 | 92.42 | 40.04 | 6.00 | 116.00 |

As shown in Table 7, both lanadelumab 300 mg q2w and 300 mg q4w reduced the mean number of attacks per treatment period compared to placebo. The mean baseline attack rates were comparable across the three study arms. Treatment duration was shortest in the placebo arm, while the time to first attack was longer with lanadelumab treatment (300 mg q2w and 300 mg q4w) compared to placebo.

HAE Attack Rate Per 28 Days—Poisson Regression

Further, the estimated mean HAE attack rate per 28 days was 1.99 (95% CI: 1.56; 2.52) with Cinryze® treatment and 4.03 (95% CI: 3.31; 4.91) with placebo. The corresponding RR (0.49) indicated that patients treated with Cinryze® had 0.49 times the rate of HAE attacks compared to those treated with placebo. This difference was statistically significant (since the corresponding 95% CI does not include 1). The resulting percent change for the mean attack rate was-51% for patients treated with Cinryze® relative to placebo.

TABLE 8

Base Case Results in the CHANGE Study.

| | Treatment | Estimate | 95% CI Lower | 95% CI Upper |
|---|---|---|---|---|
| Model-based treatment period HAE attack rate (attacks/28 days) | C1-INH | 1.99 | 1.56 | 2.52 |
| | Placebo | 4.03 | 3.31 | 4.91 |
| Rate ratio | | 0.4926 | 0.3950 | 0.6142 |
| % change in mean attack rate | | −51% | −60% | −39% |

As shown in Table 9, the estimated mean HAE attack rate per 28 days was 0.26 (95% CI: 0.15; 0.45) with lanadelumab 300 mg q2w, 0.54 (95% CI: 0.37, 0.77) with lanadelumab q2w, and 2.0 (95% CI: 1.69; 2.38) with placebo treatment. The corresponding RRs indicated that patients treated with lanadelumab 300 mg q2w and lanadelumab q4w had 0.13 and 0.27 times the rate of HAE attacks, respectively, compared to patients treated with placebo. These estimates were statistically significant as evidenced by exclusion of the value “1” in the corresponding 95% CIs. The resulting percent change in mean attack rate was −87% for patients treated with lanadelumab 300 mg q2w and −73% for those treated with lanadelumab 300 mg q2w relative to placebo.

TABLE 9

Base Case Results in the HELP Study.

| | Treatment | Estimate | 95% CI Lower | 95% CI Upper |
|---|---|---|---|---|
| Model-based treatment period HAE attack rate (attacks/28 days) | Lanadelumab 300 mg q2w | 0.26 | 0.15 | 0.45 |
| | Lanadelumab 300 mg q4w | 0.54 | 0.37 | 0.77 |
| | Placebo | 2.00 | 1.69 | 2.38 |
| Rate ratio | Lanadelumab 300 mg q2w vs. placebo | 0.1309 | 0.0742 | 0.2309 |
| | Lanadelumab 300 mg q4w vs. placebo | 0.2674 | 0.1803 | 0.3965 |
| % change in mean attack rate | Lanadelumab 300 mg q2w vs. placebo | −87% | −93% | −77% |
| | Lanadelumab 300 mg q4w vs. placebo | −73% | −82% | −60% |

Indirect comparison using the Bucher method (Table 10) showed that patients treated with lanadelumab 300 mg q2w and lanadelumab 300 mg q4w had 0.27 times and 0.54 times the rate of HAE attacks, respectively, compared to those treated with Cinryze®. These results were statistically significant as evidenced by exclusion of the value “1” in the corresponding 95% CIs. The resulting percent changes in the mean attack rate relative to Cinryze® were −73% and −46% for patients treated with lanadelumab 300 mg q2w and lanadelumab 300 mg q4w, respectively. The point estimates and credible/confidence intervals generated in this ITC of IPD appeared consistent with the findings in Bayesian NMA.

TABLE 10

Indirect Comparison of Lanadelumab and Cinryze ® using the Bucher Method( Base Case).

| Treatment 1 | Treatment 2 | ITC RR | ITC 95% CI Lower | ITC 95% CI Upper | Bayesian NMA RR |
|---|---|---|---|---|---|
| Lanadelumab 300 mg q2w | Cinryze ® | 0.2657 | 0.1451 | 0.4864 | 0.27 (0.14; 0.51) |
| % change in mean attack rate −73% (CI; −85%; −51%) | | | | | |
| Lanadelumab 300 mg q4w | Cinryze ® | 0.5429 | 0.3478 | 0.8473 | 0.54 (0.34; 0.86) |
| % change in mean attack rate −46% (CI: −65%, −15%) | | | | | |

Sensitivity Analysis Accounting for Patient-Reported HAE Attacks in the HELP Study As shown in Table 11, the estimated mean HAE attack rate per 28 days was 0.27 (CI: 0.16; 0.46) with lanadelumab 300 mg q2w, 0.55 (CI: 0.38; 0.78) with lanadelumab 300 mg q4w, and 2.02 (95% CI: 1.71; 2.39) with placebo. The corresponding RRs indicated that patients treated with lanadelumab 300 mg q2w and those treated with lanadelumab 300 mg q4w had 0.13 and 0.27 times the rate of HAE attacks, respectively, compared to those treated with placebo. These estimates were statistically significant since the corresponding 95% CI does not include 1. The percent changes in mean attack rate relative to placebo were −87% and −73% for patients treated with lanadelumab 300 mg q2w and for those treated with lanadelumab 300 mg q4w, respectively.

TABLE 11

Results for Patient-reported HAE attacks (HELP study).

| | Treatment | RR | 95% CI Lower | 95% CI Upper |
|---|---|---|---|---|
| Model-based treatment period HAE attack rate (attacks/28 days) | Lanadelumab 300 mg q2w | 0.27 | 0.16 | 0.46 |
| | Lanadelumab 300 mg q4w | 0.55 | 0.38 | 0.78 |
| | Placebo | 2.02 | 1.71 | 2.39 |
| Rate ratio | Lanadelumab 300 mg q2w vs. placebo | 0.1327 | 0.0758 | 0.2324 |
| | Lanadelumab 300 mg q4w vs. placebo | 0.2704 | 0.1832 | 0.3992 |
| % change in mean attack rate | Lanadelumab 300 mg q2w vs. placebo | −87% | −92% | −77% |
| | Lanadelumab 300 mg q4w vs. placebo | −73% | −82% | −60% |

In the base case, indirect comparison via the Bucher method showed that patients treated with lanadelumab 300 mg q2w had 0.27 times the rate of HAE attacks compared to those treated with Cinryze® (Table 12), while those treated with lanadelumab 300 mg q4w experienced 0.55 times the rate of HAE attacks compared to those treated with Cinryze®. These estimates were statistically significant since the corresponding 95% CI does not include 1. The percent changes in the mean attack rate relative to Cinryze® were −73% and −45% for treatment with lanadelumab 300 mg q2w and lanadelumab 300 mg q4w, respectively. A comparable sensitivity analysis was not conducted in the Bayesian NMA.

TABLE 12

Indirect Comparison Using the Bucher method (Patient-reported HAE Attacks from HELP Study).

| Treatment 1 | Treatment 2 | ITC RR | ITC 95% CI Lower | ITC 95% CI Upper | Bayesian NMA |
|---|---|---|---|---|---|
| Lanadelumab 300 mg q2w | Cinryze ® | 0.2694 | 0.1482 | 0.4896 | N/A |
| % change in mean attack rate -73% (95% CI: −85%; −51%) | | | | | |
| Lanadelumab 300 mg q4w | Cinryze ® | 0.5490 | 0.3532 | 0.8535 | NA |
| % change in mean attack rate -45% (95% CI −65%; −15%) | | | | | |

Sensitivity Analysis Accounting for all Covariates (Normalized Baseline Attack Rate, Age, Gender, Weight)

As shown in Table 13, the estimated mean HAE attack rate per 28 days was 2.21 (95% CI: 1.43; 3.41) with Cinryze® and 4.37 (95% CI: 2.89; 6.60) with placebo. The corresponding RR of 0.51 indicated that patients treated with Cinryze® had 0.51 times the mean rate of HAE attacks compared to those treated with placebo. This result was statistically significant since the corresponding 95% CI does not include 1. The resulting percent change in the mean attack rate with Cinryze® treatment relative to placebo was-49%.

TABLE 13

Results for HAE Attacks Accounting for All Covariates of Interest (CHANGE Study).

| | Treatment | Estimate | 95% CI Lower | 95% CI Upper |
|---|---|---|---|---|
| Model-based treatment period HAE attack rate (attacks per 28 days) | Cinryze ® | 2.21 | 1.43 | 3.41 |
| | Placebo | 4.37 | 2.89 | 6.60 |
| Rate ratio | | 0.5053 | 0.4032 | 0.6332 |
| % change in mean attack rate | | −49% | −60% | −37% |

As shown in Table 14, the estimated mean HAE attack rate per 28 days was 0.27 (95% CI; 0.16; 0.46) for lanadelumab 300 mg q2w, 0.54 (95% CI; 0.37; 0.78) for lanadelumab 300 mg q4w, and 2.00 (95% CI; 1.63; 2.45) for placebo. The corresponding RRs showed that patients treated with lanadelumab 300 mg q2w and those treated with lanadelumab 300 mg q4w had 0.14 and 0.27 times the rate of HAE attacks, respectively, compared to patients who received placebo. These results were statistically significant since the corresponding 95% CI does not include 1. The resulting percent changes in the mean attack rate relative to placebo were −86% and −73% for lanadelumab 300 mg q2w and lanadelumab 300 mg q4w, respectively.

TABLE 14

Results for HAE Attacks Accounting for All Covariates of Interest (HELP study).

| | Treatment | Estimate | 95% CI Lower | 95% CI Upper |
|---|---|---|---|---|
| Model-based treatment period HAE attack rate (attacks/28 days) | Lanadelumab 300 mg q2w | 0.27 | 0.16 | 0.48 |
| | Lanadelumab 300 mg q4w | 0.54 | 0.37 | 0.78 |
| | Placebo | 2.00 | 1.63 | 2.45 |
| Rate ratio | Lanadelumab 300 mg q2w vs. placebo | 0.1371 | 0.0763 | 0.2465 |
| | Lanadelumab 300 mg q4w vs. placebo | 0.2693 | 0.1808 | 0.4011 |
| % change in mean attack rate | Lanadelumab 300 mg q2w vs. placebo | −86% | −92% | −75% |
| | Lanadelumab 300 mg q4w vs. placebo | −73% | −82% | −60% |

For the base case, indirect comparison via the Bucher method showed that patients treated with lanadelumab 300 mg q2w and lanadelumab 300 mg q4w experienced 0.27 times and 0.53 times the rate of HAE attacks, respectively, compared to those treated with Cinryze® (Table 15). These results were statistically significant as evidenced by exclusion of the value "1" in the corresponding 95% CIs. The resulting percentage change in mean attack rate relative to Cinryze® was-73% and −47% for patients treated with lanadelumab 300 mg q2w and lanadelumab 300 mg q4w, respectively. No Bayesian NMA results were available for this sensitivity analysis.

TABLE 15

Indirect Comparison of Lanadelumab in Different Dosing Regimens and Cinryze ® Using the Bucher Method (All Covariates of Interest).

| | | ITC | | | |
|---|---|---|---|---|---|
| Treatment 1 | Treatment 2 | RR | 95% CI Lower | 95% CI Upper | Bayesian NMA |
| Lanadelumab 300 mg q2w | Cinryze ® | 0.2714 | 0.1456 | 0.5061 | N/A |
| % change in mean attack rate −73% (95% CI: −85%; −49%) | | | | | |
| Lanadelumab 300 mg q4w | Cinryze ® | 0.5329 | 0.3396 | 0.8634 | NA |

% change in mean attack rate −47% (95% CI −66%; −15%)

This section summarizes the results of the ITC of lanadelumab (300 mg q2w and 300 mg q4w) and Cinryze®. The base case and two sensitivity analyses demonstrated statistically significant differences in the HAE attack rates per 28 days between lanadelumab (300 mg q2w and 300 mg q4w) and Cinryze®.

Two independent Poisson regression models generated RR estimates identifying the relative treatment effects of lanadelumab (300 mg q2w and 300 mg q4w) vs. placebo and Cinryze® vs. placebo. The base case accounted for the normalized HAE attack rate per 28 days at baseline, while a mixed model was used to account for the cross-over design of the CHANGE study. Using the Bucher method, the corresponding results were applied as inputs into the ITC.

The first sensitivity analysis included all HAE attacks reported in the HELP study, regardless of whether or not the attacks had been confirmed by an investigator. Regression models for a second sensitivity analysis initially included age, gender, and weight. The two sensitivity analyses yielded results consistent with the base case and did not change the conclusions. These findings were also confirmed by the lack of statistically significant effects for the covariates (apart from normalized baseline attack rate) on the results.

2. Comparability of Placebo Effects in CHANGE and HELP Studies

Figure 7:
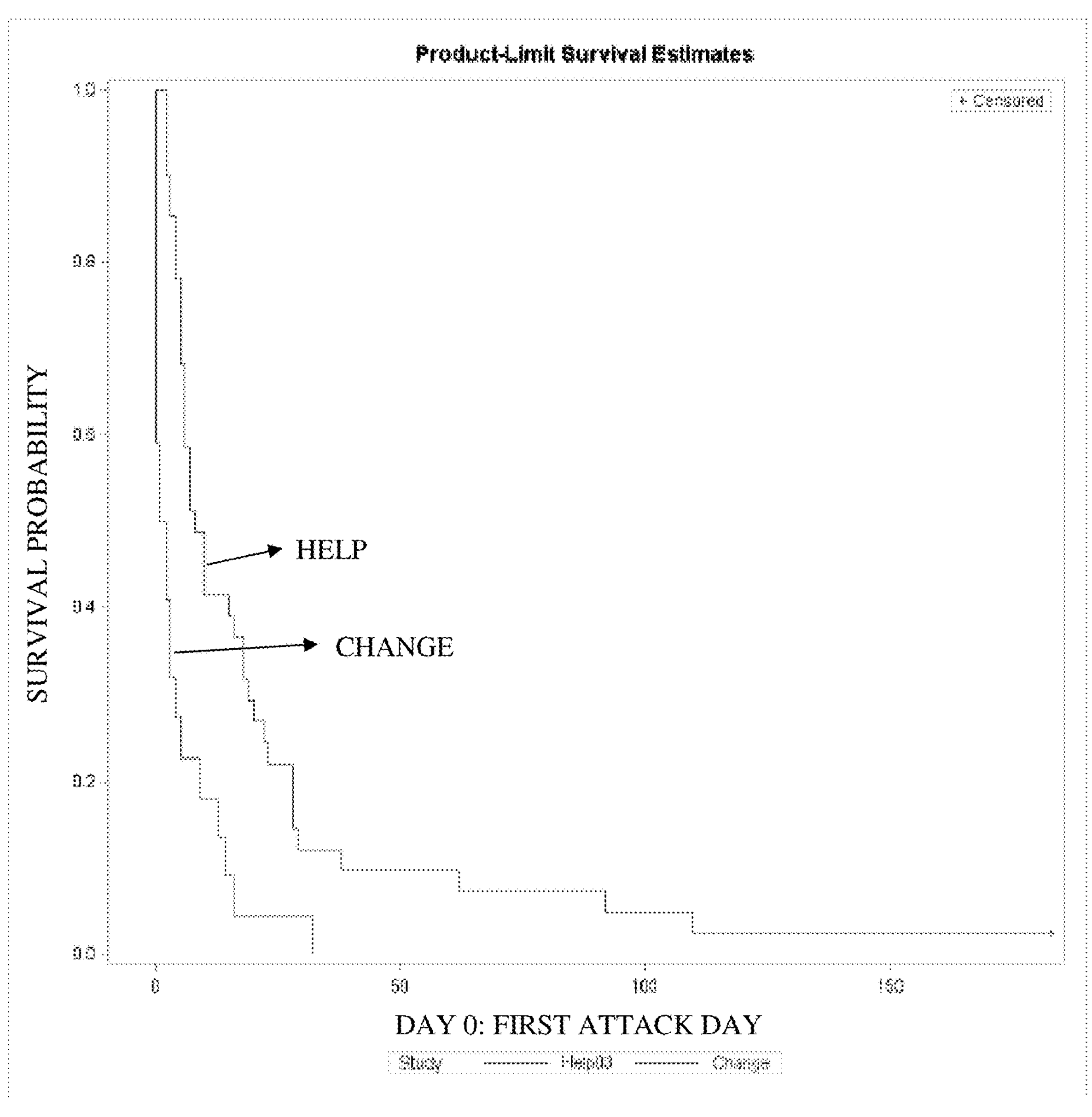
FIG. 7 is a predicted survival graph comparing time to first attack after 0 days of treatment with placebo in the HELP (HELP-03) and CHANGE studies.

The output of the non-parametric estimation showed that the mean time (days) to the first attack after 0 days of placebo was considerably shorter in the CHANGE study than in the HELP study (4.773 days [SE 1.673] vs. 19.634 days [SE 4.212]). In FIG. 7, the probability of "no first attack" after 0 days of treatment is plotted on the y-axis while the observation time horizon is plotted on the x-axis. Placebo treatment in the CHANGE and HELP studies was not equally effective; patients in the CHANGE study experienced first attacks considerably earlier than those in the HELP study, and the corresponding observation time horizon was much shorter.

Figure 8:
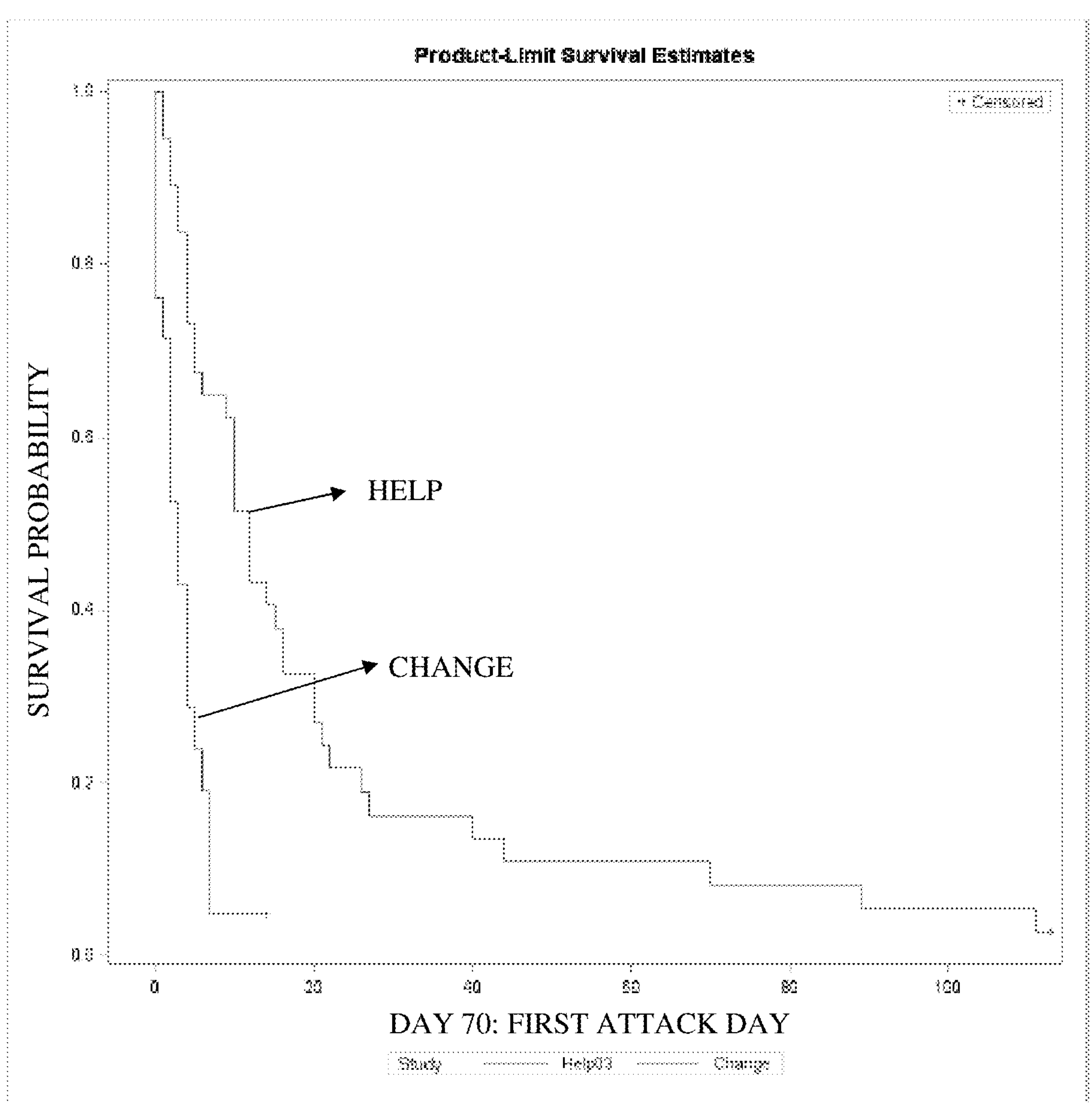
FIG. 8 is a predicted survival graph comparing time to first attack after 70 days of treatment with placebo in the HELP (HELP-03) and CHANGE studies.

The output of the non-parametric estimation showed that the mean time (days) to the first attack after 70 days of placebo was considerably shorter in the CHANGE study than in the HELP study (3.143 days [SE 0.563] vs. 21.378 days [SE 4.687]). In FIG. 8, the probability of "no first attack" after 70 days of treatment is plotted on the y-axis, while the observation time horizon is plotted on the x-axis. Placebo treatment in the CHANGE and HELP studies was not equally effective; patients in the CHANGE study experienced first attacks considerably earlier than those in the HELP study, and the corresponding observation time horizon was much shorter.

This section summarizes the findings of the analysis comparing the placebo effects between the CHANGE and HELP studies. Placebo effects with respect to the time to first attack after 0 days of treatment and time to first attack after 70 days of treatment were not comparable between the two studies. This was assessed via the Kaplan-Meier graphs, various statistical tests (log-rank, Wilcoxon, likelihood ratio tests), and Cox regression models, which included the normalized attack at baseline, age, gender, and weight as covariates and accounted for differences in study design. There was no placebo effect in the CHANGE study, where individuals experienced fewer attacks at baseline then during placebo treatment. A placebo effect was observed in the HELP study.

In a randomized controlled trial, patients are randomly assigned to treatment arms to ensure comparability of relevant covariates between the groups. An ITC is conducted in the event that head-to-head treatment comparisons are lacking. The similarity assumption between studies must hold to ensure that results of the ITC are valid. Therefore, covariates of interest must be comparable between the corresponding study arms. This is usually ascertained during the process of feasibility assessment.

Placebo effects are often not comparable between the studies included in an ITC. However, evaluating the implications of these differences is not straightforward. With respect to the present ITC, differences between placebo effects might have favored either Cinryze® or lanadelumab. The absence of a placebo effect in the CHANGE study implied that patients during C1-INH treatment may have only benefited from the effect of the active treatment without additional placebo effects. This would be expected to occur even if Cinryze® were not efficacious. In contrast, a placebo effect was observed in the HELP study. Therefore, patients treated with lanadelumab may have benefited from the efficacy of active treatment as well as the additional placebo effect. This difference may have favored lanadelumab over Cinryze® in the present analysis.

In a linear regression on the change from baseline for the HAE attack rate per 28 days, the outcome measure of interest is the rate difference. The rate difference in change from baseline in comparison to placebo was higher in the CHANGE study than in the HELP study since no placebo effect was observed in the former, leading to ITC results favoring Cinryze®.

In Poisson regression, however, the relative treatment effect is defined as the RR at follow-up, and the baseline attack rate is included as a covariate. Compared to linear regression, the analysis uses a different measure of outcome. As a result, the differences regarding the placebo effect between the two studies had little impact on the analysis, and demonstrating a statistically significant difference favoring lanadelumab over Cinryze® was feasible.

As for time to first attack after 0 and 70 days of treatment, attacks occurred more frequently and considerably earlier during placebo treatment in the CHANGE study than in the HELP study. As discussed, assessing the implications of these findings is not straightforward.

3. Time to First Attack—Non-Parametric Estimation and Cox Regression

In the non-parametric estimation, the mean time to first attack (in days) after 0 days of placebo treatment was considerably shorter in the CHANGE study than in the HELP study (4.773 days [SE 1.673] vs. 19.634 days [SE 4.212]).

Figure 9:
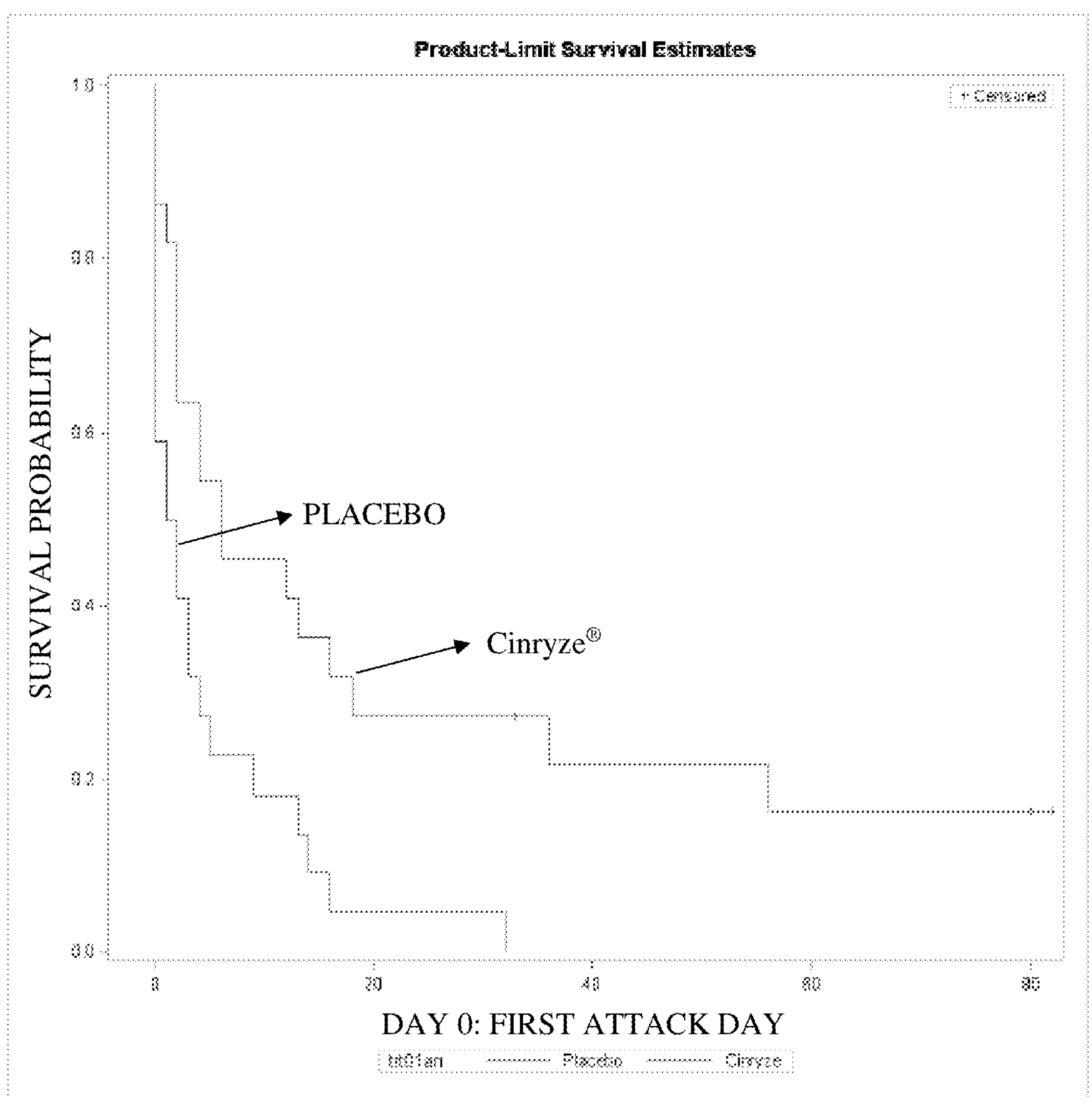
FIG. 9 is a predicted survival graph comparing time to first attack after 0 days of treatment with placebo or Cinryze® (C1-INH) in the CHANGE study.

As shown in FIG. 9, the probability of "no first attack" after 0 days of treatment is plotted on the y-axis, while the observation time horizon is plotted on the x-axis. Placebo was less effective than Cinryze® treatment in the CHANGE study. Patients who received placebo experienced their first attacks considerably earlier than during Cinryze® treatment. Given that the two curves do not intersect, the proportional hazards assumptions may be deemed to hold. That confirms that Cox regression is a valid method for estimating hazard ratios (HRs) for the ITC.

Figure 10:
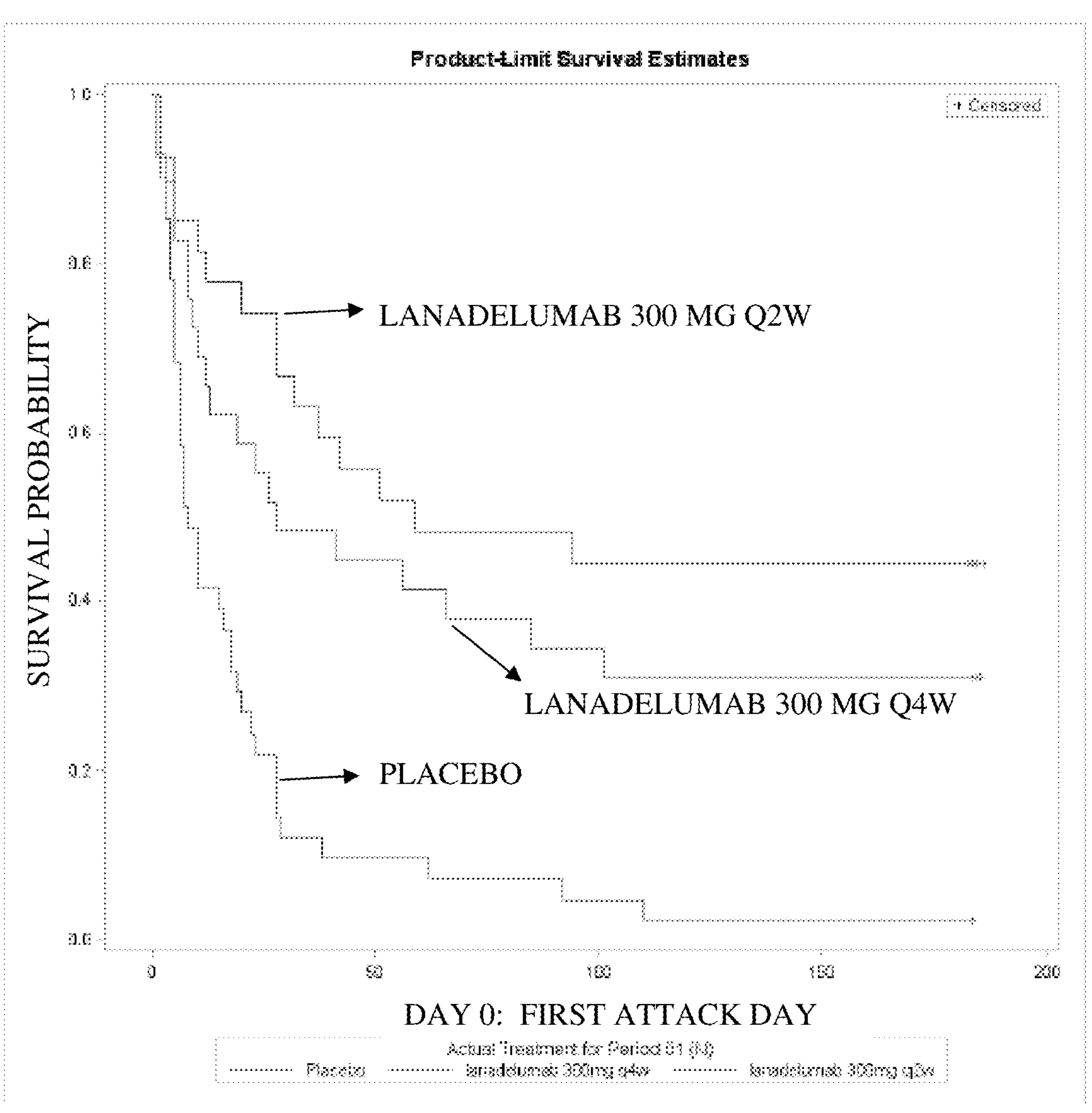
FIG. 10 is a predicted survival graph comparing time to first attack after 0 days of treatment with placebo, 300 mg lanadelumab every 2 weeks (300 mg q2w), or 300 mg lanadelumab every 4 weeks (300 mg q4w) in the HELP (HELP-03) study.

As shown in FIG. 10, the probability of "no first attack" after 0 days of treatment is plotted on the y-axis, while the observation time horizon is plotted on the x-axis. In the HELP study, placebo was less effective than the two lanadelumab dose regimens. Patients receiving placebo experienced first attacks considerably earlier than those during lanadelumab treatment. Given that none of the curves intersect, the proportional hazards assumption may be deemed to hold. This confirms that Cox regression is a valid method for estimating HRs for the ITC.

The different analytical methods used may contribute to discrepant findings. The present ITC employed a frequentist Cox regression model, which accounted for repeated measurements (including fixed effects for treatment period and sequence and random effects for study subjects), and the baselined HAE attack rate was normalized. In the prior NMA, which employed a Bayesian approach, these measures were not taken and only the results of random effects models used for comparisons were reported.

In comparing lanadelumab 300 mg q2w and lanadelumab 300 mg q4w to placebo, the Cox regression generated HRs of 0.27 (95% CI: 0.15; 0.50) and 0.38 (95% CI: 0.22; 0.67), respectively (Table 16). The Bayesian NMA produced comparable HRs of 0.27 with corresponding 95% credible interval (Crl) of (0.13; 0.55) and 0.39 with 95% Crl of (0.21; 0.74), respectively.

TABLE 16

Base Case Results from HELP Study.

| Contrast | HR | Standard Error | Confidence Limits | | Bayesian NMA (FE): HR and 95% credible interval (Crl) |
|---|---|---|---|---|---|
| Lanadelumab 300 mg q2w vs placebo | 0.2689 | 0.0843 | 0.1454 | 0.4972 | 0.27 (0.13; 0.55) |
| Lanadelumab 300 mg q4w vs placebo | 0.3837 | 0.1079 | 0.2211 | 0.6657 | 0.39 (0.21; 0.74) |

TABLE 17

Base Case Results from CHANGE Study.

| Contrast | HR | Standard Error | Confidence Limits | | Bayesian NMA : HR (RE, FE not reported) |
|---|---|---|---|---|---|
| Cinryze ® vs. placebo | 0.3669 | 0.1287 | 0.1845 | 0.7298 | 0.7298 |

Indirect comparison via the Bucher method showed that individuals treated with lanadelumab 300 mg q2w had 0.73 times the hazard of a first HAE attack after 0 days of treatment compared to individuals treated with Cinryze® (Table 18). Treatment with lanadelumab 300 mg q4w increased the hazard of an attack by 1.05 times compared to Cinryze®. This finding was not statistically significant as evidenced by inclusion of the value "1" in the corresponding 95% CIs. The point estimates generated in the ITC using IPD differed from the results of the Bayesian NMA, primarily due to the different methodologies applied (as previously described). As the interval bounds appeared similar, the conclusions did not change.

TABLE 18

Indirect Comparison of Lanadelumab (300 mg q2w and 300 mg q4w) and Cinryze ® using the Bucher Method (Base Case).

| | | ITC | | | Bayesian |
|---|---|---|---|---|---|
| Treatment 1 | Treatment 2 | HR | 95% CI Lower | 95% CI Upper | NMA HR (95% Crl) |
| Lanadelumab 300 mg q2w | Cinryze ® | 0.7327 | 0.2913 | 1.8429 | 0.51 (0.22; 1.3) |
| Lanadelumab 300 mg q4w | Cinryze ® | 1.0456 | 0.4332 | 2.5239 | 0.73 (0.26; 2.09) |

In comparing Cinryze® and placebo, the Cox regression generated a HR of 0.37 (95% CI; 0.18; 0.76) (Table 19). These results were consistent with the base case.

TABLE 19

Base results in the CHANGE Study.

| Contrast | HR | SE | 95% CI Lower | 95% CI Upper |
|---|---|---|---|---|
| Cinryze ® vs. placebo | 0.3738 | 0.1349 | 0.1843 | 0.7582 |

In comparing lanadelumab 300 mg q2w and lanadelumab 300 mg q4w to placebo, the Cox regression generated HRs of 0.27 (95% CI: 0.14; 0.51) and 0.37 (95% CI: 0.21; 0.66), respectively (Table 20). These estimates are consistent with previous findings. Including additional covariates did not affect the primary findings.

TABLE 20

Base Case Results in the HELP Study.

| Contrast | HR | SE | 95% CI Lower | 95% CI Upper |
|---|---|---|---|---|
| Lanadelumab 300 mg q2w vs. placebo | 0.2675 | 0.0890 | 0.1394 | 0.5133 |
| Lanadelumab 300 mg q4w vs. placebo | 0.3733 | 0.1071 | 0.2127 | 0.6552 |

Indirect comparison via the Bucher method estimated that patients treated with lanadelumab 300 mg q2w had 0.72 times the hazard of a first HAE attack after 0 days of treatment compared to those treated with Cinryze® treatment (Table 21). Lanadelumab 300 mg q4w treatment resulted with nearly the same hazard of HAE attacks when compared to Cinryze®. This finding was not statistically significant as evidence by inclusion of the value "1" in the corresponding 95% CIs. The results were consistent with the base case.

TABLE 21

Indirect Comparison of Lanadelumab and Cinryze ® Using the Bucher Method (Base Case).

| | | ITC | | |
|---|---|---|---|---|
| Treatment 1 | Treatment 2 | HR | 95% CI Lower | 95% CI Upper |
| Lanadelumab 300 mg q2w | Cinryze ® | 0.7157 | 0.2735 | 1.8727 |
| Lanadelumab 300 mg q4w | Cinryze ® | 0.9988 | 0.4045 | 2.4659 |

In the non-parametric estimation, the mean time to first attack (in days) after 70 days of placebo treatment was considerably shorter in the CHANGE study than in the HELP study (3.1429 days [SE 0.5625] vs. 21.378 days [SE 4.687]).

Figure 11:
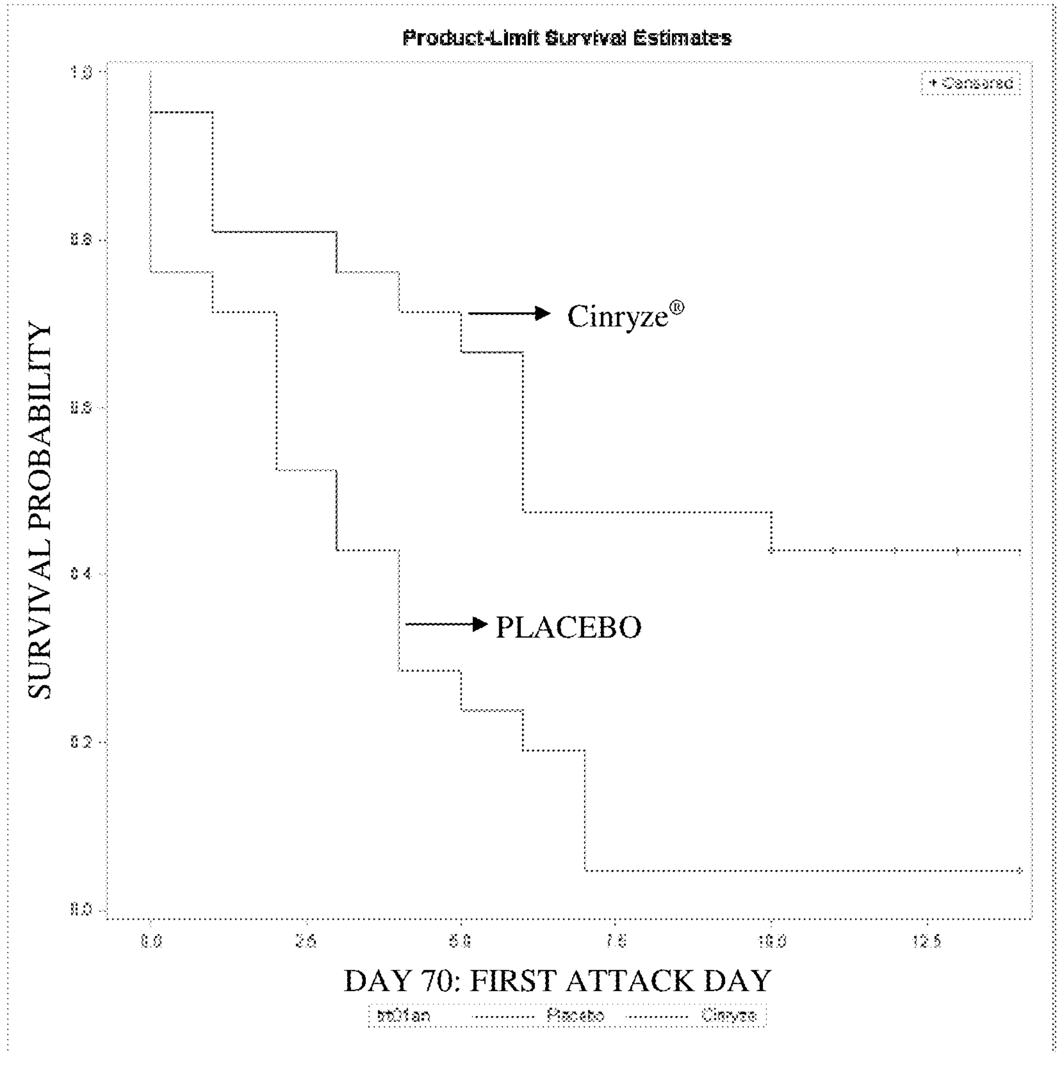
FIG. 11 is a predicted survival graph comparing time to first attack after 70 days of treatment with placebo or Cinryze® (C1-INH) in the CHANGE study.

The probability of "no first attack" after 70 days of treatment is plotted on the y-axis of the graph in FIG. 11, while the observation time horizon is plotted on the x-axis. In the CHANGE study, placebo was less effective than Cinryze® treatment. Patients treated with placebo experienced their first attack considerably earlier than during treatment with Cinryze®. Given that the two curves do not intersect, it can concluded that the Cox regression is a valid method for estimating HRs for the ITC.

Figure 12:
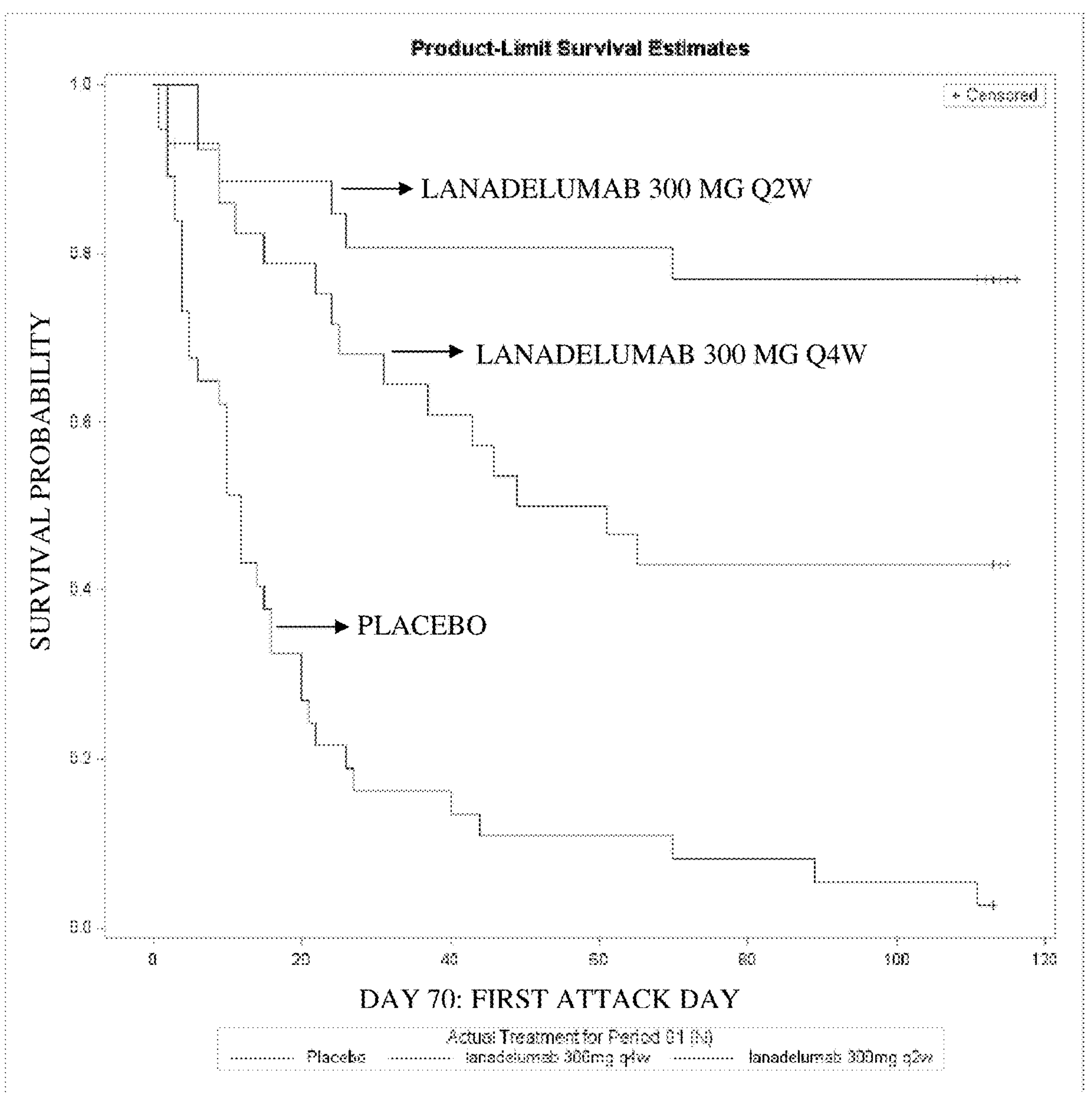
FIG. 12 is a predicted survival graph comparing time to first attack after 70 days of treatment with placebo, 300 mg lanadelumab every 2 weeks (300 mg q2w), or 300 mg lanadelumab every 4 weeks (300 mg q4w) in the HELP (HELP-03) study.

As shown in FIG. 12, the probably of "no first attack" after 70 days of treatment is plotted on the y-axis of and the observation time horizon is plotted on the x-axis. Placebo treatment was less effective than lanadelumab treatment (300 mg q2w and 300 mg q4w) in the HELP study. Patients treated with placebo experienced first attacks considerably earlier than those treated with lanadelumab. Given that none of the curves intersect, it can be concluded that the Cox is a valid method for estimating HRs for the ITC.

In comparing Cinryze® and placebo, the Cox regression generated a HR of 0.34 (95% CI: 0.16; 0.72). In the Bayesian NMA, the corresponding HR was 0.53 (0.00; 318.88) (Table 22).

TABLE 22

Base Case Results in the CHANGE Study.

| Contrast | HR | Standard Error | Confidence Limits | | Bayesian NMA (FE): HR and 95% credible interval (Crl) |
|---|---|---|---|---|---|
| Cinryze ® vs. placebo | 0.3421 | 0.1287 | 0.1636 | 0.7153 | 0.53 (0.00; 318.88) |

In comparing lanadelumab 300 mg q2w and lanadelumab 300 mg q4w to placebo, the Cox regression yielded HRs of 0.07 (95% CI; 0.03; 0.16) and 0.21 (95% CI; 0.11; 0.40), respectively (Table 23). In the Bayesian NMA, the corresponding HRs were 0.09 (95% CI; 0.04; 0.22) and 0.27 (95% CI; 0.14; 0.53), respectively.

TABLE 23

Base Case Results in the HELP Study.

| Contrast | HR | SE | 95% CI Lower | 95% CI Upper | Bayesian NMA (FE): HR |
|---|---|---|---|---|---|
| Lanadelumab 300 mg q2w vs. placebo | 0.0651 | 0.0306 | 0.0259 | 0.1638 | 0.09 (0.04; 0.22) |
| Lanadelumab 300 mg q4w vs. placebo | 0.2116 | 0.0686 | 0.1121 | 0.3996 | 0.27 (0.14; 0.53) |

Indirect comparison via the Bucher method showed that patients treated with lanadelumab 300 mg q2w had 0.19 times the hazard of a first HAE attack after 70 days of treatment compared to those treated with Cinryze® (Table 24). These results were statistically significant as evidenced by exclusion of the value "1" in the corresponding 95% CIs (95% CI: 0.0584; 0.6200). The hazard of HAE attacks during treatment with lanadelumab 300 mg q4w was 0.62 times the hazard of attacks during Cinryze® treatment. These results comparing treatment with lanadelumab 300 mg q4w to treatment with Cinryze® were not statistically significant, as evidenced by the inclusion of "1" in the corresponding 95% CIs (95% CI: 0.2336, 1.6381) . . . . The point estimates generated in the ITC using IPD differed from the results of the Bayesian NMA. As the interval bounds appeared similar, the conclusions did not change.

TABLE 24

Indirect Comparison of Lanadelumab and Cinryze ® via the Bucher Method (Base Case).

| | | ITC | | | |
|---|---|---|---|---|---|
| Treatment 1 | Treatment 2 | HR | 95% CI Lower | 95% CI Upper | Bayesian NMA: HR |
| Lanadelumab 300 mg q2w | Cinryze ® | 0.1903 | 0.0584 | 0.6200 | 0.17 (0.05; 0.57) |
| Lanadelumab 300 mg q4w | Cinryze ® | 0.6186 | 0.2336 | 1.6381 | 0.51 (0.18; 1.49) |

In comparing lanadelumab 300 mg q2w and lanadelumab 300 mg q4w to placebo, the Cox regression yielded HRs of 0.05 (95% CI; 0.02; 0.14) and 0.19 (95% CI; 0.10; 0.38), respectively (Table 25). The addition of the covariate inclusion did not have an impact.

TABLE 25

Base Case Results in the HELP Study.

| Comparison | HR | SE | 95% CI Lower | 95% CI Upper |
|---|---|---|---|---|
| Lanadelumab 300 mg q2w vs. placebo | 0.0516 | 0.0266 | 0.0188 | 0.1417 |
| Lanadelumab 300 mg q4w vs. placebo | 0.1930 | 0.0658 | 0.0990 | 0.3764 |

In comparing Cinryze® and placebo, the Cox regression generated a HR of 0.32 (95% CI: 0.14; 0.71) (Table 26). These results were consistent with the base case findings.

TABLE 26

Base Case Results in the CHANGE Study.

| Contrast | HR | SE | 95% CI Lower | 95% Upper |
|---|---|---|---|---|
| HR Cinryze ® vs. placebo | 0.3193 | 0.1295 | 0.1441 | 0.7072 |

Indirect comparison via the Bucher method showed that patients treated with lanadelumab 300 mg q2w had 0.15 times the hazard of a first HAE attack after 70 days of treatment compared to those treated with Cinryze® (Table 27). These results were statistically significant as evidenced by exclusion of the value "1" in the corresponding 95% CIs (95% CI: 0.0431; 0.5286). Treatment with lanadelumab 300 mg q4w resulted in 0.56 times the hazard of HAE attacks when compared with Cinryze®. These results comparing treatment with lanadelumab 300 mg q4w to treatment with Cinryze® were not statistically significant, as evidenced by the inclusion of "1" in the corresponding 95% CIs (95% CI: 0.2086, 1.5262).

TABLE 27

Indirect Comparison of Lanadelumab and Cinryze ® via the Bucher Method (Base Case).

| | | ITC | | |
|---|---|---|---|---|
| Treatment 1 | Treatment 2 | HR | 95% CI Lower | 95% CI Upper |
| Lanadelumab 300 mg q2w | Cinryze ® | 0.1508 | 0.0431 | 0.5286 |
| Lanadelumab 300 mg q4w | Cinryze ® | 0.5643 | 0.2086 | 1.5262 |

Conclusion

Consistent with the results of the Bayesian NMA using aggregate data, the present regression-based frequentist ITC demonstrated that lanadelumab 300 mg q2w and lanadelumab 300 mg q4w were statistically more effective than Cinryze® at reducing the rate of HAE attacks per 28 days (RR 0.27, 95% CI [0.15; 0.49] and RR 0.54, 95% CI [0.35; 0.85], respectively). A sensitivity analysis, which included patient-reported HAE attacks in the HELP study, confirmed these findings and yielded RR point estimates and 95% Cis in line with the primary results. A second sensitivity analysis including the covariates age, gender, and weight produced similar findings and further supported the outcomes of the base case analysis.

With respect to the time to first attack after 0 days of treatment and the time to first attack after 70 days of treatment, the present ITC drew conclusions similar to those noted in the Bayesian NMA. Lanadelumab 300 mg q2w and lanadelumab 300 mg q4w were not statistically more effective compared to Cinryze® in prolonging the time to a first attack after 0 days of treatment (HR 0.73, 95% CI [0.29; 1.84] and HR 1.05, 95% CI [0.43, 2.52], respectively). Lanadelumab 300 mg q2w and lanadelumab 300 mg q4w, however, appeared to exhibit greater efficacy in increasing the time to a first attack after 70 days of treatment compared to Cinryze® (HR 0.19, 95% CI [0.06; 0.62] and HR 0.62, 95% CI [0.23; 1.64], respectively). Only the difference between lanadelumab 300 mg q2w and Cinryze® was statistically significant. In the sensitivity analyses for the time to first attack after 0 and 70 days of treatment, models including age, gender, and weight yielded lower HR point estimates; however, the findings did not change any of the base case conclusions.

Although the conclusions of the present ITC were consistent with those of the Bayesian NMA, the corresponding point estimates and uncertainty intervals differed. This was presumably due to the lack of accounting for repeated measurements in the Bayesian NMA (with respect to the CHANGE cross-over study), as well as differences in data input types.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of examples only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

SEQUENCE LISTING

```
Sequence total quantity: 10
SEQ ID NO: 1             moltype = AA  length = 469
FEATURE                  Location/Qualifiers
REGION                   1..469
                         note = Synthetic Polypeptide
source                   1..469
                         mol_type = protein
                         organism = synthetic construct
SEQUENCE: 1
MGWSCILFLV ATATGAHSEV QLLESGGGLV QPGGSLRLSC AASGFTFSHY IMMWVRQAPG  60
KGLEWVSGIY SSGGITVYAD SVKGRFTISR DNSKNTLYLQ MNSLRAEDTA VYYCAYRRIG  120
VPRRDEFDIW GQGTMVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKRVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPSREE MTKNQVSLTC LVKGFYPSDI AVEWESNGQP ENNYKTTPPV  420
LDSDGSFFLY SKLTVDKSRW QQGNVFSCSV MHEALHNHYT QKSLSLSPG             469

SEQ ID NO: 2             moltype = AA  length = 231
FEATURE                  Location/Qualifiers
REGION                   1..231
                         note = Synthetic Polypeptide
source                   1..231
                         mol_type = protein
                         organism = synthetic construct
SEQUENCE: 2
MGWSCILFLV ATATGAHSDI QMTQSPSTLS ASVGDRVTIT CRASQSISSW LAWYQQKPGK  60
APKLLIYKAS TLESGVPSRF SGSGSGTEFT LTISSLQPDD FATYYCQQYN TYWTFGQGTK  120
VEIKRTVAAP SVFIFPPSDE QLKSGTASVV CLLNNFYPRE AKVQWKVDNA LQSGNSQESV  180
TEQDSKDSTY SLSSTLTLSK ADYEKHKVYA CEVTHQGLSS PVTKSFNRGE C           231

SEQ ID NO: 3             moltype = AA  length = 122
FEATURE                  Location/Qualifiers
REGION                   1..122
```

```
                       note = Synthetic Polypeptide
source                 1..122
                       mol_type = protein
                       organism = synthetic construct
SEQUENCE: 3
EVQLLESGGG LVQPGGSLRL SCAASGFTFS HYIMMWVRQA PGKGLEWVSG IYSSGGITVY  60
ADSVKGRFTI SRDNSKNTLY LQMNSLRAED TAVYYCAYRR IGVPRRDEFD IWGQGTMVTV  120
SS                                                                122

SEQ ID NO: 4           moltype = AA  length = 106
FEATURE                Location/Qualifiers
REGION                 1..106
                       note = Synthetic Polypeptide
source                 1..106
                       mol_type = protein
                       organism = synthetic construct
SEQUENCE: 4
DIQMTQSPST LSASVGDRVT ITCRASQSIS SWLAWYQQKP GKAPKLLIYK ASTLESGVPS  60
RFSGSGSGTE FTLTISSLQP DDFATYYCQQ YNTYWTFGQG TKVEIK                106

SEQ ID NO: 5           moltype = AA  length = 5
FEATURE                Location/Qualifiers
REGION                 1..5
                       note = Synthetic Polypeptide
source                 1..5
                       mol_type = protein
                       organism = synthetic construct
SEQUENCE: 5
HYIMM                                                             5

SEQ ID NO: 6           moltype = AA  length = 17
FEATURE                Location/Qualifiers
REGION                 1..17
                       note = Synthetic Polypeptide
source                 1..17
                       mol_type = protein
                       organism = synthetic construct
SEQUENCE: 6
GIYSSGGITV YADSVKG                                                17

SEQ ID NO: 7           moltype = AA  length = 13
FEATURE                Location/Qualifiers
REGION                 1..13
                       note = Synthetic Polypeptide
source                 1..13
                       mol_type = protein
                       organism = synthetic construct
SEQUENCE: 7
RRIGVPRRDE FDI                                                    13

SEQ ID NO: 8           moltype = AA  length = 11
FEATURE                Location/Qualifiers
REGION                 1..11
                       note = Synthetic Polypeptide
source                 1..11
                       mol_type = protein
                       organism = synthetic construct
SEQUENCE: 8
RASQSISSWL A                                                      11

SEQ ID NO: 9           moltype = AA  length = 7
FEATURE                Location/Qualifiers
REGION                 1..7
                       note = Synthetic Polypeptide
source                 1..7
                       mol_type = protein
                       organism = synthetic construct
SEQUENCE: 9
KASTLES                                                           7
```

-continued

```
SEQ ID NO: 10           moltype = AA  length = 8
FEATURE                 Location/Qualifiers
REGION                  1..8
                        note = Synthetic Polypeptide
source                  1..8
                        mol_type = protein
                        organism = synthetic construct
SEQUENCE: 10
QQYNTYWT                                                        8
```

What is claimed is:

1. A method for treating hereditary angioedema (HAE) attack or reducing the rate of HAE attack in a subject in need thereof and assessing efficacy of a treatment regimen in a subject, the method comprising:

(i) obtaining a first plasma sample or serum sample from the subject;

(ii) administering to the subject an antibody that binds human plasma kallikrein at about 300 mg every about two weeks in a first treatment period, which is about 4-9 months;

(iii) monitoring the subject for HAE attack during the first treatment period; and (iv) reducing the dosage of the antibody to about 300 mg every about four weeks in the subject, who is free of HAE attack in the first treatment period;

(v) obtaining a second plasma sample or serum sample from the subject after the administration of the antibody;

(vi) measuring a concentration of one or more biomarkers associated with plasma kallikrein in the first plasma sample or serum sample; and (vii) measuring a concentration of the one or more biomarkers associated with plasma kallikrein in the second plasma sample or serum sample;

wherein the treatment regimen is effective if the concentration of the one or more biomarkers is decreased in the second plasma sample or serum sample as compared to the first plasma sample or serum sample; and wherein the antibody comprises a heavy chain complementarity determining region (HC CDR) 1 having the amino acid sequence HYIMM (SEQ ID NO: 5), a HC CDR2 having the amino acid sequence GIYSSGGITVYADSVKG (SEQ ID NO: 6), a HC CDR3 having the amino acid sequence of RRIGVPRRDEFDI (SEQ ID NO: 7), a light chain complementarity determining region (LC CDR) 1 having the amino acid sequence RASQSISSWLA (SEQ ID NO: 8), a LC CDR2 having the amino acid sequence KASTLES (SEQ ID NO: 9) and a LC CDR3 having the amino acid sequence QQYNTYWT (SEQ ID NO: 10);

wherein the one or more biomarkers comprises cleaved high molecular weight kininogen (HMWK); and wherein the subject is a human.

2. The method of claim 1, wherein the measuring is by detecting the one or more biomarkers in an immunoassay.

3. The method of claim 1, wherein the antibody comprises a heavy chain immunoglobulin variable domain ($V_H$) of SEQ ID NO: 3 and a light chain immunoglobulin variable domain ($V_L$) of SEQ ID NO: 4.

4. The method of claim 1, wherein the antibody comprises a heavy chain sequence of amino acids 19-470 of SEQ ID NO: 1 having the amino acid sequence EVQLLESGGGLVQPGGSLRLSCAASGFTFSHYIMMWVRQAPGKGLEWVSGIYSSGGITV YADSVKGRFTISRDNSKNTLYLQMNSLRAEDTAVYYCAYRRIGVPRRDEFDIWGQGTM VTVSSASTKGPSVFPLAPSSKSTSGGTAALGCLVKDYFPEPVTVSWNSGALTSGVHTFPA VLQSSGLYSLSSVVTVPSSSLGTQTYICNVNHKPSNTKVDKRVEPKSCDKTHTCPPCPAP ELLGGPSVFLFPPKPKDTLMISRTPEVTCVVVDVSHEDPEVKFNWYVDGVEVHNAKTKP REEQYNSTYRVVSVLTVLHQDWLNGKEYKCKVSNKALPAPIEKTISKAKGQPREPQVY TLPPSREEMTKNQVSLTCLVKGFYPSDIAVEWESNGQPENNYKTTPPVLDSDGSFFLYSK LTVDKSRWQQGNVFSCSVMHEALHNHYTQKSLSLSPG and a light chain sequence of amino acids 19-232 of SEQ ID NO: 2 having the amino acid sequence DIQMTQSPSTLSASVGDRVTITCRASQSISSWLAWYQQKPGKAPKLLIYKASTLESGVPS RFSGSGSGTEFTLTISSLQPDDFATYYCQQYNTYWTFGQGTKVEIKRTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC.

* * * * *